(12) United States Patent
Naito et al.

(10) Patent No.: US 10,570,215 B2
(45) Date of Patent: Feb. 25, 2020

(54) HUMANIZED MONOCLONAL ANTIBODY, INHIBITING THE ENZYMATIC ACTIVITY OF VASCULAR ENDOTHELIAL LIPASE

(71) Applicant: Shionogi & Co., Ltd., Osaka-shi, Osaka (JP)

(72) Inventors: Shoichi Naito, Toyonaka (JP); Hiroaki Aino, Toyonaka (JP); Etsuo Nakamura, Toyonaka (JP); Sunao Imai, Toyonaka (JP); Shoji Yamane, Toyonaka (JP)

(73) Assignee: SHIONOGI & CO., LTD., Osaka-Shi (JP)

( * ) Notice: Subject to any disclaimer, the term of this patent is extended or adjusted under 35 U.S.C. 154(b) by 9 days.

(21) Appl. No.: 15/456,041

(22) Filed: Mar. 10, 2017

(65) Prior Publication Data

US 2017/0260290 A1 Sep. 14, 2017

Related U.S. Application Data

(63) Continuation of application No. PCT/JP2015/075668, filed on Sep. 10, 2015.

(30) Foreign Application Priority Data

Sep. 11, 2014 (JP) ................. 2014-184710

(51) Int. Cl.
| | |
|---|---|
| C07K 16/40 | (2006.01) |
| A61K 39/395 | (2006.01) |
| A61P 3/06 | (2006.01) |
| C07K 14/47 | (2006.01) |
| A61K 39/00 | (2006.01) |

(52) U.S. Cl.
CPC ........ *C07K 16/40* (2013.01); *A61K 2039/505* (2013.01); *A61P 3/06* (2018.01); *C07K 14/47* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,701,757 B2 * | 7/2017 | Naito ................ | C07K 16/40 |
| 2015/0025225 A1 | 1/2015 | Naito et al. | |

FOREIGN PATENT DOCUMENTS

| | | |
|---|---|---|
| EP | 2 975 060 A1 | 1/2016 |
| WO | WO 99/32611 A1 | 7/1999 |
| WO | WO 00/57837 A2 | 10/2000 |
| WO | WO 2013/054830 A1 | 4/2013 |
| WO | WO 2014/142182 A1 | 9/2014 |

OTHER PUBLICATIONS

English translation of International Preliminary Report on Patentability and Written Opinion dated Mar. 23, 2017, in PCT International Application No. PCT/JP2015/075668.
Basu et al., "Measurement of the phospholipase activity of endothelial lipase in mouse plasma", Journal of Lipid Research, 2013, vol. 54, pp. 282-289.
Broedl et al., "Endothelial Lipase: A Modulator of Lipoprotein Metabolism Upregulated by Inflammation", TCM, 2004, vol. 14, No. 5, pp. 202-206.
Casset et al., "A peptide mimetic of an anti-CD4 monoclonal antibody by rational design", Biochemical and Biophysical Research Communications, 2003, vol. 307, pp. 198-205.
Chen et al., "Selection and Analysis of an Optimized Anti-VEGF Antibody: Crystal Structure of an Affinity-matured Fab in Complex with Antigen", Journal of Molecular Biology, 1999, vol. 293, pp. 865-881.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, vol. 169, pp. 3076-3084.
Griffon et al., "Identification of the Active Form of Endothelial Lipase, a Homodimer in a Head-to-Tail Conformation", The Journal of Biological Chemistry, Aug. 28, 2009, vol. 284, No. 35, pp. 23322-23330.
Holm et al., "Functional mapping and single chain construction of the anti-cytokeratin 8 monoclonal antibody TS1", Molecular Immunology, 2007, vol. 44, pp. 1075-1084.
Ishida et al., Endothelial Lipase Modulates Susceptibility to Atherosclerosis in Apolipoprotein-E-deficient Mice, The Journal of Biological Chemistry, Oct. 22, 2004, vol. 279, No. 43, pp. 45085-45092.
Jaye et al., "A novel endothelial-derived lipase that modulates HDL metabolism", Nature Genetics, Apr. 1999, vol. 21, pp. 424-428.
Jin et al., "Inhibition of endothelial lipase causes increased HDL cholesterol levels in vivo", The Journal of Clinical Investigation, Feb. 2003, vol. 111, No. 3, pp. 357-362.
Kojima et al., "Pitavastatin decreases the expression of endothelial lipase both in vitro and in vivo", Cardiovascular Research, 2010, vol. 87, pp. 385-393.
Kugiyama, "Large-Scale Clinical Study for Establishment of Prophylactic and Therapeutic Techniques for Ischemic Heart Disease and Cerebral Infarction Associated with High Remnant Lipoproteinemia", Heisei 16 Nendo Sokatsu Bunten Kenkyu Hokokusho, 2005, pp. 25-26, total 6 pages.
MacCallum et al., "Antibody-antigen Interactions: Contact Analysis and Binding Site Topography", Journal of Molecular Biology, 1996, vol. 262, pp. 732-745.

(Continued)

*Primary Examiner* — Zachary C Howard
(74) *Attorney, Agent, or Firm* — Birch, Stewart, Kolasch & Birch, LLP

(57) ABSTRACT

Provided is a humanized monoclonal antibody or an antibody fragment thereof that selectively inhibits the enzymatic activity of vascular endothelial lipase and pharmaceutical compositions containing the same as an active ingredient useful for the treatment of arteriosclerosis or metabolic syndrome.

18 Claims, 45 Drawing Sheets

Specification includes a Sequence Listing.

(56) References Cited

OTHER PUBLICATIONS

Razzaghi et al., "Genetic and Structure-Function Studies of Missense Mutations in Human Endothelial Lipase", PLOS ONE, Mar. 2013, vol. 8, Issue No. 3, e55716, total 18 pages.

Rudikoff et al., "Single amino acid substitution altering antigen-binding specificity", Proc. Natl Acad. Sci. USA, Immunology, Mar. 1982, vol. 79, pp. 1979-1983.

Vajdos et al., "Comprehensive Functional Maps of the Antigen-binding Site of an Anti-ErbB2 Antibody Obtained with Shotgun Scanning Mutagenesis", Journal of Molecular Biology, 2002, vol. 320, pp. 415-428.

Wu et al., "Humanization of a Murine Monoclonal Antibody by Simultaneous Optimization of Framework and CDR Residues", Journal of Molecular Biology, 1999, vol. 294, pp. 151-162.

Edmondson et al., "Loss-of-function variants in endothelial lipase are a cause of elevated HDL cholesterol in humans," The Journal of Clinical Investigation, Apr. 2009, vol. 119, No. 4, pp. 1042-1050.

Griffon et al., "Substrate specificity of lipoprotein lipase and endothelial lipase: studes of lid chimeras," Journal of Lipid Research, 2006, vol. 47, pp. 1803-1811.

Hirata et al., "Cloning of a Unique Lipase from Endothelial Cells Extends the Lipase Gene Family", The Journal of Biological Chemistry, May 14, 1999, vol. 274, No. 20, pp. 14170-14175.

International Search Report for PCT/JP2015/075668 dated Nov. 2, 2015.

Ishida et al., "ELISA System for Human Endothelial Lipase," Clinical Chemistry, 2012, vol. 58, No. 12, pp. 1656-1664.

Ishida et al., "Endothelial lipase is a major determinant of HDL level", Journal of Clinical Investigation, 2003, vol. 111, pp. 347-355.

Ishida et al., "Molecular cloning of nonsecreted endothelial cell-derived lipase isoforms", Genomics, 2004, vol. 83, pp. 24-33.

Jin et al., "Endothelial Cells Secrete Triglyceride Lipase and Phospholipase Activities in Response to Cytokines as a Result of Endothelial Lipase", Circulation Research, 2003, vol. 92, No. 6, pp. 644-650, total 10 pages.

Van Tilbeurgh et al., "Lipoprotein Lipase—Molecular model based on the pancreatic lipase X-ray structure: consequences for heparin binding and catalysis", The Journal of Biological Chemistry, Feb. 11, 1994, vol. 269, No. 6, pp. 4626-4633.

Written Opinion of the International Searching Authority for PCT/JP2015/075668 (PCT/ISA/237) dated Nov. 2, 2015.

Yasuda et al., "Update on the Role of Endothelial Lipase in High-Density Lipoprotein Metabolism, Reverse Cholesterol Transport, and Atherosclerosis", Circulation Journal, 2010, vol. 74, pp. 2263-2270.

Communication Pursuant to Rule 164(1) EPC dated Mar. 29, 2018, in European Patent Application No. 15840346.9.

* cited by examiner

Figure 3K
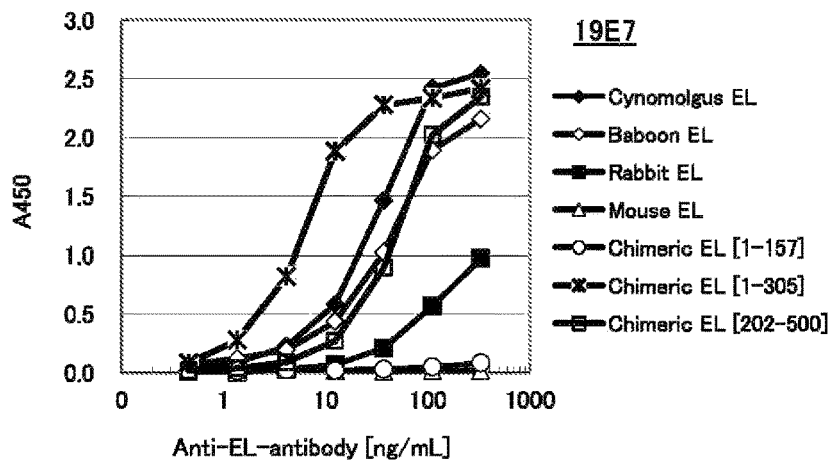
Figure 3L
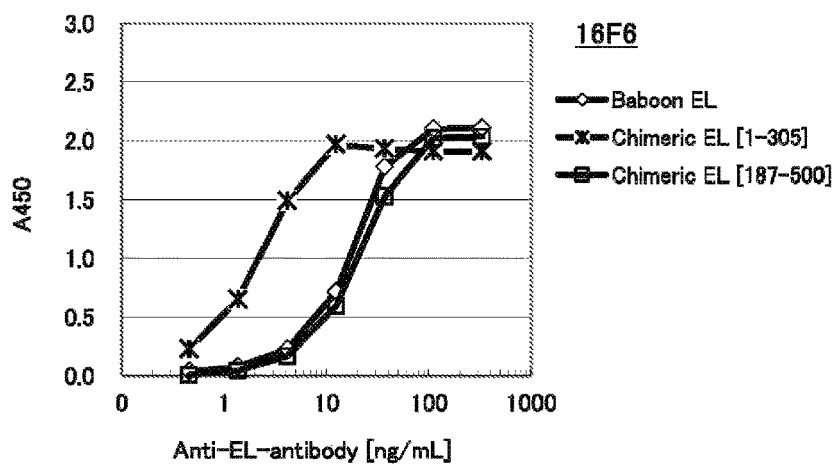
Figure 4A
Heavy chain of 55A1
```
                              CDR1                    CDR2
QIHLVQSGPELKKPGETVKISCKASGYTFTNYGMNWVKQAPGKGLKWMGWINTYSGVPTYAGDF
KGRFAFSLETSASTAYLQINNLKNEDTATYFCARRGYYGRRYFDVWGTGTTVTVSS
                                    CDR3
```
Light chain of 55A1
```
                              CDR1                    CDR2
DIVLTQSPASLAVSLGQRATISCKASQSVDYDVDSYMHWYQQKPGQPPKLLIYAASNLASGI
PARFSGGGSGTDFTLNIHPVEEEDVATYYCQQTIEDPPTFGGGTKLEIK
                             CDR3
```

Figure 4B

Heavy chain of 7D4

```
                                    CDR1                      CDR2
QIQLVQSGPELKKPGETVKISCKASGYTFTNYGMNWVKQAPGKDLKWMGWINTYSGVPTYADDF
KGRFAFSLETSASTAYLQINNLKNEDTATYFCARFSYYGRHYFDYWGQGTTLTVSS
                                    CDR3
```

Light chain of 7D4

```
                                    CDR1                      CDR2
DIVLTQSPASLAVSLGQRATISCKASQSVDYDGDSYMNWYQQKPGQPPQLLIYAASNLGSGI
PARFSGSGSGTDFTLNIHPVEEEDAATYYCHQSTDDPPWTFGGGTKLEIK
                                    CDR3
```

Figure 4C

Heavy chain of 14A1

```
                                    CDR1                      CDR2
QIQLVQSGPELKKPGETVKISCKASGYTFTNYGMNWVKQAPGKGLKWMGWINTYSGVPTYADDF
KGRFAFSLETSASTAYLQINNFKNEDTATYFCARFSYYGRHYFDYWGQGTALTASS
                                    CDR3
```

Light chain of 14A1

```
                                    CDR1                      CDR2
DIVLTQSPASLAVSLGQRATISCKASQSVDYDGDSYMNWYQQKPGQPPKLLIYAASNLKSGI
PARFSGSGSGTDFTLNIHPVEEEDAATYYCQQTTDDPPWTFGGGTKLEIK
                                    CDR3
```

Figure 4D

Heavy chain of 2D5

```
                                    CDR1                      CDR2
QIQLVQSGPELKKPGETVKISCKASGYTFTNYGMNWVKQAPGKGLKWMGWINTYSGVPTYTDDF
KGRFAFSLETSASTAFLQINNLKNEDTATYFCARFSYYGRHYFDYWGQGTTLTVSS
                                    CDR3
```

Light chain of 2D5

```
                                    CDR1                      CDR2
DIVLTQSPASLAVSLGQRATISCKASQSVDYDGDSYMHWYQQKPGQPPKLLIYAASNLESGI
PARFSGSGSGTDFTLNIHPVEEEDAATYYCQQTNDDPPWTFGGGTKLEIK
                                    CDR3
```

Figure 4E

Heavy chain of 53A11

CDR1                        CDR2

EVQLQQSGPELLKPGASVKISCKASGYTFTDYTMHWVKQSHGKSLEWIGGINPYYGGTTYNEKF
KDKATLTVDKSSSTAYMELRSLTSEDSAVYYCAKGDYYGGSYNYWGQGTTLTVSS
                                          CDR3

Light chain of 53A11

CDR1                      CDR2

DIVLTQSLATLSVTPGDSVSLSCRASQDISNSLHWYQQKSHESPRLLIKYASQSISGIPSRF
SGSGSGTDFTLSINSVETEDFGMYFCQQSNSWPYTFGGGTKLEIK
                                CDR3

Figure 4F

Heavy chain of 13B3

CDR1                      CDR2

EVQLQQSGPELLKPGASVKISCKASGYTFTEYTMHWVKQSHGKSLEWIGSINPYYGGTSYNEKF
KDKATLTVDKSSNTAYMEFRSLTSEDCAVYYCARYGNYVGYFDYWGQGTTLTVSS
                                      CDR3

Light chain of 13B3

CDR1                      CDR2

ENVLTQSPAIMSASLGEKVTMSCRASSSVHYMYWYQQKSDASPKLWIYYTSNLAPGVPDRFS
GSGSGNSYSLTISSMEGEDAATYYCQQFTSSPYTFGGGTKLEIK
                                CDR3

Figure 4G

Heavy chain of 23H8

CDR1                      CDR2

EVQLQQSGPELLKPGASVKISCKASGYTFTDNTIHWVKQSHGKSLEWIGHINPYYGGTNNNEKF
KDKATLTVDKSSSTAYMELRSLTSEDSAIYYCARKGIYYSSPFDYWGQGTTLTVSS
                                      CDR3

Light chain of 23H8

CDR1                      CDR2

DIQMTQTTSSLSASLGDRVTISCRASQDINNYLNWYQQKPDGTVKLLISYTSKLHSGVPS

RFSGSGSGTDYSLTISNLEREDFATYFCQQGNTLPFTFGSGTNLEIK
                              CDR3

Figure4H

Heavy chain of 16B3

CDR1                          CDR2

DVKLVESGGGLVQPGGSLKLSCTASGFTFSGYTMSWVRQTPEKRLELVAEISFARDRAFYPDTV

KGRFTISRDNAKNTLYLQMSSLKSEDTAMYYCTRLGGRNHDYWYFDVWGTGTTVTVSS

CDR3

Light chain of 16B3

CDR1                          CDR2

DIVLTQSPTSLAVSPGQRATISCRASESVEYYGTSLMQWYQQKPGQRPQLLIYAASNVESGV

PARFSGSGSGTDFSLNIHPVEEDDIAVYFCQQSWKVPFTFGSGTKLEIK

CDR3

Figure4I

Heavy chain of 16E7

CDR1                          CDR2

EVKLVESGGGLVQPGGSLKLSCAASGFTFSSYTMSWVRQTPEKRLELVAEISFTRSRAFYPDTV

KGRFTISRDNAKNTLYLQMSSLKSEDTAMYYCARLGGNNYDYWYFDVWGTGTTVTVSS

CDR3

Light chain of 16E7

CDR1                          CDR2

DIVLTQSPTSLAVSLGQRATISCRASESVEYYGTSLMQWYQQKPGQRPKLLIYAASNVESGV

PARFSGSGSGTDFSLNIHPVEEDDIAMYFCQQSWKVPFTFGSGTKLEIK

CDR3

Figure4J

Heavy chain of 14E1

CDR1                          CDR2

QVQLQQSGAELVKPGASVRLSCKASGYTFTKYTIHWVKQRSGQGLEWIGWFYPGSDSIKYNEKF

KDKATLTADKSSRTVYMELSRLTSEDSAVYFCARHEEYTNSLAYWGQGTLVTVSA

CDR3

Light chain of 14E1

CDR1                          CDR2

DIQMTQTTSSLSASLGDRVTISCRASQDISNYLNWYQQQPDGTVKLLIYYTSRLHSGVPSRF

SGSGSGTDYSLTISNLEQEDIATYFCQQGYTLPWTFGGGTNLEIK

CDR3

Figure4K

Heavy chain of 19E7

CDR1                      CDR2

QVQLQQPGSVLVRPGASVKLSCKASGYTFTTYWMHWVKQRPGQGLEWIGEIHPYSGNNNNNEKF

KGKATLTVDTSSSTAYVDLSRLTSEDSAVYYCARYDSNYVFAYWGQGTLVTVSA
                                          CDR3

Light chain of 19E7

CDR1                     CDR2

QIVLTQSPAIMSASPGEGVTITCSASSSVSYMHWFQQKPGTSPKLWIYSTSNLASGVPARFS

GSGSGTSYSLTISRMEAEDAATYYCQQRDSYLTFGSGTKLEVK
                             CDR3

Figure4L

Heavy chain of 16F6

CDR1                       CDR2

QVQLQQSGAELMKPGASVKISCKATGYTFSTYWIAWVKQRPGHGLEWIGEILPGSAKTKYNKKF
KGKATFTADTSSNTAYMQLSSLTSEDSAVYYCAVYDYGADYWGQGTSVTVSS
                                      CDR3

Light chain of 16F6

CDR1                           CDR2

DIVMTQSHKFMSTSVGDRVSITCKASQDVYTAVAWYQQKPGQSPKLLIYSASYRFTGVPDRF
TGSGAGTEFTFTINSVQAEDLAVYYCQQHYSIPRTFGGGTKLEIK
                                  CDR3

Figure5A

```
55A1   1:QIHLVQSGPELKKPGETVKISCKASGYTFTNYGMNWVKQAPGKGLKWMGWINTYSGVPTY 60
7D4    1:QIQLVQSGPELKKPGETVKISCKASGYTFTNYGMNWVKQAPGKDLKWMGWINTYSGVPTY 60
14A1   1:QIQLVQSGPELKKPGETVKISCKASGYTFTNYGMNWVKQAPGKGLKWMGWINTYSGVPTY 60
2D5    1:QIQLVQSGPELKKPGETVKISCKASGYTFTNYGMNWVKQAPGKGLKWMGWINTYSGVPTY 60

55A1  61:AGDFKGRFAFSLETSASTAYLQINNLKNEDTATYFCARRGYYGRRYFDVWGTGTTVTVSS 120
7D4   61:ADDFKGRFAFSLETSASTAYLQINNLKNEDTATYFCARFSYYGRHYFDYWGQGTTLTVSS 120
14A1  61:ADDFKGRFAFSLETSASTAYLQINNFKNEDTATYFCARFSYYGRHYFDYWGQGTALTASS 120
2D5   61:TDDFKGRFAFSLETSASTAFLQINNLKNEDTATYFCARFSYYGRHYFDYWGQGTTLTVSS 120
```

Figure 5B

```
55A1   1:DIVLTQSPASLAVSLGQRATISCKASQSVDYDVDSYMHWYQQKPGQPPKLLIYAASNLAS  60
7D4    1:DIVLTQSPASLAVSLGQRATISCKASQSVDYDGDSYMNWYQQKPGQPPQLLIYAASNLGS  60
14A1   1:DIVLTQSPASLAVSLGQRATISCKASQSVDYDGDSYMNWYQQKPGQPPKLLIYAASNLKS  60
2D5    1:DIVLTQSPASLAVSLGQRATISCKASQSVDYDGDSYMHWYQQKPGQPPKLLIYAASNLES  60

55A1  61:GIPARFSGGGSGTDFTLNIHPVEEEDVATYYCQQTIEDPP-TFGGGTKLEIK         111
7D4   61:GIPARFSGSGSGTDFTLNIHPVEEEDAATYYCHQSTDDPPWTFGGGTKLEIK         112
14A1  61:GIPARFSGSGSGTDFTLNIHPVEEEDAATYYCQQTTDDPPWTFGGGTKLEIK         112
2D5   61:GIPARFSGSGSGTDFTLNIHPVEEEDAATYYCQQTNDDPPWTFGGGTKLEIK         112
```

Figure 5C

```
53A11  1:EVQLQQSGPELLKPGASVKISCKASGYTFTDYTMHWVKQSHGKSLEWIGGINPYYGGTTY  60
13B3   1:EVQLQQSGPELLKPGASVKISCKASGYTFTEYTMHWVKQSHGKSLEWIGSINPYYGGTSY  60
23H8   1:EVQLQQSGPELLKPGASVKISCKASGYTFTDNTIHWVKQSHGKSLEWIGHINPYYGGTNN  60

53A11 61:NEKFKDKATLTVDKSSSTAYMELRSLTSEDSAVYYCAKGD-YYGGSYNYWGQGTTLTVSS  119
13B3  61:NEKFKDKATLTVDKSSNTAYMEFRSLTSEDCAVYYCARYG-NYVGYFDYWGQGTTLTVSS  119
23H8  61:NEKFKDKATLTVDKSSSTAYMELRSLTSEDSAIYYCARKGIYYSSPFDYWGQGTTLTVSS  120
```

Figure 5D

```
53A11  1:DIVLTQSLATLSVTPGDSVSLSCRASQDISNSLHWYQQKSHESPRLLIKYASQSISGIPS  60
13B3   1:ENVLTQSPAIMSASLGEKVTMSCRASSSV-HYMYWYQQKSDASPKLWIYYTSNLAPGVPD  59
23H8   1:DIQMTQTTSSLSASLGDRVTISCRASQDINNYLNWYQQKPDGTVKLLISYTSKLHSGVPS  60

53A11 61:RFSGSGSGTDFTLSINSVETEDFGMYFCQQSNSWPYTFGGGTKLEIK              107
13B3  60:RFSGSGSGNSYSLTISSMEGEDAATYYCQQFTSSPYTFGGGTKLEIK              106
23H8  61:RFSGSGSGTDYSLTISNLEREDFATYFCQQGNTLPFTFGSGTNLEIK              107
```

Figure 6A

```
16B3   1:DVKLVESGGGLVQPGGSLKLSCTASGFTFSGYTMSWVRQTPEKRLELVAEISFARDRAFY  60
16E7   1:EVKLVESGGGLVQPGGSLKLSCAASGFTFSSYTMSWVRQTPEKRLELVAEISFTRSRAFY  60

16B3  61:PDTVKGRFTISRDNAKNTLYLQMSSLKSEDTAMYYCTRLGGRNHDYWYFDVWGTGTTVTV  120
16E7  61:PDTVKGRFTISRDNAKNTLYLQMSSLKSEDTAMYYCARLGGNNYDYWYFDVWGTGTTVTV  120

```
16B3    1:DIVLTQSPTSLAVSPGQRATISCRASESVEYYGTSLMQWYQQKPGQRPQLLIYAASNVES    60
16E7    1:DIVLTQSPTSLAVSLGQRATISCRASESVEYYGTSLMQWYQQKPGQRPKLLIYAASNVES    60

16B3   61:GVPARFSGSGSGTDFSLNIHPVEEDDIAVYFCQQSWKVPFTFGSGTKLEIK          111
16E7   61:GVPARFSGSGSGTDFSLNIHPVEEDDIAMYFCQQSWKVPFTFGSGTKLEIK          111
```

Figure6C

```
14E1    1:QVQLQQSGAELVKPGASVRLSCKASGYTFTKYTIHWVKQRSGQGLEWIGWFYPGSDSIKY   60
19E7    1:QVQLQQPGSVLVRPGASVKLSCKASGYTFTTYWMHWVKQRPGQGLEWIGEIHPYSGNNNN   60

14E1   61:NEKFKDKATLTADKSSRTVYMELSRLTSEDSAVYFCARHEEYTNSLAYWGQGTLVTVSA   119
19E7   61:NEKFKGKATLTVDTSSTAYVDLSRLTSEDSAVYYCARYDS-NYVFAYWGQGTLVTVSA   118
```

Figure6D

```
14E1    1:DIQMTQTTSSLSASLGDRVTISCRASQDISNYLNWYQQQPDGTVKLLIYYTSRLHSGVPS   60
19E7    1:QIVLTQSPAIMSASPGEGVTITCSASSSVS-YMHWFQQKPGTSPKLWIYSTSNLASGVPA   59

14E1   61:RFSGSGSGTDYSLTISNLEQEDIATYFCQQGYTLPWTFGGGTNLEIK             107
19E7   60:RFSGSGSGTSYSLTISRMEAEDAATYYCQQRDSY-LTFGSGTKLEVK             105
```

Figure7A

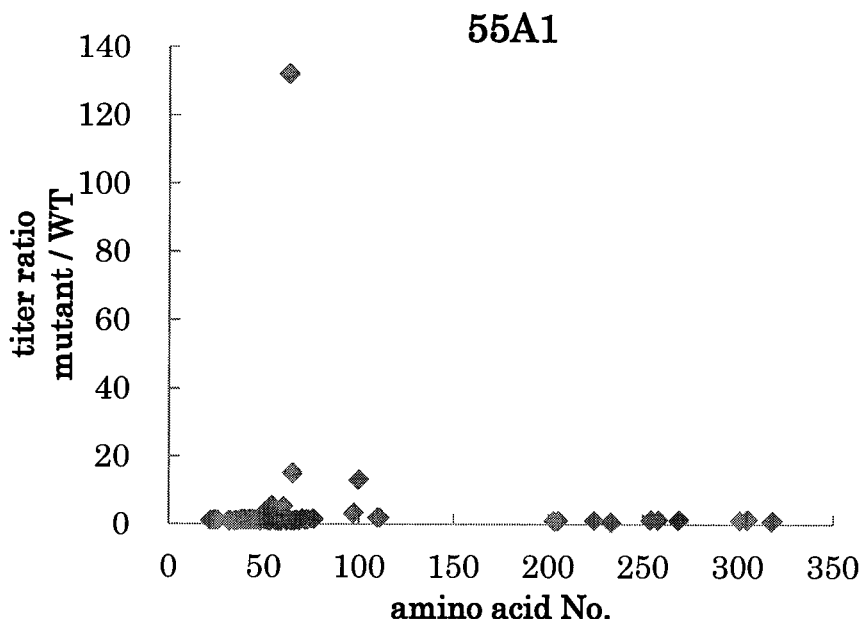

Heavy chain of h16B3

Figure 8B
Light chain of h16B3

Kabat numbering

```
                    1111111111222222222233333333334444444444555555
         123456789 0123456789012345678901234567890123456789012345
h16B3 S1-L  DIVMTQSPDSLAVSLGERATINCRASESVEYYGTSLMQWYQQKPGQPPKLLIYAASNVES
h16B3 S2-L  ............................................................
h16B3 S3-L  ............................................................
h16B3 S4-L  ............................................................
h16B3 S5-L  ............................................................
h16B3 S6-L  ............................................................
h16B3 S7-L  ............................................................
h16B3 S8-L  ............................................................

5556666666666777777777788888888889999999999 1111111
            7890123456789012345678901234567890123456789 0000000
                                                        0123456
h16B3 S1-L  GVPDRFSGSGSGTDFTLTISSLQAEDVAVYYCQQSWKVPFTFGQGTKLEIK
h16B3 S2-L  ..........................................
h16B3 S3-L  ..........................................
h16B3 S4-L  ...............................R..........
h16B3 S5-L  ..........................................
h16B3 S6-L  ...............................R..........
h16B3 S7-L  ..........................................
h16B3 S8-L  ...............................R..........
```

Figure 8C
Heavy chain of h16B3

Kabat numbering

```
                    111111111122222222223333333333444444444455555555
         123456789 0123456789012345678901234567890123456789012345
h16B3 F1-H  EVQLVESGGGLVQPGGSLRLSCAASGFTFSGYTMSWVRQAPGKGLEWVSEISFARDRAFY
h16B3 F2-H  ............................................................
h16B3 F3-H  ............................................................

h16B3 F1-H  PDTVKGRFTISRDNSKNTLYLQMNSLRAEDTAVYYCARLGGRKHDYWYFDVWGQGTTVTV
h16B3 F2-H  ............................................................
h16B3 F3-H  ............................................................

h16B3 F1-H  SS
h16B3 F2-H  ..
h16B3 F3-H  ..
```

Figure 8D
Light chain of h16B3

Kabat numbering

```
h16B3 F1-L  DIVMTQSPDSLSASVGDRVTLTCRASESVEYYGTSLMQWYQQKPGKAPKLLIYAASNVES
h16B3 F2-L  E.V....MT..M.P.E.A.LS.................Q..R............
h16B3 F3-L  E.V....GT..L.P.E.A.LS.................Q..R............

h16B3 F1-L  GVPSRFSGSGSGTDFTLTISSLQPEDFATYYCQQSWKVPFTFGQGTKLEIK
h16B3 F2-L  .I.P.........E.......R.V...........
h16B3 F3-L  .I.D.........R.E.....V...........
```

Figure 9A
Heavy chain of h55A1

Kabat numbering

```
                1         1111111112222222222333333333344444444445555 5555555
       123456789 0123456789012345678901234567890123456789012 3456789
                                                            A
h55A1 S1-H  QVQLVQSGSELKKPGASVKVSCKASGYTFTNYGMNWVRQAPGQGLEWMGWINTYSGVETY
h55A1 S2-H  ...............................L............................
h55A1 S3-H  ...............................L............................
h55A1 S4-H  ...............................A...........................G..
h55A1 S5-H  ...............................A...........................G..
h55A1 S6-H  ...............................AL..........................G..
h55A1 S7-H  ...............................AL..........................G..
```

```
       6666666666777777777788 888 888888889999999999 111 1111111111111
       0123456789012345678901 2 345678901234567890 000 0000000001111
                              222                  000
                              ABC                  ABC 1234567890123
h55A1 S1-H  AGDFKGREVFSLDTSVSTAYLQISSLKAEDTAVYYCARRSIYGRFFDVWGKGTTVTVSS
h55A1 S2-H  .........................................F....F.............
h55A1 S3-H  ........................................S.F....F.............
h55A1 S4-H  .........................................F....F.............
h55A1 S5-H  .........................................F....F.............
h55A1 S6-H  ..E......................................F....F.............
h55A1 S7-H  ..E......................................F....F.............
```

Figure 9B
Light chain of h55A1

Kabat numbering

```
                     1111111111222222222 2222 2333333333344444444445555555
       123456789 0123456789012345678901234567 ABCD 8901234567890123456
h55A1 S1-L  DIVLTQSPASLAVSPGQRATITCKASQSVDYDVDSYMHWYQQKPGQPPKLLIYAASNLAS
h55A1 S2-L  ............................................................
h55A1 S3-L  ............................................................
h55A1 S4-L  ............................................................
h55A1 S5-L  ............................................................
h55A1 S6-L  ............................................................
h55A1 S7-L  ............................................................
```

```
       5556666666666777777777788888888889999999999 1111111
       7890123456789012345678901234567890123456789 0000000
                                                  0123456
h55A1 S1-L  GVPARFSGSGSGTDFTLTINPVEANDLANYYCQQTIEDPPTFGGGTKVEIK
h55A1 S2-L  ...................................................
h55A1 S3-L  .....................................N...........
h55A1 S4-L  ...................................................
h55A1 S5-L  .....................................N...........
h55A1 S6-L  ...................................................
h55A1 S7-L  .....................................N...........
```

Figure 9C
Heavy chain of h55A1

Kabat numbering

```
                    1111111111222222222233333333334444444444555 5555555
          123456789 0123456789012345678901234567890123456789012 3456789
                                                               A
h55A1 F1-H QVQLVQSGSELKKPGASVKVSCKASGYTFTNYGMNWVRQAPGQGLEWMGWINTYSGVPTY
h55A1 F2-H .........A.V................................................
h55A1 F3-H .........A.V................................................
h55A1 F4-H .........A.V................................................
h55A1 F5-H .........A.V................................................
h55A1 F6-H .........A.V................................................
```

```
                                              888                     111 1111111111
          6666666666777777777788 88888889999999999 000 0000000000111
          0123456789012345678901 2 34567890123456789 000 0000000000111
                                ABC                 ABC 1234567890123
h55A1 F1-H AGDFKGRFVFSLDTSVSTAYLQISSLKAEDTAVYYCARRGYYGRRYFDVWGKGTTVTVSS
h55A1 F2-H ......VMTI...T....MEL..RS...................................
h55A1 F3-H ......VMTI...T....MEL..RS...................................
h55A1 F4-H ......VMTI...T....MEL..RS...................................
h55A1 F5-H ......I I....T....MEL..RS...................................
h55A1 F6-H ......I I....T....MEL..RS...................................
```

Figure 9D
Light chain of h55A1

Kabat numbering

```
                    111111111122222222 2222 22333333333344444444445555555
          123456789 012345678901234567 7777 8901234567890123456789012345 6
                                       ABCD
h55A1 F1-L DIQLTQSSSSLSASVGDRVTITCKASQSVDYDVEGYMHWYQQKPGKAPKLLIYAASNLAS
h55A1 F2-L E.VM....AT..V.P.E.L.LS..................Q.R..................
h55A1 F3-L ..............................................Q.............
h55A1 F4-L E.M.....GT..L.P.E..VLS..................Q.R..................
h55A1 F5-L ..............................................Q.R..............
h55A1 F6-L E.VM....AT..V.P.E.A.LS..................Q.R..................
```

```
          5556666666666777777777788888888889999999999 11111111
          7890123456789012345678901234567890123456789 00000000
                                                     01234567
h55A1 F1-L GVPSRFSGSGSGTDFTLTISSLQPEDFATYYCQQTIEDPPTFGSGTKVEIK
h55A1 F2-L ..I.K..........L......S....F.M....................
h55A1 F3-L ...............L...........F......................
h55A1 F4-L ..I.D..........L...R.S.....F.M....................
h55A1 F5-L ..I.A..........S.......S...F.M....................
h55A1 F6-L ..I.A..........L......S....F.M....................
```

Figure 10A
Heavy chain of h53A11

Kabat numbering

```
                    1111111111222222222233333333334444444444555 5555555
          123456789 0123456789012345678901234567890123456789012 3456789
                                                               A
h53A11 S1-H QVQLVQSGAEVKKPGASVKVSCKASGYTFTDYTMHWVRQAPGQFLEWMGGINPYYGGTTY
h53A11 S2-H ............................................................
h53A11 S3-H ............................................................
h53A11 S4-H ............................................................
```

```
          6666666666777777777788 888 88888899999999991 00 1111111111
          0123456789012345678901 234 56789012345678901 00 0000001111
                                ABC                   AB 1234567890123
h53A11 S1-H NEKFKDRVTITRDTSASTAYMELSSLRSEDTAVYYCAKGDYYGGSYNYWGQGTTVTVSS
h53A11 S2-H ............................................................
h53A11 S3-H ............................................................
h53A11 S4-H ............................R...............................
```

Figure 10B
Light chain of h53A11

Kabat numbering

```
             1111111111222222222233333333334444444444555555555566
    123456789 0123456789012345678901234567890123456789012345678901234567890
h53A11 S1-L  EIVMTQSPATLSVSPGERATLSCRASQDISNSLHWYQQKPGQAPRLLIKYASQSISGIPA
h53A11 S2-L  .......................................X..................
h53A11 S3-L  .......P....................................................
h53A11 S4-L  .......P....................................................
```

```
    66666666667777777777888888888899999999991111111
    1234567890123456789012345678901234567890000000000
                                             01234567
h53A11 S1-L  RFSGSGSGTEFTLTISSLQSEDFAVYYCQQSNSWPYTFGQGTKLEIK
h53A11 S2-L  ...............................................
h53A11 S3-L  ...............................................
h53A11 S4-L  ...............................................
```

Figure 11A
Heavy chain of h23H8

Kabat numbering

```
             111111111122222222223333333333444444444455 5 5555555
    123456789 01234567890123456789012345678901234567890123452A456789
h23H8 S1-H   QVQLVQSGAEVKKPGASVKVSCKASGYTFTDNTIHWVRQAPGQGLEWMGHINPYYGGTNN
h23H8 S2-H   ............................................................
h23H8 S3-H   ............................................................
```

```
    6666666666777777777788888 8 8 8888888999999999911111111111111111
    0123456789012345678901234567890123456789012345678901234567890123
                         2 2 2                       0000000000011111
                         A B C                       0000
h23H8 S1-H   NEKFKDRVTMTRDTSISTAYMELSRLRSDDTAVYYCARKGIYYSSPFDYWGQGTTVTVSS
h23H8 S2-H   ............................................................
h23H8 S3-H   ............................................................
```

Figure 11B
Light chain of h23H8

Kabat numbering

```
             1111111111222222222233333333334444444444555555555566
    123456789 0123456789012345678901234567890123456789012345678901234567890
h23H8 S1-L   DIQMTQSPSSLSASVGDRVTITCRASQDINNYLNWYQQKPGKAPKLLIYYTSKLHSGVPS
h23H8 S2-L   ......................................................S....
h23H8 S3-L   ......................................................S....
```

```
    666666666677777777778888888888999999999911111111
    1234567890123456789012345678901234567890000000000
                                             01234567
h23H8 S1-L   RFSGGGSGTDFTLTISSLQPEDFATYYCQQGNTLPFTFGQGTKLEIK
h23H8 S2-L   ..............E..................................
h23H8 S3-L   ...............................................
```

Figure 12A
Heavy chain of h13B3

Kabat numbering

```
                    1111111111222222222233333333334444444444555 5555555
           123456789012345678901234567890123456789012345678901254567890
h13B3 S1-H QVQLVQSGAEVKKPGASVKVSCKASGYTFTEYTMHWVRQAPGQGLEWMGSINPYYGGTSY
h13B3 S2-H ............................................................
h13B3 S3-H ............................................................
h13B3 S4-H ............................................................

6666666666777777777788 888 8888888999999999911111111111111
           01234567890123456789012 222 345678901234567890 00000000001111
                                  ABC                    0A B 12345678901234
h13B3 S1-H NEKFEDRVTMTRDTSTSTVYMELSSLRSEDTAVYYCARYGNVGYFDYWGQGTTVTVSS
h13B3 S2-H .........S......T..A......R......T..V..........................
h13B3 S3-H ................................................................
h13B3 S4-H .........S......T..A......R......T..V..........................
```

Figure 12B
Light chain of h13B3

Kabat numbering

```
                    11111111112222222222333333333344444444445555555556666
           123456789012345678901234567890123456789012345678901234567 8901
h13B3 S1-L EIVLTQSPTTLSLSPGERATLSCRASSSVHYMYWYQQKPGQAPELLIYYTSNLAPGIP
h13B3 S2-L .......A.....................................................A.
h13B3 S3-L .......A.....................................................A.
h13B3 S4-L .......A.....................................................A.

666666667777777777888888888899999999991111111
           234567890123456789012345678901234567890000000
                                                0123456
h13B3 S1-L FSGSGSGTDFTLTISSLEPEDFAVYYCQQFTSSPYTFGGGTKVEIK
h13B3 S2-L ..............................................
h13B3 S3-L ..............S...............................
h13B3 S4-L ..............S...............................
```

Figure 13A
Heavy chain of h12B10

Kabat numbering

```
                    111111111122222222223333335 5 3333444444444455555555
           123456789012345678901234567890123452 2 6789012345678901234567
                                              ABC
h12B10 S1-H EVQLVESGGGLVKPGGSLRLSCAASGFSLSTSGMGVGWVRQAPGKGLEWLAHIWWDEKY
h12B10 S2-H ..............................................................
h12B10 S3-H ..............................................................
h12B10 S4-H .....................................R........................

566666666667777777777888 888 888889999999999 1 111111111111
           901234567890123456789012 222 345678901234567890 0 1234567890123
                                    ABC                  0A B
h12B10 S1-H YNPSLKSRFTISRDDSKNTLYLQMNSLKTEDTAVYYCARDHLAYYETMWGQGTLVTVSS
h12B10 S2-H .........................................................L.........
h12B10 S3-H ...........................................ZF.....L..................
h12B10 S4-H ...........................................MSF....L..................
```

Figure 13B

Light chain of h12B10

Kabat numbering

```
              1111111111222222222233333333334444444444555555555 6
     123456789 0123456789012345678901234567890123456789012345678 90
h12B10 S1-L  [DIQMTQSPSSLSASVGDRVTITCKASQDINKYIAWYQQKPGKAPKLLMAYPETLQPGVPS]
h12B10 S2-L   .............................................................
h12B10 S3-L   .............................................................
h12B10 S4-L   .............................................................

6666666667777777777888888888899999999991111111
              1234567890123456789012345678901234567890000000
                                                    0123456
                                                    01234567
h12B10 S1-L  [RFSGSGSGTDFTLTISSLQPEDFATYYCLQYDNLLWTFGQGTKVEIK]
h12B10 S2-L   ..............................................
h12B10 S3-L   ..............................................
h12B10 S4-L   ..............................................
```

Figure 14A

Heavy chain of h16F6

Kabat numbering

```
              1111111111222222222233333333334444444444555 5555555
     123456789 0123456789012345678901234567890123456789012 3456789
                                                          A
h16F6 S1-H  [QVQLVQSGAEVKKPGASVKVSCKASGYTFTTYWIAWVRQAPGQGLEWMGEILPGSAKTKY]
h16F6 S2-H   ...........................................................
h16F6 S3-H   ...........................................................
h16F6 S4-H   ...........................................................
h16F6 S5-H   ...........................................................

66666666667777777777888 888888889999999999111111111111
              01234567890123456789012 345678901234567890012345678 9012 3
                                     ABC
h16F6 S1-H  [NKKFKGRVTMTRDTSTSTVYMELSSLRSEDTAVYYCAVYDYGADYWGQGTTVTVSS]
h16F6 S2-H   .........................................................
h16F6 S3-H   .........................................................
h16F6 S4-H   .........................................................
h16F6 S5-H   .........................................................
```

Figure 14B

Light chain of h16F6

Kabat numbering

```
              1111111111222222222233333333334444444444555555555 6
     123456789 0123456789012345678901234567890123456789012345678 90
h16F6 S1-L  [DIQMTQSPSSLSASVGDRVTITCKASQDVYTAVAWYQQKPGKSPKLLIYSASYRFTGVPS]
h16F6 S2-L   .............................................................
h16F6 S3-L   .............................................................
h16F6 S4-L   .............................................................
h16F6 S5-L   ...................Q.........................................

6666666667777777777888888888899999999991111111
              1234567890123456789012345678901234567890000000
                                                    01234567
h16F6 S1-L  [RFSGSGSGTDFTLTISSLQPEDFATYYCQQHYSIPRTFGGGTKVEIK]
h16F6 S2-L   .L.....A.......................................
h16F6 S3-L   ..T....A.......................................
h16F6 S4-L   ..T....A......G................................
h16F6 S5-L   ..T....A......G................................
```

Figure15A
Heavy chain of h16B3-S1

```
                                   CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCAKLGGRNHDYWYFDVWGQGTTVTVSS
                                CDR3
```

Light chain of h16B3-S1

```
                            CDR1                         CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWKVPFTFGQGTKLEIK
                       CDR3
```

Figure15B
Heavy chain of h16B3-S2

```
                                   CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGRNHDYWYFDVWGQGTTVTVSS
                                CDR3
```

Light chain of h16B3-S2

```
                            CDR1                         CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWKVPFTFGQGTKLEIK
                       CDR3
```

Figure15C
Heavy chain of h16B3-S3

```
                                   CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGKNHDFWYFDVWGQGTTVTVSS
                                CDR3
```

Light chain of h16B3-S3

```
                            CDR1                         CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWKVPFTFGQGTKLEIK
                       CDR3
```

Figure 15D

Heavy chain of h16B3-S4

```
                              CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGKNHDFWYFDVWGQGTTVTVSS
                                 CDR3
```

Light chain of h16B3-S4

```
                      CDR1                          CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWRVPFTFGQGTKLEIK
                     CDR3
```

Figure 15E

Heavy chain of h16B3-S5

```
                              CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGKNRDFWYFDLWGQGTTVTVSS
                                 CDR3
```

Light chain of h16B3-S5

```
                      CDR1                          CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWKVPFTFGQGTKLEIK
                     CDR3
```

Figure 15F

Heavy chain of h16B3-S6

```
                              CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGKNRDFWYFDLWGQGTTVTVSS
                                 CDR3
```

Light chain of h16B3-S6

```
                      CDR1                          CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWRVPFTFGQGTKLEIK
                     CDR3
```

Figure15G
Heavy chain of h16B3-S7

```
                               CDR1                         CDR2
EVQLVESGGGLVQPGGSLRLSCAASGFTFSAYTMSWVRQAPGKGLEWVSDISFARDRAFYPDTVKG
RFTISRDNSKNTLYLQMNSLRAEDTAVYYCARLGGKNRDFWYFDLWGQGTTVTVSS
                               CDR3
```

Light chain of h16B3-S7

```
                          CDR1                      CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWKVPFTFGQGTKLEIK
                          CDR3
```

Figure15H
Heavy chain of h16B3-S8

```
                               CDR1                         CDR2
EVQLVESGGGLVQPGGSLRLSCAASGFTFSAYTMSWVRQAPGKGLEWVSDISFARDRAFYPDTVKG
RFTISRDNSKNTLYLQMNSLRAEDTAVYYCARLGGKNRDFWYFDLWGQGTTVTVSS
                               CDR3
```

Light chain of h16B3-S8

```
                          CDR1                      CDR2
DIVMTQSPDSLAVSLGERATINCRASESVEYYGTSLMQWYQQKPGQPPKLLIYAASNVESGVPDRFS
GSGSGTDFTLTISSLQAEDVAVYYCQQSWRVPFTFGQGTKLEIK
                          CDR3
```

Figure15I
Heavy chain of h16B3-F1

```
                               CDR1                         CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGRNHDYWYFDVWGQGTTVTVSS
                               CDR3
```

Light chain of h16B3-F1

```
                          CDR1                      CDR2
DIQMTQSPSSLSASVGDRVTITCRASESVEYYGTSLMQWYQQKPGKAPKLLIYAASNVESGVPSRFS
GSGSGTDFTLTISSLQPEDFATYYCQQSWKVPFTFGQGTKLEIK
                          CDR3
```

Figure15J
Heavy chain of h16B3-F2

```
                              CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGRNHDYWYFDVWGQGTTVTVSS
                                 CDR3
```

Light chain of h16B3-F2

```
                              CDR1                      CDR2
EIVMTQSPATLSVSPGERATLSCRASESVEYYGTSLMQWYQQKPGQAPRLLIYAASNVESGIPARFS
GSGSGTEFTLTISSLQSEDFAVYYCQQSWKVPFTFGQGTKLEIK
                         CDR3
```

Figure15K
Heavy chain of h16B3-F3

```
                              CDR1                      CDR2
EVQLVESGGGLVQPGGSLRLSCAASGFTFSGYTMSWVRQAPGKGLEWVSEISFARDRAFYPDTVKG
RFTISRDNSKNTLYLQMNSLRAEDTAVYYCARLGGRNHDYWYFDVWGQGTTVTVSS
                                 CDR3
```

Light chain of h16B3-F3

```
                              CDR1                      CDR2
EIVLTQSPGTLSLSPGERATLSCRASESVEYYGTSLMQWYQQKPGQAPRLLIYAASNVESGIPDRFS
GSGSGTDFTLTISRLEPEDFAVYYCQQSWKVPFTFGQGTKLEIK
                         CDR3
```

Figure16A
Heavy chain of h55A1-S1

```
                              CDR1                      CDR2
QVQLVQSGSELKKPGASVKVSCKASGYTFTNYGMNWVRQAPGQGLEWMGWINTYSGVPTYAGDFKG
RFVFSLDTSVSTAYLQISSLKAEDTAVYYCARRGYYGRRYFDVWGKGTTVTVSS
                                 CDR3
```

Light chain of h55A1-S1

```
                              CDR1                      CDR2
DIVLTQSPASLAVSPGQRATITCKASQSVDYDVDSYMHWYQQKPGQPPKLLIYAASNLASGVPARFS
GSGSGTDFTLTINPVEANDTANYYCQQTIEDPPTFGGGTKVEIK
                         CDR3
```

Figure16B
Heavy chain of h55A1-S2

CDR1                    CDR2
QVQLVQSGSELKKPGASVKVSCKASGYTFTNYGLNWVRQAPGQGLEWMGWINTYSGVPTYAGDFKG
RFVFSLDTSVSTAYLQISSLKAEDTAVYYCARRGYYGRRFFDVWGKGTTVTSS
                                   CDR3

Light chain of h55A1-S2

CDR1                        CDR2
DIVLTQSPASLAVSPGQRATITCKASQSVDYDVDSYMHWYQQKPGQPPKLLIYAASNLASGVPARFS
GSGSGTDFTLTINPVEANDTANYYCQQTIEDPPTFGGGTKVEIK
                                 CDR3

Figure16C
Heavy chain of h55A1-S3

CDR1                    CDR2
QVQLVQSGSELKKPGASVKVSCKASGYTFTNYGLNWVRQAPGQGLEWMGWINTYSGVPTYAGDFKG
RFVFSLDTSVSTAYLQISSLKAEDTAVYYCARRGYYGRRFFDVWGKGTTVTVSS
                                   CDR3

Light chain of h55A1-S3

CDR1                        CDR2
DIVLTQSPASLAVSPGQRATITCKASQSVDYDVDSYMHWYQQKPGQPPKLLIYAASNLASGVPARFS
GSGSGTDFTLTINPVEANDTANYYCQNTIEDPPTFGGGTKVEIK
                                 CDR3

Figure16D
Heavy chain of h55A1-S4

CDR1                    CDR2
QVQLVQSGSELKKPGASVKVSCKASGYTFTNYAMNWVRQAPGQGLEWMGWINTYSGVGTYAGDFKG
RFVFSLDTSVSTAYLQISSLKAEDTAVYYCARRGFYGRRFFDVWGKGTTVTVSS
                                   CDR3

Light chain of h55A1-S4

CDR1                        CDR2
DIVLTQSPASLAVSPGQRATITCKASQSVDYDVDSYMHWYQQKPGQPPKLLIYAASNLASGVPARFS
GSGSGTDFTLTINPVEANDTANYYCQQTIEDPPTFGGGTKVEIK
                                 CDR3

Figure16E
Heavy chain of h55A1-S5

```
                                CDR1                        CDR2
QVQLVQSGSELKKPGASVKVSCKASGYTFTNYAMNWVRQAPGQGLEWMGWINTYSGVGTYAGDFKG
RFVFSLDTSVSTAYLQISSLKAEDTAVYYCARRGFYGRRFFDVWGKGTTVTVSS
                                CDR3
```

Light chain of h55A1-S5

```
                    CDR1                            CDR2
DIVLTQSPASLAVSPGQRATITCKASQSVDYDVDSYMHWYQQKPGQPPKLLIYAASNLASGVPARFS
GSGSGTDFTLTINPVEANDTANYYCQNTIEDPPTFGGGTKVEIK
                    CDR3
```

Figure16F
Heavy chain of h55A1-S6

```
                                CDR1                        CDR2
QVQLVQSGSELKKPGASVKVSCKASGYTFTNYALNWVRQAPGQGLEWMGWINTYSGVGTYAGEFKG
RFVFSLDTSVSTAYLQISSLKAEDTAVYYCARRGFYGRRFFDVWGKGTTVTVSS
                                CDR3
```

Light chain of h55A1-S6

```
                    CDR1                            CDR2
DIVLTQSPASLAVSPGQRATITCKASQSVDYDVDSYMHWYQQKPGQPPKLLIYAASNLASGVPARFS
GSGSGTDFTLTINPVEANDTANYYCQQTIEDPPTFGGGTKVEIK
                    CDR3
```

Figure16G
Heavy chain of h55A1-S7

```
                                CDR1                        CDR2
QVQLVQSGSELKKPGASVKVSCKASGYTFTNYALNWVRQAPGQGLEWMGWINTYSGVGTYAGEFKG
RFVFSLDTSVSTAYLQISSLKAEDTAVYYCARRGFYGRRFFDVWGKGTTVTVSS
                                CDR3
```

Light chain of h55A1-S7

```
                    CDR1                            CDR2
DIVLTQSPASLAVSPGQRATITCKASQSVDYDVDSYMHWYQQKPGQPPKLLIYAASNLASGVPARFS
GSGSGTDFTLTINPVEANDTANYYCQNTIEDPPTFGGGTKVEIK
                    CDR3
```

Figure16H
Heavy chain of h55A1-F1

```
                             CDR1                          CDR2
QVQLVQSGSELKKPGASVKVSCKASGYTFTNYGMNWVRQAPGQGLEWMGWINTYSGVPTYAGDFKG
RFVFSLDTSVSTAYLQISSLKAEDTAVYYCARRGYYGRRYFDVWGKGTTVTVSS
                                   CDR3
```

Light chain of h55A1-F1

```
                         CDR1                          CDR2
DIQLTQSPSSLSASVGDRVTITCKASQSVDYDVDSYMHWYQQKPGKAPKLLIYAASNLASGVPSRFS
GSGSGTDFTFTISSLQPEDIATYYCQQTIEDPPTFGGGTKVEIK
                         CDR3
```

Figure16I
Heavy chain of h55A1-F2

```
                             CDR1                          CDR2
QVQLVQSGAEVKKPGASVKVSCKASGYTFTNYGMNWVRQAPGQGLEWMGWINTYSGVPTYAGDFKG
RVTMTTDTSTSTAYMELRSLRSDDTAVYYCARRGYYGRRYFDVWGKGTTVTVSS
                                   CDR3
```

Light chain of h55A1-F2

```
                         CDR1                          CDR2
EIVMTQSPATLSVSPGERATLSCKASQSVDYDVDSYMHWYQQKPGQAPRLLIYAASNLASGIPARFS
GSGSGTEFTLTISSLQSEDFAVYYCQQTIEDPPTFGGGTKVEIK
                         CDR3
```

Figure16J
Heavy chain of h55A1-F3

```
                             CDR1                          CDR2
QVQLVQSGAEVKKPGASVKVSCKASGYTFTNYGMNWVRQAPGQGLEWMGWINTYSGVPTYAGDFKG
RVTMTTDTSTSTAYMELRSLRSDDTAVYYCARRGYYGRRYFDVWGKGTTVTVSS
                                   CDR3
```

Light chain of h55A1-F3

```
                         CDR1                          CDR2
DIQLTQSPSSLSASVGDRVTITCKASQSVDYDVDSYMHWYQQKPGKAPKLLIYAASNLASGVPSRFS
GSGSGTDFTLTISSLQPEDFATYYCQQTIEDPPTFGGGTKVEIK
                         CDR3
```

Figure 16K
Heavy chain of h55A1-F4

```
                              CDR1                         CDR2
QVQLVQSGAEVKKPGASVKVSCKASGYTFTNYGMNWVRQAPGQGLEWMGWINTYSGVPTYAGDFKG
RVTMTTDTSTSTAYMELRSLRSDDTAVYYCARRGYYGRRYFDVWGKGTTVTVSS
                                      CDR3
```

Light chain of h55A1-F4

```
                              CDR1                         CDR2
EIVLTQSPGTLSLSPGERATLSCKASQSVDYDVDSYMHWYQQKPGQAPRLLIYAASNLASGIPDRFS
GSGSGTDFTLTISRLEPEDFAVYYCQQTIEDPPTFGGGTKVEIK
                        CDR3
```

Figure 16L
Heavy chain of h55A1-F5

```
                              CDR1                         CDR2
QVQLVQSGAEVKKPGASVKVSCKASGYTFTNYGMNWVRQAPGQGLEWMGWINTYSGVPTYAGDFKG
RFTFTLDTSTSTAYMELSSLRSEDTAVYYCARRGYYGRRYFDVWGKGTTVTVSS
                                      CDR3
```

Light chain of h55A1-F5

```
                              CDR1                         CDR2
DIQLTQSPSSLSASVGDRVTITCKASQSVDYDVDSYMHWYQQKPGKAPKLLIYAASNLASGVPSRFS
GSGSGTDFTLTISSLQPEDFATYYCQQTIEDPPTFGGGTKVEIK
                        CDR3
```

Figure 16M
Heavy chain of h55A1-F6

```
                              CDR1                         CDR2
QVQLVQSGAEVKKPGASVKVSCKASGYTFTNYGMNWVRQAPGQGLEWMGWINTYSGVPTYAGDFKG
RFTFTLDTSTSTAYMELSSLRSEDTAVYYCARRGYYGRRYFDVWGKGTTVTVSS
                                      CDR3
```

Light chain of h55A1-F6

```
                              CDR1                         CDR2
EIVMTQSPATLSVSPGERATLSCKASQSVDYDVDSYMHWYQQKPGQAPRLLIYAASNLASGIPARFS
GSGSGTEFTLTISSLQSEDFAVYYCQQTIEDPPTFGGGTKVEIK
                        CDR3
```

Figure17A
Heavy chain of h53A11-S1

```
                                        CDR1                    CDR2
QVQLVQSGAEVKKPGASVKVSCKASGYTFTDYTMHWVRQAPGQRLEWMGGINPYYGGTTYNEKFKD
RVTITRDTSASTAYMELSSLRSEDTAVYYCAKGDYYGGSYNYWGQGTTVTVSS
                                        CDR3
```

Light chain of h53A11-S1

```
                         CDR1                      CDR2
EIVMTQSLATLSVSPGERATLSCRASQDISNSLHWYQQKPGQAPRLLIKYASQSISGIPARFSGSGS
GTEFTLTISSLQSEDFAVYYCQQSNSWPYTFGQGTKLEIK
                      CDR3
```

Figure17B
Heavy chain of h53A11-S2

```
                                        CDR1                    CDR2
QVQLVQSGAEVKKPGASVKVSCKASGYTFTDYTMHWVRQAPGQRLEWMGGINPYYGGTTYNEKFKD
RVTITRDTSASTAYMELSSLRSEDTAVYYCAKGDYYGGSYNYWGQGTTVTVSS
                                        CDR3
```

Light chain of h53A11-S2

```
                         CDR1                      CDR2
EIVMTQSLATLSVSPGERATLSCRASQDISNSLHWYQQKPGQAPRLLIYYASQSISGIPARFSGSGS
GTEFTLTISSLQSEDFAVYYCQQSNSWPYTFGQGTKLEIK
                      CDR3
```

Figure17C
Heavy chain of h53A11-S3

```
                                        CDR1                    CDR2
QVQLVQSGAEVKKPGASVKVSCKASGYTFTDYTMHWVRQAPGQRLEWMGGINPYYGGTTYNEKFKD
RVTITRDTSASTAYMELSSLRSEDTAVYYCAKGDYYGGSYNYWGQGTTVTVSS
                                        CDR3
```

Light chain of h53A11-S3

```
                         CDR1                      CDR2
EIVMTQSPATLSVSPGERATLSCRASQDISNSLHWYQQKPGQAPRLLIKYASQSISGIPARFSGSGS
GTEFTLTISSLQSEDFAVYYCQQSNSWPYTFGQGTKLEIK
                      CDR3
```

Figure 17D
Heavy chain of h53A11-S4

CDR1                     CDR2
QVQLVQSGAEVKKPGASVKVSCKASGYTFT<u>DYTMH</u>WVRQAPGQRLEWMG<u>GINPYYGGTTYNEKFKD</u>
RVTITRDTSASTAYMELSSLRSEDTAVYYCAR<u>GDYYGGSYNYW</u>GQGTTVTVSS
                                    CDR3

Light chain of h53A11-S4

CDR1                    CDR2
EIVMTQSPATLSVSPGERATLSC<u>RASQDISNSLH</u>WYQQKPGQAPRLLIK<u>YASQSIS</u>GIPARFSGSGS
GTEFTLTISSLQSEDFAVYYC<u>QQSNSWPYT</u>FGQGTKLEIK
                      CDR3

Figure 18A
Heavy chain of h23H8-S1

CDR1                   CDR2
QVQLVQSGAEVKKPGASVKVSCKASGYTFT<u>DNTIH</u>WVRQAPGQGLEWMG<u>HINPYYGGTNNNEKFKD</u>
RVTMTRDTSISTAYMELSRLRSDDTAVYYCAR<u>KGIYYSSPFDY</u>WGQGTTVTVSS
                                  CDR3

Light chain of h23H8-S1

CDR1                    CDR2
DIQMTQSPSSLSASVGDRVTITC<u>RASQDINNYLN</u>WYQQKPGKAPKLLIY<u>YTSKLHS</u>GVPSRFSGSGS
GTDFTLTISSLQPEDFATYYC<u>QQGNTLPFT</u>FGQGTKLEIK
                      CDR3

Figure 18B
Heavy chain of h23H8-S2

CDR1                   CDR2
QVQLVQSGAEVKKPGASVKVSCKASGYTFT<u>DNTIH</u>WVRQAPGQGLEWMG<u>HINPYYGGTNNNEKFKD</u>
RVTMTRDTSISTAYMELSRLRSDDTAVYYCAR<u>KGIYYSSPFDY</u>WGQGTTVTVSS
                                  CDR3

Light chain of h23H8-S2

CDR1                    CDR2
DIQMTQSPSSLSASVGDRVTITC<u>RASQDINNYLN</u>WYQQKPGKAPKLLI<u>SYTSKLHS</u>GVPSRFSGSGS
GTDFTLTISSLQREDFATYYC<u>QQGNTLPFT</u>FGQGTKLEIK
                      CDR3

Figure 18C
Heavy chain of h23H8-S3

CDR1                   CDR2
QVQLVQSGAEVKKPGASVKVSCKASGYTFT<u>DNTIH</u>WVRQAPGQGLEWMG<u>HINPYYGGTNNNEKFKD</u>
RVTMTRDTSISTAYMELSRLRSDDTAVYYCAR<u>KGIYYSSPFDY</u>WGQGTTVTVSS
                                  CDR3

Light chain of h23H8-S3

CDR1                    CDR2
DIQMTQSPSSLSASVGDRVTITC<u>RASQDINNYLN</u>WYQQKPGKAPKLLI<u>SYTSKLHS</u>GVPSRFSGSGS
GTDFTLTISSLQPEDFATYYC<u>QQGNTLPFT</u>FGQGTKLEIK
                      CDR3

Figure19A
Heavy chain of h13B3-S1

```
                              CDR1                    CDR2
QVQLVQSGAEVKKPGASVKVSCKASGYTFTEYTMHWVRQAPGQGLEWMGSINPYYGGTSYNEKFKD
RVTMTRDTSTSTVYMELSSLRSEDTAVYYCARYGNYVGYFDYWGQGTTVTVSS
                              CDR3
```

Light chain of h13B3-S1

```
                          CDR1                  CDR2
EIVLTQSPGTLSLSPGERATLSCRASSSVHYMYWYQQKPGQAPRLLIYYTSNLAPGIPDRFSGSGSG
TDFTLTISRLEPEDFAVYYCQQFTSSPYTFGGGTKVEIK
                   CDR3
```

Figure19B
Heavy chain of h13B3-S2

```
                              CDR1                    CDR2
QVQLVQSGAEVKKPGASVKVSCKASGYTFTEYTMHWVRQAPGQGLEWMGSINPYYGGTSYNEKFKD
RVTSTRDTSISTAYMELSRLRSDDTVVYYCARYGNYVGYFDYWGQGTTVTVSS
                              CDR3
```

Light chain of h13B3-S2

```
                          CDR1                  CDR2
EIVLTQSPGTLSLSPGERATLSCRASSSVHYMYWYQQKPGQAPRLLIYYTSNLAPGIPDRFSGSGSG
TDFTLTISRLEPEDFAVYYCQQFTSSPYTFGGGTKVEIK
                   CDR3
```

Figure19C
Heavy chain of h13B3-S3

```
                              CDR1                    CDR2
QVQLVQSGAEVKKPGASVKVSCKASGYTFTEYTMHWVRQAPGQGLEWMGSINPYYGGTSYNEKFKD
RVTMTRDTSTSTVYMELSSLRSEDTAVYYCARYGNYVGYFDYWGQGTTVTVSS
                              CDR3
```

Light chain of h13B3-S3

```
                          CDR1                  CDR2
EIVLTQSPATLSLSPGERATLSCRASSSVHYMYWYQQKPGQAPRLLIYYTSNLAPGIPARFSGSGSG
TDFTLTISSLEPEDFAVYYCQQFTSSPYTFGGGTKVEIK
                   CDR3
```

Figure19D
Heavy chain of h13B3-S4

```
                                  CDR1                       CDR2
QVQLVQSGAEVKKPGASVKVSCKASGYTFTEYTMHWVRQAPGQGLEWMGSINPYYGGTSYNEKFKD
RVTSTRDTSISTAYMELSRLRSDDTVVYYCARYGNYVGYFDYWGQGTTVTVSS
                                    CDR3
```

Light chain of h13B3-S4

```
                       CDR1                     CDR2
EIVLTQSPATLSLSPGERATLSCRASSSVHYMYWYQQKPGQAPRLLIYYTSNLAPGIPARFSGSGSG
TDFTLTISSLEPEDFAVYYCQQFTSSPYTFGGGTKVEIK
                     CDR3
```

Figure20A
Heavy chain of h12B10-S1

```
                                  CDR1                       CDR2
EVQLVESGGGLVKPGGSLRLSCAASGFSLSTSGMGVGWVRQAPGKGLEWLAHIWWNDEKYYNPSLKS
RFTISRDDSKNTLYLQMNSLKTEDTAVYYCARDHLAYYFDVWGQGTLVTVSS
                                    CDR3
```

Light chain of h12B10-S1

```
                         CDR1                       CDR2
DIQMTQSPSSLSASVGDRVTITCKASQDINKYIAWYQQKPGKAPKLLMAYPFTLQPGVPSRFSGSGS
GTDFTLTISSLQPEDFATYYCLQYDNLLWTFGQGTKVEIK
                      CDR3
```

Figure20B
Heavy chain of h12B10-S2

```
                                  CDR1                       CDR2
EVQLVESGGGLVKPGGSLRLSCAASGFSLSTSGMGVGWVRQAPGKGLEWLAHIWWNDEKYYNPSLKS
RFTISRDDSKNTLYLQMNSLKTEDTAVYYCARDHLAFYFDLWGQGTLVTVSS
                                    CDR3
```

Light chain of h12B10-S2

```
                         CDR1                       CDR2
DIQMTQSPSSLSASVGDRVTITCKASQDINKYIAWYQQKPGKAPKLLMAYPFTLQPGVPSRFSGSGS
GTDFTLTISSLQPEDFATYYCLQYDNLLWTFGQGTKVEIK
                      CDR3
```

Figure 20C
Heavy chain of h12B10-S3

```
                                          CDR1                         CDR2
EVQLVESGGGLVKPGGSLRLSCAASGFSLSTSGMGVGWVRQAPGKGLEWLAHIWWNDEKYYNPSLKS
RFTISRDDSKNTLYLQMNSLKTEDTAVYYCARDHLAFFFDLWGQGTLVTVSS
                                  CDR3
```

Light chain of h12B10-S3

```
                           CDR1                        CDR2
DIQMTQSPSSLSASVGDRVTITCKASQDINKYIAWYQQKPGKAPKLLMAYPFTLQPGVPSRFSGSGS
GTDFTLTISSLQPEDFATYYCLQYDNLLWTFGQGTKVEIK
                      CDR3
```

Figure 20D
Heavy chain of h12B10-S4

```
                                          CDR1                         CDR2
EVQLVESGGGLVKPGGSLRLSCAASGFSLSSSGMGVGWVRQAPGKGLEWLAHIWWNDEKYYNPSLKS
RFTISRDDSKNTLYLQMNSLKTEDTAVYYCARDHLVFFFDLWGQGTLVTVSS
                                  CDR3
```

Light chain of h12B10-S4

```
                           CDR1                        CDR2
DIQMTQSPSSLSASVGDRVTITCKASQDINKYIAWYQQKPGKAPKLLMAYPFTLQPGVPSRFSGSGS
GTDFTLTISSLQPEDFATYYCLQYDNLLWTFGQGTKVEIK
                      CDR3
```

Figure 21A
Heavy chain of h16F6-S1

```
                                       CDR1                         CDR2
QVQLVQSGAEVKKPGASVKVSCKASGYTFTTYWIAWVRQAPGQGLEWMGEILPGSAKTKYNKKFKG
RVTMTRDTSTSTVYMELSSLRSEDTAVYYCAVYDYGADYWGQGTTVTVSS
                               CDR3
```

Light chain of h16F6-S1

```
                           CDR1                       CDR2
DIQMTQSPSSLSASVGDRVTITCKASQDVYTAVAWYQQKPGKSPKLLIYSASYRFTGVPSRFSGSGS
GTDFTLTISSLQPEDFATYYCQQHYSIPRTFGGGTKVEIK
                      CDR3
```

Figure 21B
Heavy chain of h16F6-S2

```
                              CDR1                       CDR2
QVQLVQSGAEVKKPGASVKVSCKASGYTFTTYWIAWVRQAPGQGLEWMGEILPGSAKTKYNKKFKG
RVTMTRDTSTSTVYMELSSLRSEDTAVYYCAVYDYGADYWGQGTTVTVSS
                                     CDR3
```

Light chain of h16F6-S2

```
                        CDR1                       CDR2
DIQMTQSPSSLSASVGDRVTITCKASQDVYTAVAWYQQKPGKSPKLLIYSASYRFTGVPSRFSGSGA
GTDFTLTISSLQPEDFATYYCQQHYSIPRTFGGGTKVEIK
                      CDR3
```

Figure 21C
Heavy chain of h16F6-S3

```
                              CDR1                       CDR2
QVQLVQSGAEVKKPGASVKVSCKASGYTFTTYWIAWVRQAPGQGLEWMGEILPGSAKTKYNKKFKG
RVTMTRDTSTSTVYMELSSLRSEDTAVYYCAVYDYGADYWGQGTTVTVSS
                                     CDR3
```

Light chain of h16F6-S3

```
                        CDR1                       CDR2
DIQMTQSPSSLSASVGDRVTITCKASQDVYTAVAWYQQKPGKSPKLLIYSASYRFTGVPSRFTGSGA
GTDFTLTISSLQPEDFATYYCQQHYSIPRTFGGGTKVEIK
                      CDR3
```

Figure 21D
Heavy chain of h16F6-S4

```
                              CDR1                       CDR2
QVQLVQSGAEVKKPGASVKVSCKASGYTFTTYWIAWVRQAPGQGLEWMGEILPGSAKTKYNKKFKG
RVTMTRDTSTSTVYMELSSLRSEDTAVYYCAVYDYGADYWGQGTTVTVSS
                                     CDR3
```

Light chain of h16F6-S4

```
                        CDR1                       CDR2
DIQMTQSPSSLSASVGDRVTITCKASQDVYTAVAWYQQKPGKSPKLLIYSASYRFTGVPSRFTGSGA
GTDFTFTISSLQPEDFATYYCQQHYSIPRTFGGGTKVEIK
                      CDR3
```

Figure21E

Heavy chain of h16F6-S5

```
                                CDR1                        CDR2
QVQLVQSGAEVKKPGASVKVSCKASGYTFTTYWIAWVRQAPGQGLEWMGEILPGSAKTKYNKKFKG
RVTMTRDTSTSTVYMELSSLRSEDTAVYYCAVYDYGADYWGQGTTVTVSS
                                    CDR3
```

Light chain of h16F6-S5

```
                                CDR1                        CDR2
DIQMTQSPSSLSASVGDRVSITCKASQDVYTAVAWYQQKPGKSPKLLIYSASYRFTGVPSRFTGSGA
GTDFTFTISSLQPEDFATYYCQQHYSIPRTFGGGTKVEIK
                  CDR3
```

# HUMANIZED MONOCLONAL ANTIBODY, INHIBITING THE ENZYMATIC ACTIVITY OF VASCULAR ENDOTHELIAL LIPASE

CROSS REFERENCE TO RELATED APPLICATIONS

The present application is a continuation application of International Application No. PCT/JP2015/075668, filed on Sep. 10, 2015, which claims priority to Japanese Patent Application No. 2014-184710, filed on Sep. 11, 2014. The contents of these applications are incorporated herein by reference in their entirety.

REFERENCE TO SEQUENCE LISTING SUBMITTED VIA EFS-WEB

This application includes an electronically submitted sequence listing in .txt format. The .txt file contains a sequence listing entitled "2018-12-02_0032-0329PUS1_ST25.txt" created on Dec. 2, 2018 and is 93,614 bytes in size. The sequence listing contained in this .txt file is part of the specification and is hereby incorporated by reference herein in its entirety.

TECHNICAL FIELD

The present invention relates to a humanized monoclonal antibody that inhibits the enzymatic activity of vascular endothelial lipase (hereinafter, referred to also EL) and pharmaceutical compositions containing the same. More specifically, the present invention relates to a humanized monoclonal antibody that selectively inhibits the enzymatic activity of EL, or an antibody fragment thereof, and a pharmaceutical composition containing the same.

BACKGROUND ART

EL is a phospholipase that belongs to triglyceride lipase (hereinafter, referred to TG) family (non-patent literature: 1). Human EL consists of 500 amino acids (NCBI Accession number NP_006024.1, SEQ ID NO: 1). ELs of non-human mammal include rabbit EL (NCBI Accession number NO_001182567, SEQ ID NO: 2), cynomolgus EL (NCBI Accession No. EHH61805.1), baboon EL (NCBI Accession No. XP_003914420.1) and mouse EL (NCBI Accession No. NP_034850.3). Lipoprotein lipase (hereinafter, referred to LPL) and hepatic lipase (hereinafter, referred to HL) is contained by TG family.

The analysis of EL knockout mouse and EL transgenic mouse revealed that EL relates to HDL cholesterol (hereinafter, referred to HDL-c) metabolism by its strong phospholipase activity, and have been a focus as a factor which controls HDL-c level in blood (non-patent literature: 2). It has been well-known that there is a negative correlation between coronary artery disease (hereinafter, referred to CAD) and HDL-c level in blood. HDL-c shows anti-atherogenic effect through antioxidant effect, anti-inflammatory effect and reverse cholesterol transport and so on, low HDL-c emia is recognized as one of the risk factor of CAD. Therefore, EL inhibitor could be a therapeutic agent for CAD through increasing HDL-c in blood. In fact, it was reported that lesion mouse of EL knockout increased HDL-c and decreased atherosclerotic lesions (non-patent literature: 3).

These findings indicate that a selective EL inhibitor is useful as therapeutic agent for abnormality of lipid metabolism and arteriosclerosis.

A selective inhibition of EL is useful as therapeutic agent for abnormality of lipid metabolism and arteriosclerosis, so a production of EL antibodies which inhibit EL activity is one of the important approaches. So far, it has been reported that a rabbit polyclonal antibody which inhibits EL activity was prepared, HDL-c level in mouse blood increased after administrating of the antibody (non-patent literature: 4).

Polyclonal antibodies recognize various regions of EL and do not have a high selectivity against EL. Also, it is impossible to use rabbit anti-EL polyclonal antibodies having high immunogenicity to human as therapeutic agent for chronic diseases because therapeutic agents for chronic diseases such as the abnormality of lipid metabolism and arteriosclerosis related to EL have to be administrated for a long term. Moreover, it is difficult to manipulate immunogenicity of polyclonal antibodies.

By these circumstances, a monoclonal antibody inhibiting selectively the enzymatic activity of EL is awaited.

Non-patent document 1: Nature Genetics., 1999, vol. 21, p. 424
Non-patent document 2: TCM., 2004, vol. 14(5), p. 202-206
Non-patent document 3: The Journal of Biological Chemistry., 2004, vol. 279, No. 43, 22 p. 45085-45092
Non-patent document 4: J din Invest., 2003, Vol. 111(3), p. 357

SUMMARY OF THE INVENTION

Problem to be Solved by the Invention

An objective of the present invention is to provide a humanized monoclonal antibody that selectively inhibits enzyme activity of EL, or an antibody fragment thereof, and a pharmaceutical composition containing the same.

Means for Solving the Problem

As a result of diligent efforts, the present inventors have succeeded in finding a humanized monoclonal antibody that selectively inhibits the enzymatic activity of EL.

To be more specific, the present invention relates to:
(1) A humanized monoclonal antibody that inhibits the enzymatic activity of vascular endothelial lipase or an antibody fragment thereof, wherein it recognizes amino acid residues at positions of 1 to 157 in the amino acid sequence of SEQ ID NO: 1.
(2) The humanized monoclonal antibody or the antibody fragment thereof of (1), wherein it recognizes amino acid residues at positions of 50 to 100 in the amino acid sequence of SEQ ID NO: 1.
(3) The humanized monoclonal antibody or the antibody fragment thereof of (1) or (2), wherein it recognizes arginine at position 50, asparagine at position 52, arginine at position 54, aspartic acid at position 58, glutamic acid at position 60, histidine at position 61, glycine at position 63, tyrosine at position 65 or asparagine at position 100 in the amino acid sequence of SEQ ID NO: 1.
(4) The humanized monoclonal antibody or the antibody fragment thereof of (1) or (2), wherein it recognizes arginine at position 50, glutamic acid at position 60, histidine at position 61, tyrosine at position 65 or asparagine at position 100 in the amino acid sequence of SEQ ID NO: 1.

(5) The humanized monoclonal antibody or the antibody fragment thereof of (1) or (2), wherein it recognizes tyrosine at position 65 in the amino acid sequence of SEQ ID NO: 1.

(6) A humanized monoclonal antibody that inhibits the enzymatic activity of vascular endothelial lipase or an antibody fragment thereof, wherein it recognizes amino acid residues at positions of 202 to 305 in the amino acid sequence of SEQ ID NO: 1.

(7) The humanized monoclonal antibody or the antibody fragment thereof of (6), wherein it recognizes amino acid residues at positions of 220 to 273 in the amino acid sequence of SEQ ID NO: 1.

(8) The humanized monoclonal antibody or the antibody fragment thereof of (6) or (7), wherein it recognizes histidine at position 220, threonine at position 221, tyrosine at position 222, threonine at position 223, arginine at position 224, phenylalanine at position 226, glycine at position 227, glycine at position 231, isoleucine at position 232, glutamine at position 233, methionine at position 234, aspartic acid at position 240, tyrosine at position 242, proline at position 243, asparagine at position 244, glycine at position 246, glutamine at position 249, proline at position 250, glycine at position 251, leucine at position 254, leucine at position 258, tyrosine at position 263, valine at position 269 or glutamic acid at position 273 in the amino acid sequence of SEQ ID NO: 1.

(9) The humanized monoclonal antibody or the antibody fragment thereof of (6) or (7), wherein it recognizes histidine at position 220, threonine at position 221, aspartic acid at position 240, tyrosine at position 242, proline at position 243, asparagine at position 244, glycine at position 246, glutamine at position 249, proline at position 250 or glycine at position 251 in the amino acid sequence of SEQ ID NO: 1.

(10) The humanized monoclonal antibody or the antibody fragment thereof of (6) or (7), wherein it recognizes histidine at position 220, threonine at position 221, aspartic acid at position 240, tyrosine at position 242, proline at position 243, asparagine at position 244, glycine at position 246, glutamine at position 249, proline at position 250 and glycine at position 251 in the amino acid sequence of SEQ ID NO: 1.

(11) The humanized monoclonal antibody or the antibody fragment thereof of any one of (1) to (10), wherein it inhibits the enzymatic activity of vascular endothelial lipase with an IC50 of 10 nM or less.

(12) The humanized monoclonal antibody or the antibody fragment thereof of (11), wherein it inhibits the enzymatic activity of vascular endothelial lipase with an IC50 of 5 nM or less.

(13) The humanized monoclonal antibody or the antibody fragment thereof of (11), wherein it inhibits the enzymatic activity of vascular endothelial lipase with an IC50 of 2 nM or less.

(14) A humanized monoclonal antibody or an antibody fragment thereof, selected from the group of 1) A humanized monoclonal antibody or an antibody fragment thereof, having
   a heavy chain variable region including three CDRs having the amino acid sequence of SEQ ID NO: 2, the amino acid sequence of SEQ ID NO: 3 and the amino acid sequence of SEQ ID NO: 4, and
   a light chain variable region including three CDRs having the amino acid sequence of SEQ ID NO: 5, the amino acid sequence of SEQ ID NO: 6 and the amino acid sequence of SEQ ID NO: 7.

5) A humanized monoclonal antibody or an antibody fragment thereof, having
   a heavy chain variable region including three CDRs having the amino acid sequence of SEQ ID NO: 2, the amino acid sequence of SEQ ID NO: 3 and the amino acid sequence of SEQ ID NO: 8, and
   a light chain variable region including three CDRs having the amino acid sequence of SEQ ID NO: 5, the amino acid sequence of SEQ ID NO: 6 and the amino acid sequence of SEQ ID NO: 7.

9) A humanized monoclonal antibody or an antibody fragment thereof, having
   a heavy chain variable region including three CDRs having the amino acid sequence of SEQ ID NO: 2, the amino acid sequence of SEQ ID NO: 3 and the amino acid sequence of SEQ ID NO: 8, and
   a light chain variable region including three CDRs having the amino acid sequence of SEQ ID NO: 5, the amino acid sequence of SEQ ID NO: 6 and the amino acid sequence of SEQ ID NO: 9.

13) A humanized monoclonal antibody or an antibody fragment thereof, having
   a heavy chain variable region including three CDRs having the amino acid sequence of SEQ ID NO: 2, the amino acid sequence of SEQ ID NO: 3 and the amino acid sequence of SEQ ID NO: 10, and
   a light chain variable region including three CDRs having the amino acid sequence of SEQ ID NO: 5, the amino acid sequence of SEQ ID NO: 6 and the amino acid sequence of SEQ ID NO: 7.

17) A humanized monoclonal antibody or an antibody fragment thereof, having
   a heavy chain variable region including three CDRs having the amino acid sequence of SEQ ID NO: 2, the amino acid sequence of SEQ ID NO: 3 and the amino acid sequence of SEQ ID NO: 10, and
   a light chain variable region including three CDRs having the amino acid sequence of SEQ ID NO: 5, the amino acid sequence of SEQ ID NO: 6 and the amino acid sequence of SEQ ID NO: 9.

21) A humanized monoclonal antibody or an antibody fragment thereof, having
   a heavy chain variable region including three CDRs having the amino acid sequence of SEQ ID NO: 11, the amino acid sequence of SEQ ID NO: 12 and the amino acid sequence of SEQ ID NO: 10, and
   a light chain variable region including three CDRs having the amino acid sequence of SEQ ID NO: 5, the amino acid sequence of SEQ ID NO: 6 and the amino acid sequence of SEQ ID NO: 7.

25) A humanized monoclonal antibody or an antibody fragment thereof, having
   a heavy chain variable region including three CDRs having the amino acid sequence of SEQ ID NO: 11, the amino acid sequence of SEQ ID NO: 12 and the amino acid sequence of SEQ ID NO: 10, and
   a light chain variable region including three CDRs having the amino acid sequence of SEQ ID NO: 5, the amino acid sequence of SEQ ID NO: 6 and the amino acid sequence of SEQ ID NO: 9.

29) A humanized monoclonal antibody or an antibody fragment thereof, having
   a heavy chain variable region including three CDRs having the amino acid sequence of SEQ ID NO: 13, the amino acid sequence of SEQ ID NO: 14 and the amino acid sequence of SEQ ID NO: 15, and a light chain variable region including three CDRs having the amino acid sequence of SEQ ID NO: 16, the amino acid sequence of SEQ ID NO: 17 and the amino acid sequence of SEQ ID NO: 18.

33) A humanized monoclonal antibody or an antibody fragment thereof, having
a heavy chain variable region including three CDRs having the amino acid sequence of SEQ ID NO: 19, the amino acid sequence of SEQ ID NO: 14 and the amino acid sequence of SEQ ID NO: 20, and
a light chain variable region including three CDRs having the amino acid sequence of SEQ ID NO: 16, the amino acid sequence of SEQ ID NO: 17 and the amino acid sequence of SEQ ID NO: 18.

37) A humanized monoclonal antibody or an antibody fragment thereof, having
a heavy chain variable region including three CDRs having the amino acid sequence of SEQ ID NO: 19, the amino acid sequence of SEQ ID NO: 14 and the amino acid sequence of SEQ ID NO: 20, and
a light chain variable region including three CDRs having the amino acid sequence of SEQ ID NO: 16, the amino acid sequence of SEQ ID NO: 17 and the amino acid sequence of SEQ ID NO: 21.

41) A humanized monoclonal antibody or an antibody fragment thereof, having
a heavy chain variable region including three CDRs having the amino acid sequence of SEQ ID NO: 22, the amino acid sequence of SEQ ID NO: 23 and the amino acid sequence of SEQ ID NO: 24, and
a light chain variable region including three CDRs having the amino acid sequence of SEQ ID NO: 16, the amino acid sequence of SEQ ID NO: 17 and the amino acid sequence of SEQ ID NO: 18.

45) A humanized monoclonal antibody or an antibody fragment thereof, having
a heavy chain variable region including three CDRs having the amino acid sequence of SEQ ID NO: 22, the amino acid sequence of SEQ ID NO: 23 and the amino acid sequence of SEQ ID NO: 24, and
a light chain variable region including three CDRs having the amino acid sequence of SEQ ID NO: 16, the amino acid sequence of SEQ ID NO: 17 and the amino acid sequence of SEQ ID NO: 21.

49) A humanized monoclonal antibody or an antibody fragment thereof, having
a heavy chain variable region including three CDRs having the amino acid sequence of SEQ ID NO: 25, the amino acid sequence of SEQ ID NO: 106 and the amino acid sequence of SEQ ID NO: 24, and
a light chain variable region including three CDRs having the amino acid sequence of SEQ ID NO: 16, the amino acid sequence of SEQ ID NO: 17 and the amino acid sequence of SEQ ID NO: 18.

53) A humanized monoclonal antibody or an antibody fragment thereof, having
a heavy chain variable region including three CDRs having the amino acid sequence of SEQ ID NO: 25, the amino acid sequence of SEQ ID NO: 106 and the amino acid sequence of SEQ ID NO: 24, and
a light chain variable region including three CDRs having the amino acid sequence of SEQ ID NO: 16, the amino acid sequence of SEQ ID NO: 17 and the amino acid sequence of SEQ ID NO: 21.

57) A humanized monoclonal antibody or an antibody fragment thereof, having
a heavy chain variable region including three CDRs having the amino acid sequence of SEQ ID NO: 26, the amino acid sequence of SEQ ID NO: 27 and the amino acid sequence of SEQ ID NO: 28, and
a light chain variable region including three CDRs having the amino acid sequence of SEQ ID NO: 29, the amino acid sequence of SEQ ID NO: 30 and the amino acid sequence of SEQ ID NO: 31.

61) A humanized monoclonal antibody or an antibody fragment thereof, having
a heavy chain variable region including three CDRs having the amino acid sequence of SEQ ID NO: 32, the amino acid sequence of SEQ ID NO: 33 and the amino acid sequence of SEQ ID NO: 34, and
a light chain variable region including three CDRs having the amino acid sequence of SEQ ID NO: 35, the amino acid sequence of SEQ ID NO: 36 and the amino acid sequence of SEQ ID NO: 37.

65) A humanized monoclonal antibody or an antibody fragment thereof, having
a heavy chain variable region including three CDRs having the amino acid sequence of SEQ ID NO: 38, the amino acid sequence of SEQ ID NO: 39 and the amino acid sequence of SEQ ID NO: 40, and
a light chain variable region including three CDRs having the amino acid sequence of SEQ ID NO: 41, the amino acid sequence of SEQ ID NO: 42 and the amino acid sequence of SEQ ID NO: 43.

69) A humanized monoclonal antibody or an antibody fragment thereof, having
a heavy chain variable region including three CDRs having the amino acid sequence of SEQ ID NO: 44, the amino acid sequence of SEQ ID NO: 45 and the amino acid sequence of SEQ ID NO: 46, and
a light chain variable region including three CDRs having the amino acid sequence of SEQ ID NO: 47, the amino acid sequence of SEQ ID NO: 48 and the amino acid sequence of SEQ ID NO: 49.

73) A humanized monoclonal antibody or an antibody fragment thereof, having
a heavy chain variable region including three CDRs having the amino acid sequence of SEQ ID NO: 44, the amino acid sequence of SEQ ID NO: 45 and the amino acid sequence of SEQ ID NO: 50, and
a light chain variable region including three CDRs having the amino acid sequence of SEQ ID NO: 47, the amino acid sequence of SEQ ID NO: 48 and the amino acid sequence of SEQ ID NO: 49.

77) A humanized monoclonal antibody or an antibody fragment thereof, having
a heavy chain variable region including three CDRs having the amino acid sequence of SEQ ID NO: 44, the amino acid sequence of SEQ ID NO: 45 and the amino acid sequence of SEQ ID NO: 51, and
a light chain variable region including three CDRs having the amino acid sequence of SEQ ID NO: 47, the amino acid sequence of SEQ ID NO: 48 and the amino acid sequence of SEQ ID NO: 49.

81) A humanized monoclonal antibody or an antibody fragment thereof, having
a heavy chain variable region including three CDRs having the amino acid sequence of SEQ ID NO: 52, the amino acid sequence of SEQ ID NO: 45 and the amino acid sequence of SEQ ID NO: 53, and
a light chain variable region including three CDRs having the amino acid sequence of SEQ ID NO: 47, the amino acid sequence of SEQ ID NO: 48 and the amino acid sequence of SEQ ID NO: 49.

85) A humanized monoclonal antibody or an antibody fragment thereof, having
- a heavy chain variable region including three CDRs having the amino acid sequence of SEQ ID NO: 54, the amino acid sequence of SEQ ID NO: 55 and the amino acid sequence of SEQ ID NO: 56, and
- a light chain variable region including three CDRs having the amino acid sequence of SEQ ID NO: 57, the amino acid sequence of SEQ ID NO: 58 and the amino acid sequence of SEQ ID NO: 59.

(15) A humanized monoclonal antibody or an antibody fragment thereof, selected from the group of 1) A humanized monoclonal antibody or an antibody fragment thereof, having
- a heavy chain variable region having the amino acid sequence of SEQ ID NO: 60, and
- a light chain variable region having the amino acid sequence of SEQ ID NO: 61.

5) A humanized monoclonal antibody or an antibody fragment thereof, having
- a heavy chain variable region having the amino acid sequence of SEQ ID NO: 62, and
- a light chain variable region having the amino acid sequence of SEQ ID NO: 61.

9) A humanized monoclonal antibody or an antibody fragment thereof, having
- a heavy chain variable region having the amino acid sequence of SEQ ID NO: 63, and
- a light chain variable region having the amino acid sequence of SEQ ID NO: 61.

13) A humanized monoclonal antibody or an antibody fragment thereof, having
- a heavy chain variable region having the amino acid sequence of SEQ ID NO: 63, and
- a light chain variable region having the amino acid sequence of SEQ ID NO: 64.

17) A humanized monoclonal antibody or an antibody fragment thereof, having
- a heavy chain variable region having the amino acid sequence of SEQ ID NO: 65, and
- a light chain variable region having the amino acid sequence of SEQ ID NO: 61.

21) A humanized monoclonal antibody or an antibody fragment thereof, having
- a heavy chain variable region having the amino acid sequence of SEQ ID NO: 65, and
- a light chain variable region having the amino acid sequence of SEQ ID NO: 64.

25) A humanized monoclonal antibody or an antibody fragment thereof, having
- a heavy chain variable region having the amino acid sequence of SEQ ID NO: 66, and
- a light chain variable region having the amino acid sequence of SEQ ID NO: 61.

29) A humanized monoclonal antibody or an antibody fragment thereof, having
- a heavy chain variable region having the amino acid sequence of SEQ ID NO: 66, and
- a light chain variable region having the amino acid sequence of SEQ ID NO: 64.

33) A humanized monoclonal antibody or an antibody fragment thereof, having
- a heavy chain variable region having the amino acid sequence of SEQ ID NO: 62, and
- a light chain variable region having the amino acid sequence of SEQ ID NO: 67.

37) A humanized monoclonal antibody or an antibody fragment thereof, having
- a heavy chain variable region having the amino acid sequence of SEQ ID NO: 62, and
- a light chain variable region having the amino acid sequence of SEQ ID NO: 68.

41) A humanized monoclonal antibody or an antibody fragment thereof, having
- a heavy chain variable region having the amino acid sequence of SEQ ID NO: 62, and
- a light chain variable region having the amino acid sequence of SEQ ID NO: 69.

45) A humanized monoclonal antibody or an antibody fragment thereof, having
- a heavy chain variable region having the amino acid sequence of SEQ ID NO: 70, and
- a light chain variable region having the amino acid sequence of SEQ ID NO: 71.

49) A humanized monoclonal antibody or an antibody fragment thereof, having
- a heavy chain variable region having the amino acid sequence of SEQ ID NO: 72, and
- a light chain variable region having the amino acid sequence of SEQ ID NO: 71.

53) A humanized monoclonal antibody or an antibody fragment thereof, having
- a heavy chain variable region having the amino acid sequence of SEQ ID NO: 72, and
- a light chain variable region having the amino acid sequence of SEQ ID NO: 73.

57) A humanized monoclonal antibody or an antibody fragment thereof, having
- a heavy chain variable region having the amino acid sequence of SEQ ID NO: 74, and
- a light chain variable region having the amino acid sequence of SEQ ID NO: 71.

61) A humanized monoclonal antibody or an antibody fragment thereof, having
- a heavy chain variable region having the amino acid sequence of SEQ ID NO: 74, and
- a light chain variable region having the amino acid sequence of SEQ ID NO: 73.

65) A humanized monoclonal antibody or an antibody fragment thereof, having
- a heavy chain variable region having the amino acid sequence of SEQ ID NO: 75, and
- a light chain variable region having the amino acid sequence of SEQ ID NO: 71.

69) A humanized monoclonal antibody or an antibody fragment thereof, having
- a heavy chain variable region having the amino acid sequence of SEQ ID NO: 75, and
- a light chain variable region having the amino acid sequence of SEQ ID NO: 73.

73) A humanized monoclonal antibody or an antibody fragment thereof, having
- a heavy chain variable region having the amino acid sequence of SEQ ID NO: 70, and
- a light chain variable region having the amino acid sequence of SEQ ID NO: 76.

77) A humanized monoclonal antibody or an antibody fragment thereof, having
- a heavy chain variable region having the amino acid sequence of SEQ ID NO: 77, and a light chain variable region having the amino acid sequence of SEQ ID NO: 78.

81) A humanized monoclonal antibody or an antibody fragment thereof, having
a heavy chain variable region having the amino acid sequence of SEQ ID NO: 77, and
a light chain variable region having the amino acid sequence of SEQ ID NO: 79.

85) A humanized monoclonal antibody or an antibody fragment thereof, having
a heavy chain variable region having the amino acid sequence of SEQ ID NO: 77, and
a light chain variable region having the amino acid sequence of SEQ ID NO: 80.

89) A humanized monoclonal antibody or an antibody fragment thereof, having
a heavy chain variable region having the amino acid sequence of SEQ ID NO: 81, and
a light chain variable region having the amino acid sequence of SEQ ID NO: 79.

93) A humanized monoclonal antibody or an antibody fragment thereof, having
a heavy chain variable region having the amino acid sequence of SEQ ID NO: 81, and
a light chain variable region having the amino acid sequence of SEQ ID NO: 78.

97) A humanized monoclonal antibody or an antibody fragment thereof, having
a heavy chain variable region having the amino acid sequence of SEQ ID NO: 82, and
a light chain variable region having the amino acid sequence of SEQ ID NO: 83.

101) A humanized monoclonal antibody or an antibody fragment thereof, having
a heavy chain variable region having the amino acid sequence of SEQ ID NO: 82, and
a light chain variable region having the amino acid sequence of SEQ ID NO: 84.

105) A humanized monoclonal antibody or an antibody fragment thereof, having
a heavy chain variable region having the amino acid sequence of SEQ ID NO: 82, and
a light chain variable region having the amino acid sequence of SEQ ID NO: 85.

109) A humanized monoclonal antibody or an antibody fragment thereof, having
a heavy chain variable region having the amino acid sequence of SEQ ID NO: 86, and
a light chain variable region having the amino acid sequence of SEQ ID NO: 85.

113) A humanized monoclonal antibody or an antibody fragment thereof, having
a heavy chain variable region having the amino acid sequence of SEQ ID NO: 87, and
a light chain variable region having the amino acid sequence of SEQ ID NO: 88.

117) A humanized monoclonal antibody or an antibody fragment thereof, having
a heavy chain variable region having the amino acid sequence of SEQ ID NO: 87, and
a light chain variable region having the amino acid sequence of SEQ ID NO: 89.

121) A humanized monoclonal antibody or an antibody fragment thereof, having
a heavy chain variable region having the amino acid sequence of SEQ ID NO: 87, and
a light chain variable region having the amino acid sequence of SEQ ID NO: 90.

125) A humanized monoclonal antibody or an antibody fragment thereof, having
a heavy chain variable region having the amino acid sequence of SEQ ID NO: 91, and
a light chain variable region having the amino acid sequence of SEQ ID NO: 92.

129) A humanized monoclonal antibody or an antibody fragment thereof, having
a heavy chain variable region having the amino acid sequence of SEQ ID NO: 93, and
a light chain variable region having the amino acid sequence of SEQ ID NO: 92.

133) A humanized monoclonal antibody or an antibody fragment thereof, having
a heavy chain variable region having the amino acid sequence of SEQ ID NO: 91, and
a light chain variable region having the amino acid sequence of SEQ ID NO: 94.

137) A humanized monoclonal antibody or an antibody fragment thereof, having
a heavy chain variable region having the amino acid sequence of SEQ ID NO: 93, and
a light chain variable region having the amino acid sequence of SEQ ID NO: 94.

141) A humanized monoclonal antibody or an antibody fragment thereof, having
a heavy chain variable region having the amino acid sequence of SEQ ID NO: 95, and
a light chain variable region having the amino acid sequence of SEQ ID NO: 96.

145) A humanized monoclonal antibody or an antibody fragment thereof, having
a heavy chain variable region having the amino acid sequence of SEQ ID NO: 97, and
a light chain variable region having the amino acid sequence of SEQ ID NO: 96.

149) A humanized monoclonal antibody or an antibody fragment thereof, having
a heavy chain variable region having the amino acid sequence of SEQ ID NO: 98, and
a light chain variable region having the amino acid sequence of SEQ ID NO: 96.

153) A humanized monoclonal antibody or an antibody fragment thereof, having
a heavy chain variable region having the amino acid sequence of SEQ ID NO: 99, and
a light chain variable region having the amino acid sequence of SEQ ID NO: 96.

157) A humanized monoclonal antibody or an antibody fragment thereof, having
a heavy chain variable region having the amino acid sequence of SEQ ID NO: 100, and
a light chain variable region having the amino acid sequence of SEQ ID NO: 101.

161) A humanized monoclonal antibody or an antibody fragment thereof, having
a heavy chain variable region having the amino acid sequence of SEQ ID NO: 100, and
a light chain variable region having the amino acid sequence of SEQ ID NO: 102.

165) A humanized monoclonal antibody or an antibody fragment thereof, having
a heavy chain variable region having the amino acid sequence of SEQ ID NO: 100, and a light chain variable region having the amino acid sequence of SEQ ID NO: 103.
169) A humanized monoclonal antibody or an antibody fragment thereof, having
  a heavy chain variable region having the amino acid sequence of SEQ ID NO: 100, and
  a light chain variable region having the amino acid sequence of SEQ ID NO: 104.
173) A humanized monoclonal antibody or an antibody fragment thereof, having
  a heavy chain variable region having the amino acid sequence of SEQ ID NO: 100, and
  a light chain variable region having the amino acid sequence of SEQ ID NO: 105.
(16) A humanized monoclonal antibody or an antibody fragment thereof,
selected from the group of
1) A humanized monoclonal antibody or an antibody fragment thereof, having
  a heavy chain variable region having the amino acid sequence of SEQ ID NO: 60, and
  a light chain variable region having the amino acid sequence of SEQ ID NO: 64.
2) A humanized monoclonal antibody or an antibody fragment thereof, having
  a heavy chain variable region having the amino acid sequence of SEQ ID NO: 60, and
  a light chain variable region having the amino acid sequence of SEQ ID NO: 67.
3) A humanized monoclonal antibody or an antibody fragment thereof, having
  a heavy chain variable region having the amino acid sequence of SEQ ID NO: 60, and
  a light chain variable region having the amino acid sequence of SEQ ID NO: 68.
4) A humanized monoclonal antibody or an antibody fragment thereof, having
  a heavy chain variable region having the amino acid sequence of SEQ ID NO: 60, and
  a light chain variable region having the amino acid sequence of SEQ ID NO: 69.
5) A humanized monoclonal antibody or an antibody fragment thereof, having
  a heavy chain variable region having the amino acid sequence of SEQ ID NO: 62, and
  a light chain variable region having the amino acid sequence of SEQ ID NO: 64.
6) A humanized monoclonal antibody or an antibody fragment thereof, having
  a heavy chain variable region having the amino acid sequence of SEQ ID NO: 63, and
  a light chain variable region having the amino acid sequence of SEQ ID NO: 67.
7) A humanized monoclonal antibody or an antibody fragment thereof, having
  a heavy chain variable region having the amino acid sequence of SEQ ID NO: 63, and
  a light chain variable region having the amino acid sequence of SEQ ID NO: 68.
8) A humanized monoclonal antibody or an antibody fragment thereof, having
  a heavy chain variable region having the amino acid sequence of SEQ ID NO: 63, and
  a light chain variable region having the amino acid sequence of SEQ ID NO: 69.
9) A humanized monoclonal antibody or an antibody fragment thereof, having
  a heavy chain variable region having the amino acid sequence of SEQ ID NO: 65, and
  a light chain variable region having the amino acid sequence of SEQ ID NO: 67.
10) A humanized monoclonal antibody or an antibody fragment thereof, having
  a heavy chain variable region having the amino acid sequence of SEQ ID NO: 65, and
  a light chain variable region having the amino acid sequence of SEQ ID NO: 68.
11) A humanized monoclonal antibody or an antibody fragment thereof, having
  a heavy chain variable region having the amino acid sequence of SEQ ID NO: 65, and
  a light chain variable region having the amino acid sequence of SEQ ID NO: 69.
12) A humanized monoclonal antibody or an antibody fragment thereof, having
  a heavy chain variable region having the amino acid sequence of SEQ ID NO: 66, and
  a light chain variable region having the amino acid sequence of SEQ ID NO: 67.
13) A humanized monoclonal antibody or an antibody fragment thereof, having
  a heavy chain variable region having the amino acid sequence of SEQ ID NO: 66, and
  a light chain variable region having the amino acid sequence of SEQ ID NO: 68.
14) A humanized monoclonal antibody or an antibody fragment thereof, having
  a heavy chain variable region having the amino acid sequence of SEQ ID NO: 66, and
  a light chain variable region having the amino acid sequence of SEQ ID NO: 69.
15) A humanized monoclonal antibody or an antibody fragment thereof, having
  a heavy chain variable region having the amino acid sequence of SEQ ID NO: 70, and
  a light chain variable region having the amino acid sequence of SEQ ID NO: 73.
16) A humanized monoclonal antibody or an antibody fragment thereof, having
  a heavy chain variable region having the amino acid sequence of SEQ ID NO: 70, and
  a light chain variable region having the amino acid sequence of SEQ ID NO: 78.
17) A humanized monoclonal antibody or an antibody fragment thereof, having
  a heavy chain variable region having the amino acid sequence of SEQ ID NO: 70, and
  a light chain variable region having the amino acid sequence of SEQ ID NO: 79.
18) A humanized monoclonal antibody or an antibody fragment thereof, having
  a heavy chain variable region having the amino acid sequence of SEQ ID NO: 70, and
  a light chain variable region having the amino acid sequence of SEQ ID NO: 80.
19) A humanized monoclonal antibody or an antibody fragment thereof, having
  a heavy chain variable region having the amino acid sequence of SEQ ID NO: 72, and
  a light chain variable region having the amino acid sequence of SEQ ID NO: 76.
20) A humanized monoclonal antibody or an antibody fragment thereof, having a heavy chain variable region having the amino acid sequence of SEQ ID NO: 72, and
a light chain variable region having the amino acid sequence of SEQ ID NO: 78.
21) A humanized monoclonal antibody or an antibody fragment thereof, having
a heavy chain variable region having the amino acid sequence of SEQ ID NO: 72, and
a light chain variable region having the amino acid sequence of SEQ ID NO: 79.
22) A humanized monoclonal antibody or an antibody fragment thereof, having
a heavy chain variable region having the amino acid sequence of SEQ ID NO: 72, and
a light chain variable region having the amino acid sequence of SEQ ID NO: 80.
23) A humanized monoclonal antibody or an antibody fragment thereof, having
a heavy chain variable region having the amino acid sequence of SEQ ID NO: 74, and
a light chain variable region having the amino acid sequence of SEQ ID NO: 76.
24) A humanized monoclonal antibody or an antibody fragment thereof, having
a heavy chain variable region having the amino acid sequence of SEQ ID NO: 74, and
a light chain variable region having the amino acid sequence of SEQ ID NO: 78.
25) A humanized monoclonal antibody or an antibody fragment thereof, having
a heavy chain variable region having the amino acid sequence of SEQ ID NO: 74, and
a light chain variable region having the amino acid sequence of SEQ ID NO: 79.
26) A humanized monoclonal antibody or an antibody fragment thereof, having
a heavy chain variable region having the amino acid sequence of SEQ ID NO: 74, and
a light chain variable region having the amino acid sequence of SEQ ID NO: 80.
27) A humanized monoclonal antibody or an antibody fragment thereof, having
a heavy chain variable region having the amino acid sequence of SEQ ID NO: 75, and
a light chain variable region having the amino acid sequence of SEQ ID NO: 76.
28) A humanized monoclonal antibody or an antibody fragment thereof, having
a heavy chain variable region having the amino acid sequence of SEQ ID NO: 75, and
a light chain variable region having the amino acid sequence of SEQ ID NO: 78.
29) A humanized monoclonal antibody or an antibody fragment thereof, having
a heavy chain variable region having the amino acid sequence of SEQ ID NO: 75, and
a light chain variable region having the amino acid sequence of SEQ ID NO: 79.
30) A humanized monoclonal antibody or an antibody fragment thereof, having
a heavy chain variable region having the amino acid sequence of SEQ ID NO: 75, and
a light chain variable region having the amino acid sequence of SEQ ID NO: 80.
31) A humanized monoclonal antibody or an antibody fragment thereof, having
a heavy chain variable region having the amino acid sequence of SEQ ID NO: 77, and
a light chain variable region having the amino acid sequence of SEQ ID NO: 71.
32) A humanized monoclonal antibody or an antibody fragment thereof, having
a heavy chain variable region having the amino acid sequence of SEQ ID NO: 77, and
a light chain variable region having the amino acid sequence of SEQ ID NO: 73.
33) A humanized monoclonal antibody or an antibody fragment thereof, having
a heavy chain variable region having the amino acid sequence of SEQ ID NO: 77, and
a light chain variable region having the amino acid sequence of SEQ ID NO: 76.
34) A humanized monoclonal antibody or an antibody fragment thereof, having
a heavy chain variable region having the amino acid sequence of SEQ ID NO: 81, and
a light chain variable region having the amino acid sequence of SEQ ID NO: 71.
35) A humanized monoclonal antibody or an antibody fragment thereof, having
a heavy chain variable region having the amino acid sequence of SEQ ID NO: 81, and
a light chain variable region having the amino acid sequence of SEQ ID NO: 73.
36) A humanized monoclonal antibody or an antibody fragment thereof, having
a heavy chain variable region having the amino acid sequence of SEQ ID NO: 81, and
a light chain variable region having the amino acid sequence of SEQ ID NO: 76.
37) A humanized monoclonal antibody or an antibody fragment thereof, having
a heavy chain variable region having the amino acid sequence of SEQ ID NO: 81, and
a light chain variable region having the amino acid sequence of SEQ ID NO: 80.
38) A humanized monoclonal antibody or an antibody fragment thereof, having
a heavy chain variable region having the amino acid sequence of SEQ ID NO: 86, and
a light chain variable region having the amino acid sequence of SEQ ID NO: 83.
39) A humanized monoclonal antibody or an antibody fragment thereof, having
a heavy chain variable region having the amino acid sequence of SEQ ID NO: 86, and
a light chain variable region having the amino acid sequence of SEQ ID NO: 84.
(17) The pharmaceutical composition for treating or preventing a disease related to vascular endothelial lipase, comprising the humanized monoclonal antibody or the antibody fragment thereof of any one of (1) to (16).
(18) The pharmaceutical composition of (17), wherein the disease related to vascular endothelial lipase is dyslipidemia.
(19) The humanized monoclonal antibody or the antibody fragment thereof of any one of (1) to (16) for the treatment or prevention of a disease related to vascular endothelial lipase.
(20) The humanized monoclonal antibody or the antibody fragment thereof of (19), wherein the disease related to vascular endothelial lipase is dyslipidemia.
(21) A method for the treatment or prevention of a disease related to vascular endothelial lipase characterized by administering to a humanized monoclonal antibody or the antibody fragment thereof of any one of (1) to (16).
(21) The method of (21), wherein the disease related to vascular endothelial lipase is dyslipidemia.

Effect of the Invention

As a humanized monoclonal antibody of the present invention has the activity for selectively inhibiting enzymatic activity of EL, pharmaceutical compositions containing the humanized monoclonal antibody of the present invention is very useful as a drug, especially a drug for prevention and/or treatment of dyslipidemia, hyperlipidemia, arteriosclerosis, atherosclerosis, hypercholesterolemia, hypertriglyceridemia, diabetes, obesity and/or syndrome X.

BRIEF EXPLANATION OF DRAWINGS

FIG. 3A to 3L show measurement results of binding activity of 55A1, 7D4, 14A1, 2D5, 53A11, 13B3, 23H8, 16B3, 16E7, 14E1, 19E7 and 16F6 antibodies against cynomolgus EL, baboon EL, rabbit EL, mouse EL and human (1-157) mouse chimera EL, human (1-305) mouse chimera EL, human (202-500) mouse chimera EL or human (187-500) mouse chimera EL.

FIG. 4A to 4L (SEQ ID NOS: 107-130) show the amino acid sequences of the variable regions of 55A1, 7D4, 14A1, 2D5, 53A11, 13B3, 23H8, 16B3, 16E7, 14E1, 19E7 and 16F6 antibodies.

FIG. 5A to 5D show alignments of the amino acid sequences of heavy chain variable region or light chain variable region of 55A1, 7D4, 14A1 and 2D5 antibodies (SEQ ID NOS: 107, 109, 111, 113, 108, 110, 112 and 114, respectively), or 53A11, 13B3 and 23H8 antibodies (SEQ ID NOS: 115, 117, 119, 116, 118 and 120, respectively).

FIG. 6A to 6D show alignments of the amino acid sequences of heavy chain variable region or light chain variable region of 16B3 and 16E7 antibodies (SEQ ID NOS: 121, 123, 122 and 124, respectively), or 14E1 and (19E7) antibodies (SEQ ID NOS: 125, 127, 126 and 128, respectively)

FIG. 7A to 7L show binding activity of 55A1, 7D4, 14A1, 2D5, 53A11, 13B3, 23118, 16B3, 16E7, 14E1, 19E7 or 16F6 antibody against baboon EL that was introduced mutation.

FIG. 8A to 8D show alignments of the amino acid sequences of heavy chain variable region or light chain variable region of h16B3-S1 to S8 antibodies (heavy chain is SEQ ID NOS: 60, 62, 63, 63, 65, 65, 66, and 66, respectively; light chain is SEQ ID NOS: 61, 61, 61, 64, 61, 64, 61 and 64, respectively) or h16B3-F1 to F3 antibodies (each heavy chain is SEQ ID NO: 62, light chain is SEQ ID NOS: 67, 68 and 69, respectively)

FIG. 9A to 9D show alignments of the amino acid sequences of heavy chain variable region or light chain variable region of h55A1-S1 to S7 antibodies (heavy chain is SEQ ID NOS: 70, 72, 72, 74, 74, 75, and 75, respectively; light chain is SEQ ID NOS: 71, 71, 73, 71, 73, 71 and 73, respectively) or h55A1-F1 to F6 antibodies (heavy chain is SEQ ID NOS: 70, 77, 77, 77, 81 and 81, respectively; light chain is SEQ ID NOS: 76, 78, 79, 80, 79 and 78, respectively).

FIGS. 10A and 10B show alignments of the amino acid sequences of heavy chain variable region or light chain variable region of h53A11-S1 to S4 antibodies (heavy chain is SEQ ID NOS: 82, 82, 82 and 86, respectively; light chain is SEQ ID NOS: 83, 84, 85 and 85).

FIGS. 11A and 11B show alignments of the amino acid sequences of heavy chain variable region or light chain variable region of h23H8-S1 to S3 antibodies (each heavy chain is SEQ ID NO: 87; light chain is SEQ ID NOS: 88, 89 and 90, respectively).

FIGS. 12A and 12B show alignments of the amino acid sequences of heavy chain variable region or light chain variable region of h13B3-S1 to S4 antibodies (heavy chain is SEQ ID NOS: 91, 93, 91 and 93; light chain is SEQ ID NOS: 92, 92, 94 and 94, respectively).

FIGS. 13A and 13B show alignments of the amino acid sequences of heavy chain variable region or light chain variable region of h12B10-S1 to S4 antibodies (heavy chain is SEQ ID NOS: 95, 97, 98 and 99, respectively; each light chain is SEQ ID NO: 96).

FIGS. 14A and 14B show alignments of the amino acid sequences of heavy chain variable region or light chain variable region of h16F6-S1 to S5 antibodies (each heavy chain is SEQ ID NO: 100; light chain is SEQ ID NOS: 101, 102, 103, 104 and 105).

FIG. 15A to 15K show the amino acid sequences of the variable regions of h16B3-S1 to S8, F1 to F3 antibody (SEQ ID NOS: 60, 61, 62, 61, 63, 61, 63, 64, 65, 61, 65, 64, 66, 61, 66, 64, 62, 67, 62, 68, 62 and 69, respectively).

FIG. 16A to 16M show the amino acid sequences of the variable regions of h55A1-S1 to S7, F1 to F6 antibody (SEQ ID NOS: 70, 71, 72, 71, 72, 73, 74, 71, 74, 73, 75, 71, 75, 73, 70, 76, 77, 78, 77, 79, 77, 80, 81, 79, 81 and 78, respectively).

FIG. 17A to 17D show the amino acid sequences of the variable regions of h53A11-S1 to S4 antibody (SEQ ID NOS: 82, 83, 82, 84, 82, 85, 86 and 85, respectively).

FIG. 18A to 18C show the amino acid sequences of the variable regions of h23H8-S1 to S3 antibody (SEQ ID NOS: 87, 88, 87, 89, 87 and 90, respectively).

FIG. 19A to 19D show the amino acid sequences of the variable regions of h13B3-S1 to S4 antibody (SEQ ID NOS: 91, 92, 93, 92, 91, 94, 93 and 94, respectively).

FIG. 20A to 20D show the amino acid sequences of the variable regions of h12B10-S1 to S4 antibody (SEQ ID NOS: 95, 96, 97, 96, 98, 96, 99 and 96, respectively).

FIG. 21A to 21E show the amino acid sequences of the variable regions of h16F6-S1 to S5 antibody (SEQ ID NOS: 100, 101, 100, 102, 100, 103, 100, 104, 100 and 105, respectively).

MODE FOR CARRYING OUT THE INVENTION

Figure 1A:
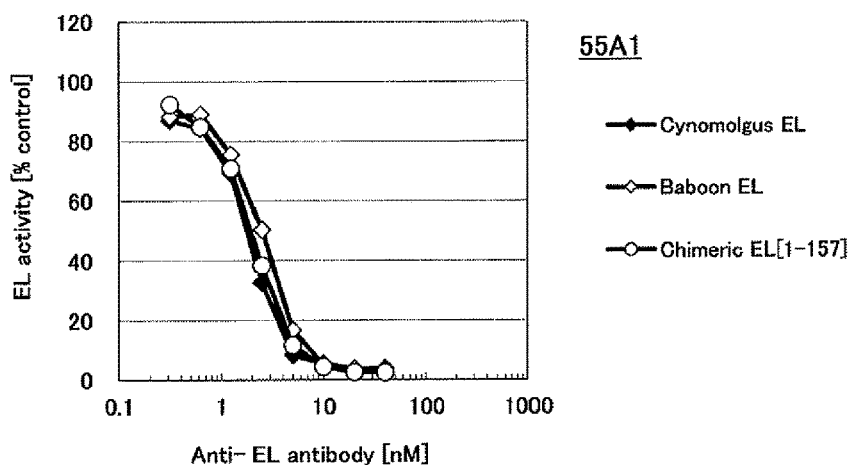
FIG. 1A to 1K show measurement results of inhibition of enzymatic activity of 55A1, 7D4, 14A1, 2D5, 53A11, 13B3, 23H8, 16B3, 16E7, 14E1 and 19E7 antibodies antibody against cynomolgus EL, baboon EL, human (1-157) mouse chimera EL or human (1-305) mouse chimera EL.

The present invention provides a humanized monoclonal antibody characterized by selectively inhibiting the enzymatic activity of vascular endothelial lipase. As the monoclonal antibody of the present invention has the activity for selectively inhibiting enzymatic activity of vascular endothelial lipase, it is very useful as a drug for prevention or treatment of arteriosclerosis or metabolic syndrome.

It is important to use peptide having consecutive amino acid residues containing the amino acid sequence at positions of 1 to 157 or 202 to 305 region in the amino acid sequence of SEQ ID NO: 1 as antigen to produce a monoclonal antibody of the present invention. The length is not particularly limited, but six or more residues which have immunogenicity are desired. We can use naturally or artificially highly expressed cell lines, these membrane fractions, these purified products, fusion proteins with other proteins or peptides (for examples, tag proteins such as FLAG-tag, HIS-tag, GST-tag or C2tag etc. or fluorescent proteins such as GFP or EGFP etc.), or chemically synthesized peptides as specific examples of these antibodies. In addition, preparation methods of these immunogens are known to those skilled in the art.

The monoclonal antibody of the present invention may be prepared by an known commonly used production method. Concretely, a mammal, preferably, mouse, rat, hamster, guinea pig, rabbit, cat, dog, pig, goat, sheep, donkey, horse or bovine, more preferably mouse, rat, hamster, guinea pig or rabbit is immunized with an immunogen of the present invention, together with Freund's adjuvant as necessary, by one or several times of subcutaneous, intramuscular, intravenous, intrafootpad or intraperitoneal injection. Usually, immunization is conducted once to four times every about 1 to 21 days after primary immunization, and antibody producing cells may be acquired from the immunized mammal after about 1 to 10 days from the final immunization. The number of times and time interval of immunization may be appropriately changed depending on the property of the immunogen being used.

Hybridoma that secrets monoclonal antibody may be prepared according to the Kohler and Milstein's method (Nature, 1975, vol. 256, p. 495-497) and a corresponding method. That is, hybridoma may be prepared by cell fusion between an antibody producing cell contained in spleen, lymph node, bone marrow, tonsil or the like, preferably in spleen acquired from a mammal immunized as described above, and a myeloma cell lacking autoantibody producing ability derived, preferably from a mammal such as mouse, rat, guinea pig, hamster, rabbit or human, more preferably from mouse, rat or human.

As a myeloma cell used in cell fusion, generally, cell lines obtained from mouse, for example, P3-U1, NS-1, SP-2, 653, X63, AP-1 and the like may be used.

Hybridoma that produces monoclonal antibody is screened by culturing a hybridoma, for example, in a microtiter plate, measuring reactivity to an immunogen used in mouse immunization as described above in culture supernatant in the well where proliferation is observed, by a measuring method such as RIA, ELISA or FACS and selecting a clone that produces a monoclonal antibody exhibiting specific affinity with the immunogen or hapten. When measuring the said reactivity, an immunogen is usually solid-phased, and an antibody in culture supernatant that binds to the solid-phased immunogen is detected by an anti-mouse secondary antibody labeled with a radioactive substance, a fluorescent substance or an enzyme. Further in the case of using the cells expressing the immunogen, we add the hybridoma culture supernatant to the cells, then after reacting with secondary antibodies labeled with a fluorescent, we can detect a monoclonal antibody of the present invention that binds to the immunogen on the cell membrane by measuring fluorescence intensity of the cells with fluorescence detection apparatus such as flow cytometry or the like.

Production of monoclonal antibody from selected hybridoma may be achieved by culturing hybridoma in vitro or in ascites of mouse, rat, guinea pig, hamster or rabbit, preferably of mouse or rat, or more preferably of mouse, followed by isolation from the obtained culture supernatant or ascites of mammal. In the case of in vitro culture, the hybridoma may be cultured in a known nutrient medium or in any nutrient cultures derived and prepared from a known base medium used for proliferating, maintaining and storing hybridoma and for producing monoclonal antibody in culture supernatant, depending on various conditions such as property of cultured cell species, object of the test research and culturing method.

As a base medium, for example, low-calcium media such as Ham'F12 medium, MCDB153 medium or low-calcium MEM culture, and high-calcium media such as MCDB104 medium, MEM medium, D-MEM medium, RPMI1640 medium, AF104 medium, or RD medium can be recited, and such a base medium may contain, for example, serum, hormone, cytokine and/or various inorganic or organic substances depending on the object.

Isolation and purification of monoclonal antibody may be achieved by subjecting the culture supernatant or ascites as described above to saturated ammonium sulfate, ion exchange chromatography (e.g., DEAE or DE52), affinity column chromatography such as anti-immunoglobulin column or protein A column or the like.

As a monoclonal antibody of the present invention, a recombinant antibody that is produced using gene recombination technique in such a manner that an antibody gene is cloned from antibody producing cell, for example, hybridoma, and incorporated into an appropriate vector, and the vector is introduced into a host may be used (for example, Carl et al., THERAPEUTIC MONOCLONAL ANTIBODIES, published in 1990).

Concretely, from a hybridoma that produces an objective antibody, or from an immune cell that produces an antibody, for example, from a cell obtained by immortalizing sensitized lymphocyte or the like by cancer gene or the like, mRNA encoding a variable region (V region) of antibody is isolated. In isolation of mRNA, whole RNA is prepared by a known method, for example, by guanidine ultracentrifugation (Chirgwin, J. M. et al., Biochemistry (1979) 18, 5294-5299) or the like, and mRNA is prepared by using mRNA Purification Kit (available from Pharmacia) or the like.

From the obtained mRNA, cDNA of antibody V region is synthesized using a reverse transcriptase. Synthesis of cDNA may be conducted using AMV Reverse Transcriptase First-strand cDNA Synthesis Kit or the like. Further, for synthesis and amplification of cDNA, 5'-Ampli FINDER RACEKit (available from Clonetech) and 5'-RACE method using PCR (Frohman, M. A. et al, Proc. Natl. Acad. Sci. USA 1988, vol. 85, p. 8998) may be used. An objective DNA fragment is purified from the obtained PCR product, and connected with vector DNA. A recombinant vector is thus created and introduced into *E. coli* or the like, and a colony is selected and a desired recombinant vector is prepared. DNA base sequence of objective DNA is verified by a known method, for example, by deoxy method.

If DNA encoding V region of objective antibody is obtained, the DNA is connected with DNA encoding a desired antibody constant region (C region), and incorporated into an expression vector. Alternatively, DNA encoding V region of antibody may be incorporated into an expression vector containing DNA of antibody C region. For production of antibody used in the present invention, antibody gene is incorporated into an expression vector in such a manner that it is expressed under control of an expression control region, for example, enhancer/promoter. Next, a host cell can be transformed with this expression vector to cause expression of antibody.

For expression of antibody gene, heavy chain (H chain) or light chain (L chain) of antibody may be separately incorporated into expression vectors, or a host may be co-transformed with these expression vectors, or DNA encoding H chain and L chain may be incorporated into a single expression vector to transform a host with the resultant expression vector (see WO94/11523).

Preparation method of a monoclonal antibody of the present invention other than the above can be also used so called phage display technology. Concretely, for example antibody gene library prepared as a material human or animal (for example, rabbit, mouse, rat, hamster or the like) B lymphosate by known method or completely synthesized antibody gene library prepared from selected and modified human or animal germ line sequence is presented to the cell surface, on the ribosome or the like of bacteriophage, *Escherichia coli*, yeast, animal cells or the like. In this case, the forms of the antibody to be presented on the cell surface are listed IgG molecules, IgM molecules, Fab fragments, single chain Fv (scFv) fragments, etc.

We can obtain antibody genes by rearranging thus obtained monoclonal antibody fragment to the corresponding region of the IgG antibody gene by a known method. And we incorporate thus genes obtained in this manner into a suitable vector, introduce the vector into the host, we can prepare the antibody with recombinant DNA techniques (for examples, see Carl ad THERAPEUTIC MONOCLONAL ANTIBODIES, 1990 issue).

The monoclonal antibody of the present invention is characterized in being selective for the inhibition of the enzymatic activity of vascular endothelial lipase. Below, we show an example of a procedure for measuring ability of inhibiting the enzymatic activity of EL.

The DNA encoding EL is cloned into pcDNA3.1 expression vector (Invitrogen). The expression vector is transfected into HEK293F cells and culture at 37° C., 8% CO2 for 2 days. The cell cultures are centrifuged, the cells are collected, and the cells are suspended with PBS containing 20 U/mL of Heparin. The cell suspension is incubated at 37° C. for 45 min. The supernatant obtained by removing cells with centrifugation is used as human EL enzyme solution to measure inhibitory activity.

After adding a monoclonal antibody to the solution containing 20 mM Tris-HCl Buffer (pH 7.5), 0.5% bovine serum albumin, 4 mM $CaCl_2$), 150 mM NaCl and 2 mg/mL human HDL (Athens Research & Techonology), EL enzyme solution is added. After reaction at 37° C. for 2 hr, free fatty acid (NEFA) made from HDL by EL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of the antibody. The concentration where 50% of the antibody is inhibited can be calculated from the inhibition curve.

Effective concentration (IC50) of antibody which shows 50% inhibition of EL enzyme activity is often used as an indicator of EL inhibitory activity.

In the present invention, a monoclonal antibody or an antibody fragment thereof inhibiting the enzymatic activity of vascular endothelial lipase with an IC50 of 10 nM or less means a monoclonal antibody or a fragment thereof showing IC50 of 10 nM or less. Any species EL may be used for the measurement if the EL is derived from a mammal. If a monoclonal antibody or an antibody fragment thereof inhibits the enzymatic activity of EL of any kind of mammal species with an IC50 of 10 nM or less, the monoclonal antibody or an antibody fragment thereof is a monoclonal antibody or an antibody fragment thereof showing IC50 of 10 nM or less.

And the monoclonal antibody of the present invention is characterized in being selective for the inhibition of the enzymatic activity of EL. Below, we show an example of a confirmation procedure for measuring ability of selectively inhibiting the enzymatic activity of EL, in other words, not inhibiting the enzymatic activity of LPL or HL.

The DNA encoding HL is cloned into pcDNA3.1 expression vector (Invitrogen). The expression vector is transfected into HEK293F cells and culture at 37° C. 8% CO2 for 2 days. The cell cultures are centrifuged, the cells are collected, and the cells are suspended with PBS containing 20 U/mL of Heparin. The cell suspension is incubated at 37° C. for 45 min. The supernatant obtained by removing cells with centrifugation is used as human HL enzyme solution. LPL enzyme solution is prepared by using the same procedures. After adding a monoclonal antibody to the solution containing 20 mM Tris-HCl Buffer (pH 7.5), 0.5% bovine serum albumin, 4 mM CaCl2, 150 mM NaCl and 0.5 mg/mL human VLDL (INTRACEL), HL or LPL enzyme solution is added. After reaction at 37° C. for 2 hr, free fatty acid (NEFA) made from VLDL by HL or LPL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of antibody.

Being selective for the inhibition of the enzymatic activity of EL means inhibiting not more than 3% LPL or HL enzymatic activities, when the monoclonal antibody are added at a concentration equal to IC50 against EL. An epitope region of a monoclonal antibody of the present invention is preferably the region of EL that has not homology with LPL or HL because a monoclonal antibody of the present invention is characterized by not inhibiting enzyme activity of LPL and HL, and is characterized in being selective for the inhibition of enzyme activity of EL.

The humanized monoclonal antibody of the present invention is a humanized version of monoclonal antibody having above described feature. A humanized monoclonal antibody is obtained by transplanting a complementarity determining region (CDR) of antibody of a mammal other than human, for example, of a mouse, into CDR of human antibody. Therefore, framework region derives from human antibody. Suitable framework can be selected according to documents of Kabat E. A. et al. FR can be selected in such a manner that CDR can form appropriate antigen-binding site. If necessary, amino acid of FR of variable region may be substituted in such a manner that CDR of reconstructed humanized antibody can form appropriate antigen-binding site (Sato, K. et al., Cancer Res. 1993, vol. 53. p 851). The proportion of substituted amino acids of the FR is 0 to 15% of all FR region, preferably 0 to 5% of all FR region.

General production method for humanized monoclonal antibody is also known (for example, WO95/14041 and WO96/02576 etc.). Concretely, DNA sequence, encoding variable region designed to connect CDR of mouse antibody with FR of human antibody, is synthesized by PCR method from several oligonucleotides prepared to have overlapping parts in their terminals (refer to WO98/13388). Obtained DNA is connected to DNA encoding constant region of human antibody and the resultant DNA is incorporated into expression vector. Alternatively, DNA encoding variable region of antibody may be incorporated into expression vector comprising DNA encoding constant region of antibody. To prepare for antibody of the present invention, antibody gene may be incorporated into an expression vector to express under control of an expression control region, for example enhancer/promoter. Further, the host cells are transformed with this expression vector and could thus produce antibody. As host cell, vertebrate cell such as COS cells or CHO cells, procaryotic cell or yeast can be recited.

For expression of antibody gene, genes of heavy chain (H chain) and light chain chain) of antibody may be separately incorporated into expression vectors, and a host may be transformed simultaneously with these expression vectors, or DNA encoding H chain and L chain may be incorporated into a single expression vector to transform a host with the resultant expression vector (see WO94/11523).

Desirable transformants, obtained by methods previously described, can be cultured by the methods known for the skilled person. By this culture, humanized monoclonal antibody against PcrV is produced in the transformants or outside the cells. Medium for the culture can be selected from conventional mediums appropriately depending on the host cell. In the case of above described COS cells, medium such as RPMI-1640, Dulbecco's Modified Eagle Minimum Essential Medium (DMEM), are available and if necessary, the serum ingredients likewise Fetal Bovine Serum (FBS) can be added. The temperature for cultivating the transformants is not restricted, as far as not lowering the ability for producing protein in the cell seriously. Preferably temperatures of 32 to 42° C. are recited. Most preferably, temperature of 37° C. is recited. As necessary, cultivating can be performed in the atmosphere containing carbon dioxide of 1 to 10% (v/v).

Fractions containing humanized antibody against PcrV of the present invention, produced in the transformants or outside cells by the methods previously described, can be refined by the heretofore known separation methods. These methods are based on physical property or chemical property of the target protein. Concretely, for example, treatment with protein precipitant, chromatography such as ultrafiltration chromatography, size separation chromatography, adsorption filtration chromatography, ion exchange chromatography, affinity chromatography, or high performance liquid chromatography, dialysis, and combination thereof are available.

According to methods previously described, desirable humanized monoclonal antibody against EL can be produced easily in good yield and good purity. The amino acid sequences of the variable regions of the optimized antibodies are shown as FIG. 15 to 21. These antibodies were constructed by grafting amino acid of whole CDR sequences and partial FR sequences, which are determined for humanization of mouse monoclonal antibody (16B3, 55A1, 53A11, 23118, 13B3, 12B10 or 16F6), into human antibody.

Compared to mouse antibody (16B3, 55A1, 53A11, 23H8, 13B3, 12B10 or 16F6) produced by hybridoma cells, these humanized antibodies had equivalent the enzymatic inhibitory activity of EL. Though humanization of antibody with maintaining activity of the original antibody is usually difficult, the inventors of the present invention were successful to obtain humanized antibody having equivalent activity of the original mouse antibody. Humanized antibody is useful for the purpose for treatment because of its lower antigenicity in human body.

As a constant region the humanized antibody of the present invention, human antibody constant region is available. As a preferred human antibody constant region, Cγ can be recited for heavy chain, and for example, Cγ1, Cγ2, Cγ3 and Cγ4 may be used and Cκ or Cλ can be recited for light chain. Further, human antibody C region may be modified to improve its stability of antibody or its productivity. In humanization, available human antibody may be any isotype such as IgG, IgM, IgA, IgE and IgD. In the present invention, IgG is preferable and IgG1 or IgG4 are more preferable.

Humanized monoclonal antibody of the present invention may be conjugated antibody, which is made by conjugating with some molecule such as polyethylene glycol (PEG), radioactive substance, or toxin. These conjugated monoclonal antibodies are obtained by modifying the antibody chemically. Methods for modifying antibody have established in this technical field. Humanized monoclonal antibody of the present invention embraces these conjugated monoclonal antibodies.

Humanized monoclonal antibody of the present invention may be fused with other proteins at its N terminal site or C terminal site (Clinical Cancer Research, 2004, 10, 1274-1281. The skilled person can select proteins for fusion appropriately.

In the present invention, "a monoclonal antibody fragment" means a part of the above-mentioned monoclonal antibody of the present invention and has the specific binding ability to vascular endothelial lipase as with the monoclonal antibody, or means a fragment that has the specific binding ability to vascular endothelial lipase as with the monoclonal antibody and has the effect of the inhibiting enzymatic activity of vascular endothelial lipase as with the monoclonal antibody.

Concretely, fragments that have specific associativity against EL are listed Fab, $F(ab')_2$, Fab', single chain antibody (scFv), disulfide stabilized antibody (dsFv), dimerized V region fragment (Diabody), peptide containing CDR, etc. (Expert opinion on therapeutic patents, vol. 6, No. 5, p. 441-456, 1996).

Fab is an antibody fragment having a molecular weight of about 50,000 with antigen binding activity, made up of about a half of N-terminal side of H chain and whole L chain, obtained by degrading with an enzyme papain a peptide part above two disulfide bonds (S—S bond) cross-linking two H chains in hinge region of IgG. Fab used in the present invention may be obtained by treating the monoclonal antibody of the present invention with papain. Alternatively, Fab may be produced by inserting DNA encoding Fab of monoclonal antibody of the present invention into an expression vector for cell and by introducing the vector into a cell to cause expression.

$F(ab')_2$ is an antibody fragment having a molecular weight of about 100,000 with antigen binding activity, formed by binding two Fab' regions in a hinge part. These Fab' regions are obtained by pepsin degradation below two S—S bonds of hinge region of IgG. The $F(ab')_2$ used in the present invention may be obtained by treating the monoclonal antibody of the present invention with pepsin. Alternatively, $F(ab')_2$ may be produced by inserting DNA encoding $F(ab')_2$ of the monoclonal antibody into an expression vector for cell and by introducing the vector into E. coli, yeast or animal cell to cause expression.

Fab' is an antibody fragment having a molecular weight of about 50,000 with antigen binding activity, obtained by cutting S—S bond between hinges of the aforementioned $F(ab')_2$. Fab' used in the present invention may be obtained by treating $F(ab')_2$ of monoclonal antibody of the present invention with a reducing agent, dithiothreitol. Alternatively, Fab' may be produced by inserting DNA encoding Fab' of the monoclonal antibody into an expression vector for cell and by introducing the vector into *E. coli*, yeast or animal cell to cause expression.

scFv is VH-P-VL or VL-P-VH peptide in which one VH chain and one VL chain are connected using an appropriate peptide linker (hereinafter, denoted by P), and is an antibody fragment having antigen activity. VH and VL contained in scFv used in the present invention may be derived from the monoclonal antibody of the present invention. scFv used in the present invention may be produced by acquiring cDNA encoding VH and VL from hybridoma producing a monoclonal antibody of the present invention, constructing a scFv expression vector, and causing expression by introducing the expression vector into *E. coli*, yeast or animal cell.

dsFv refers to one obtained by binding polypeptides, in which each one amino acid residue is substituted with a cysteine residue in VH and VL, via S—S bond. The amino acid to be substituted with cysteine residue may be selected based on tertiary structure prediction of antibody according to the method indicated by Reiter et al. (Protein Engineering, 7, 697 (1994)). VH or VL contained in dsFv used in the present invention may be derived from the monoclonal antibody of the present invention. dsFv used in the present invention may be produced by acquiring cDNA encoding VH and VL from hybridoma producing a monoclonal antibody of the present invention, constructing a dsFv expression vector by inserting it into an appropriate expression vector, and causing expression by introducing the expression vector into *E. coli*, yeast or animal cell.

Diabody is an antibody fragment where a dimer of scFvs having the same or different antigen binding specificity is formed, and is an antibody fragment having bivalent antigen binding activity for the same antigen or two antigen binding activities specific for different antigens. For example, bivalent Diabody that specifically reacts with the monoclonal antibody of the present invention may be produced by acquiring cDNA encoding VH and VL of a monoclonal antibody of the present invention, constructing DNA encoding scFv having a peptide linker of 3 to 10 residues, inserting the DNA into an expression vector for cell, and causing expression of Diabody by introducing the resultant expression vector into *E. coli*, yeast or animal cell.

Peptide containing CDR includes at least one region of CDR of VH or VL. Plural CDRs may be combined directly or via an appropriate peptide linker. Peptide containing CDR used in the present invention may be produced by acquiring cDNA encoding VH and VL of a monoclonal antibody of the present invention, constructing DNA encoding CDR, inserting the DNA into an expression vector for animal cell, and causing expression by introducing the resultant expression vector into *E. coli*, yeast or animal cell. Peptide containing CDR may also be produced by chemical synthesis method such as Fmoc method (fluorenyl methyloxycarbonyl method) or tBoc method (t-butyloxycarbonyl method).

A monoclonal antibody or a part thereof of the present invention may be modified insofar as it is suitably used in the present invention. As a modified substance, antibodies bound to various molecules including polyethylene glycol (PEG) or the like may be used. Modification made on antibody may be modification by introduction of chemical bond, or may be modification made on the amino acid sequence of the antibody. A monoclonal antibody or a part thereof of the present invention also embraces these antibody modified substances. For obtaining such antibody modified substances, the obtained antibody may be modified. These techniques have been already established in the art.

In another aspect, the present invention provides polynucleotide encoding heavy variable region or light variable region of humanized monoclonal antibody of the present invention. The present invention also embraces polynucleotide, which can hybridize with the said polynucleotide in a stringent condition and encodes antibody having equivalent activity with antibody of the present invention.

The polynucleotide of the present invention is polymer consisting of nucleotide such as several deoxyribonucleic acid (DNA) or ribonucleic acid (RNA), so far as encoding antibody of the present invention. These may include bases other than natural products. The polynucleotide of the invention can be available for producing antibodies in a manner of genetic technology. The polynucleotide of the invention can be also useful as probe for the screening of antibodies having equivalent activity with the antibody of the present invention. So, by using as probe polynucleotide encoding antibody of the present invention or a part thereof, applying technique such as hybridization or gene amplification technique, for example, PCR, DNA which can hybridize with said polynucleotide in the stringent condition and encodes antibody having equivalence activity with antibody of the present invention, is obtainable. Such these DNA are also embraced in the polynucleotide of the present invention.

Hybridization tequnique (Sambrook, J et al., Molecular Cloning 2nd ed., 9.47-9.58, Cold Spring Harbor Lab. press, 1989) is the well-known art for the skilled person. The condition for hybridization is for example, low-stringent condition. The low-stringent condition means washing step after hybridization is carried on under, for example, 0.1× SSC containing 0.1% SDS at 42° C., preferably 0.1×SSC containing 0.1% SDS at 50° C. More preferable hybridization condition is high-stringent. High-stringent condition means for example, under 5×SSC containing 0.1% SDS at 65° C. Under these conditions, with higher temperature, higher similarity polynucleotide is expected to be obtained efficiently. As a factor affecting stringency for hybridization, several factors such as temperature, or salt concentration, are recited. The skilled person could select these factors appropriately and could have a similar stringency.

Antibodies, functionally equivalent to antibody of the present invention, have generally high similarity in the amino acid sequence. These antibodies are encoded by polynucleotide, which are obtained with above described hybridization or gene amplification techniques. The antibodies, which are functionally equivalent to the antibody of the present invention and have high similarity in the amino acid sequence of the antibodies, are embraced in the present invention. High similarity means the similarity of at least more than 50% in the amino acid sequence, preferably the similarity of 75%, and more preferably the similarity of 85% and 95%. To determine the similarity of the polypeptide, algorithm described in the document (Wilbur, W. J. and Lipman, D. J. Proc. Natl. Acad. Sci. USA (1983) 80, 726-730) is available.

A humanized monoclonal antibody or an antibody fragment thereof of the present invention is characterized of recognizing amino acid residues at positions of 1 to 157 in the amino acid sequence of SEQ ID NO: 1 or recognizing amino acid residues at positions of 202 to 305 in the amino acid sequence of SEQ ID NO: 1. Recognizing amino acid residues at positions of 1 to 157 in the amino acid sequence of SEQ ID NO: 1 means that a monoclonal antibody recognizes an amino acid residue or amino acid residues in this region.

A humanized monoclonal antibody or an antibody fragment thereof of the present invention is useful as a pharmaceutical composition. Therefore, a pharmaceutical composition containing a humanized monoclonal antibody or an antibody fragment thereof of the present invention may be administered systemically or topically by oral or parenteral route. For parenteral administration, for example, intravenous injection such as drip infusion, intramuscular injection, intraperitoneal injection, subcutaneous injection, intranasal administration, inhalation and the like can be selected.

Also, a humanized monoclonal antibody of the present invention is applicable to the diagnostic for dyslipidemia, hyperlipidemia, arteriosclerosis, atherosclerosis, hypercholesterolemia, hypertriglyceridemia, diabetes, obesity and/or syndrome X because a humanized monoclonal antibody of the invention has the specific binding ability to against vascular endothelial lipase.

An patient of the pharmaceutical composition of the present invention is assumed arteriosclerosis and metabolic syndrome. Effective dose is selected in the range of 0.01 mg to 100 mg per 1 kg of body weight per one time. Alternatively, a dose of 5 to 5000 mg, preferably a dose of 10 to 500 mg per a patient may be selected. However, a dose of the pharmaceutical composition containing the monoclonal antibody or an antibody fragment thereof of the present invention is not limited to these doses. Administering duration may be also appropriately selected depending on the age, symptom and the like of the patient. The pharmaceutical composition of the present invention may also include a pharmaceutically acceptable carrier or additive as well depending on the route of administration. Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but, it is not limited thereto.

Reference Example 1

Preparation of Recombinant Adenovirus to Express Baboon EL

The cDNA of baboon EL with C2 tag was cloned into pShuttle vector (Clontech). This sub-cloned vector and the vector carrying adenoviral backbone gene was digested by PI-SceI and I-CeuI enzyme (Adeno-x Accessory Kit, Clontech). The ligation reaction of the digested fragments was conducted at 16° C. for 3 hrs (Ligation high, TOYOBO) and the ligation products were transformed to E. coli (OneShot stb13 Chemically Competent, Invitrogen). After selection of Ampicillin, plasmid DNA was purified from obtained clone (QIAprep spin Miniprep Kit, QIAGEN) and was digested by PacI enzyme to cut E. coli growth area (New England Biolabs). With the above, plasmid DNA was acquired to generate adenovirus vector. Acquired plasmid DNA was transfected to HEK293 cells (American Type Culture Collection) using Lipofectamine 2000 (Invitrogen) and cultured in DMEM containing 10% FBS at 37° C. After transfection, we changed culture medium every 5 days and we continued to culture cells until confirming cytopathic effect (CPE). After confirming CPE, the cells and culture supernatant were collected. After the cells were subjected to five rounds of freeze/thaw with dry ice-methanol bath and warm bath, supernatant which was obtained by 15 min centrifugation was collected as cell extracts. The culture supernatant was mixed with the culture medium and used as a primary virus stock. Amplification of the virus stock was achieved by adding the virus stock to HEK293 cells and repeating same procedures. After amplification of the virus stock, the finally obtained cell extracts was treated with Benzonase (Merck-Novagen) for 30 min at 37° C., then supernatant was used for the purification of viral vector by following density gradient centrifugation. We overlaid PBS containing 1.5, 1.35, 1.25 g/cm$^3$ cesium chloride into the centrifuging tube, then overlaid the supernatant. We centrifuged this at 35,000 rpm for 1 hr at 16° C., and collected obtained virus vector by visual. Collected viral vector was dialyzed against PBS containing 10% glycerol, and then used as purified adenoviral vectors. A part of viral vector was used for titration (Adeno-X rapid titer kit, Clontech) and self-proliferative potential gain-of-emergence decision, and only used to immunize the following only those without abnormal.

Reference Example 2

Immunization of Baboon EL Expression Adenoviral Vector 6 week-old female mice (A/J Jms Slc spices, obtained from Nihon SLC) were immunized intravenously, subcutaneously or intramuscularly with $2 \times 10^9$ i.f.u. adenovirus vector carrying baboon EL gene. Every 7 days after administration, the blood sample was taken from tail vein and the antibody titer was measured. And, additional administration of adenovirus vector carrying baboon EL gene was done intravenously, subcutaneously or intramuscularly. The mice which showed high titer were booster immunized from tail vein as the final administration.

Reference Example 3

Production of Hybridoma Producing Antibodies

The abdominal cavity of mouse which showed high titer was opened and the spleen was isolated three days after final immunization. Spleen cells and mouse myeloma cells (p3× 63-Ag8.U1, Tokyo tumor laboratories) were fused using 50% polyethylene glycol 4000, and hybridoma cells were selected in a culture medium containing hypoxanthine, aminopterin and thymidine.

Reference Example 4

Screening of a Hybridoma Cells Producing Anti-Baboon EL Antibodies

Ten days after the cell fusion, hybridoma cells which produced anti-baboon EL antibodies were selected. Each well of 384 well microtiter plates (Nunc) was immobilized with 35 μL of Tris/HCl buffer (50 mM Tris/HCl, pH 7.5) containing 0.35 μg of anti-mouse IgG-Fc (Jackson Immuno Research). The plates were incubated at 4° C. for 16 hr. After washing the wells one time with 90 μL of washing solution (saline containing 0.01% Tween20), 100 μL of Block-Ace (Dainihonsumitomo) was added to the wells and incubated at room temperature for 2 hr (immobilized plate of anti-mouse IgG-Fc antibody). After washing the wells three times with 90 μL of washing buffer, 15 μL of assay buffer containing baboon EL heparin extract (50 mM Tris/HCl, PH 7.4 containing 4% Block-Ace, 0.05% Tween20, 150 mM NaCl) were added to the wells and incubated at room temperature at 4° C. for 16 hr. After washing the wells three times with 90 μL of washing buffer, 15 μL assay buffer containing biotin-labeled anti-C2-tag antibody and HRP-labeled Streptavidin (Thermo scientific) were added to the wells and incubated at room temperature for 1 hr. After washing the wells three times with 90 μL of washing buffer, 15 μL of TMB+-Substrate-Chromogen (DAKO) was added and incubated at room temperature for 30 min. The reaction was stopped with adding 15 μL of 0.05 M $H_2SO_4$ and then measured absorbance 450 nm. From the result of screening, the 11 hybridomas (55A1, 7D4, 14A1, 2D5, 53A11, 13B3, 23H8, 16B3, 16E7, 14E1 and 19E7) which produced anti-baboon EL antibody was selected. The antibody which was produced by hybridoma of 55A1, 7D4, 14A1, 2D5, 53A11, 13B3, 23H8, 16B3, 16E7, 14E1 and 19E7 were named respectively 55A1, 7D4, 14A1, 2D5, 53A11, 13B3, 23H8, 16B3, 16E7, 14E1 and 19E7 antibody. The IgG subclasses were determined using Mouse Immunoglobulin Isotyping Kit (BD Biosciences).

The subclass of 55A1, 2D5, 53A11, 13B3, 23H8, 16B3 and 19E7 was IgG2a. The subclass of 7D4, 14A1, 16E7 and 14E1 was IgG1.

Reference Example 5

Measurement of Inhibitory Activity of Anti-EL Antibodies Against EL

Figure 1B:
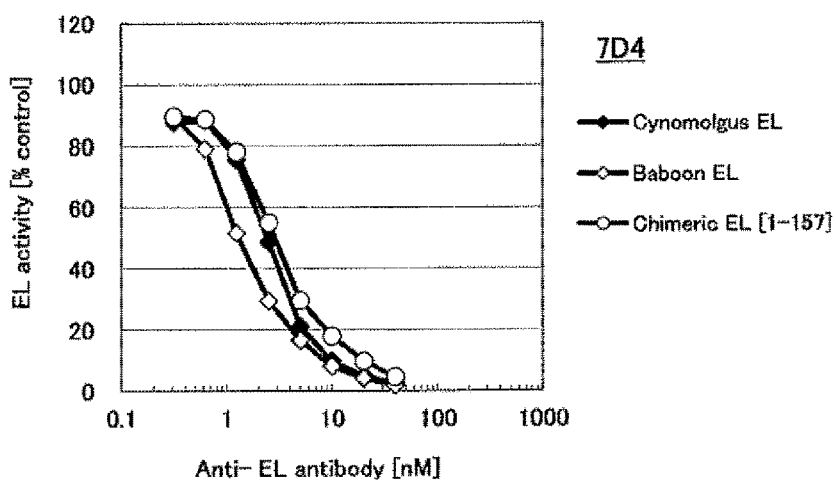
Figure 1C:
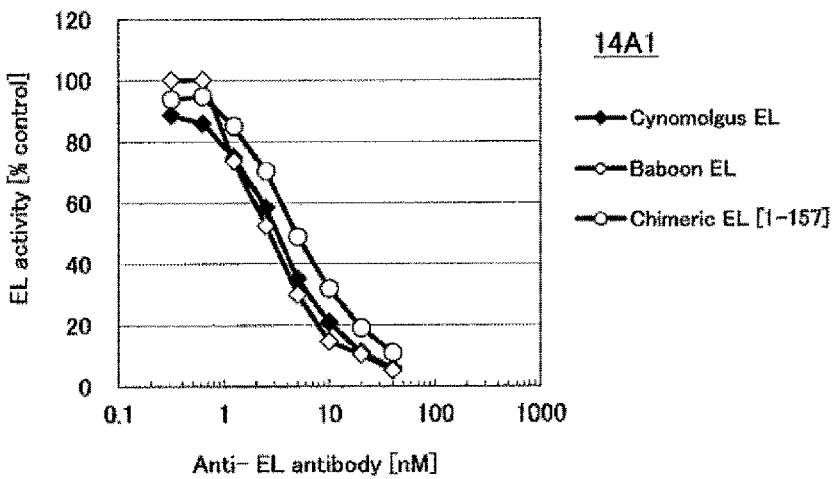
Figure 1D:
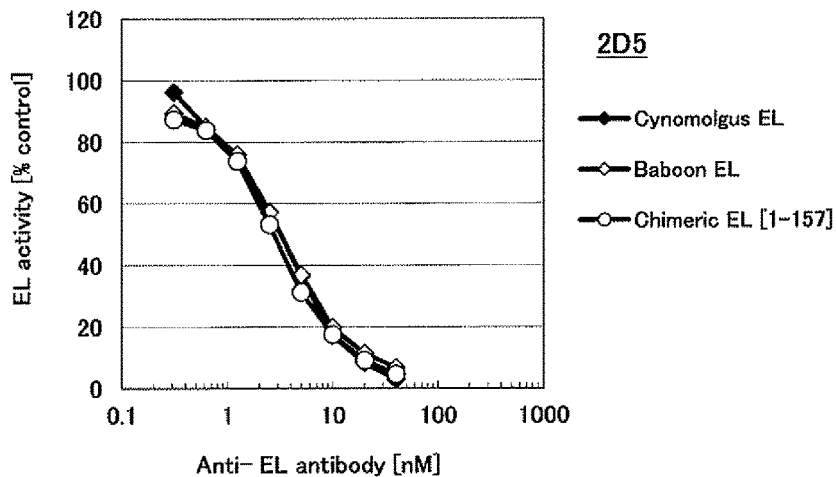
Figure 1E:
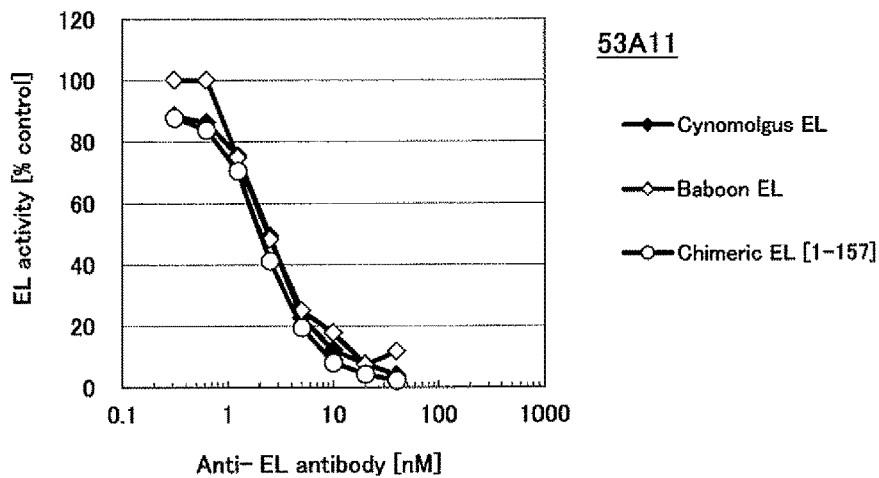
Figure 1F:
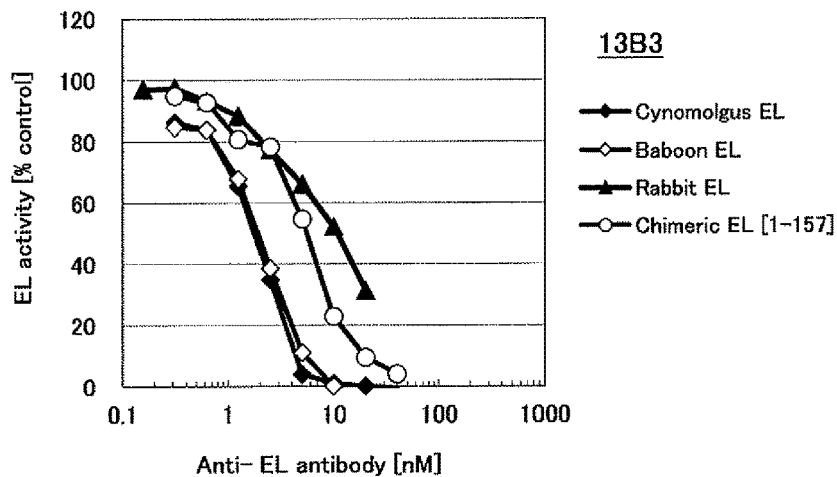
Figure 1G:
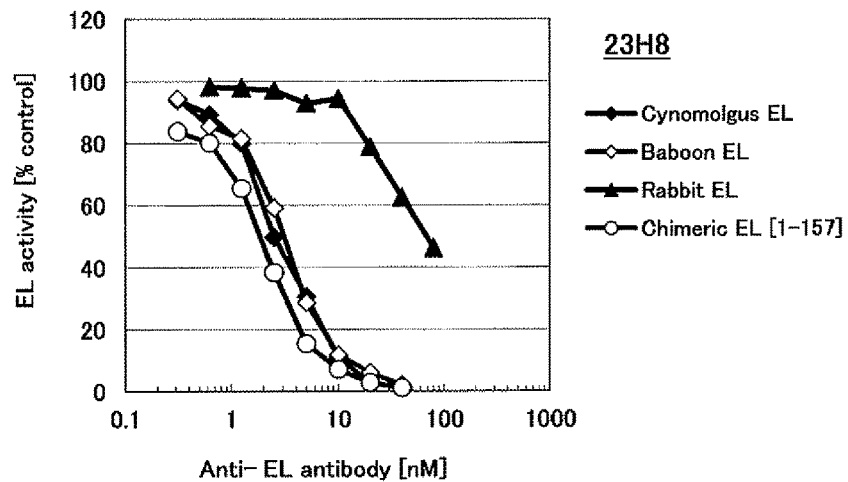
Figure 1H:
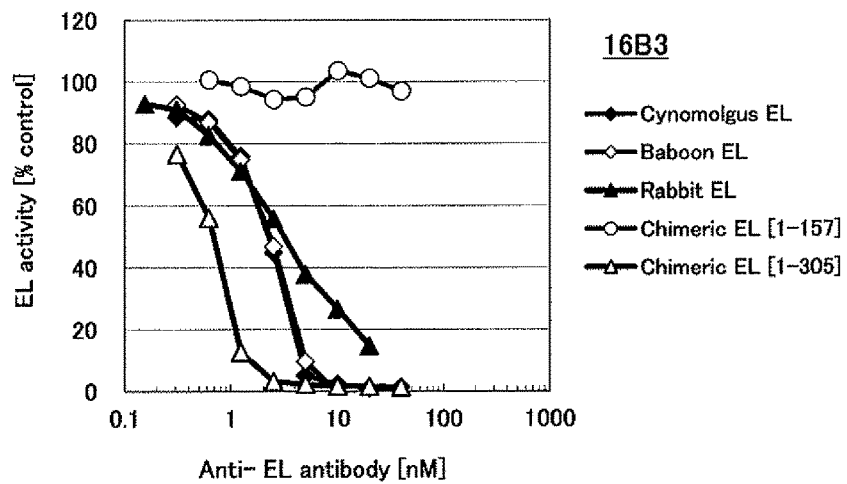
Figure 1I:
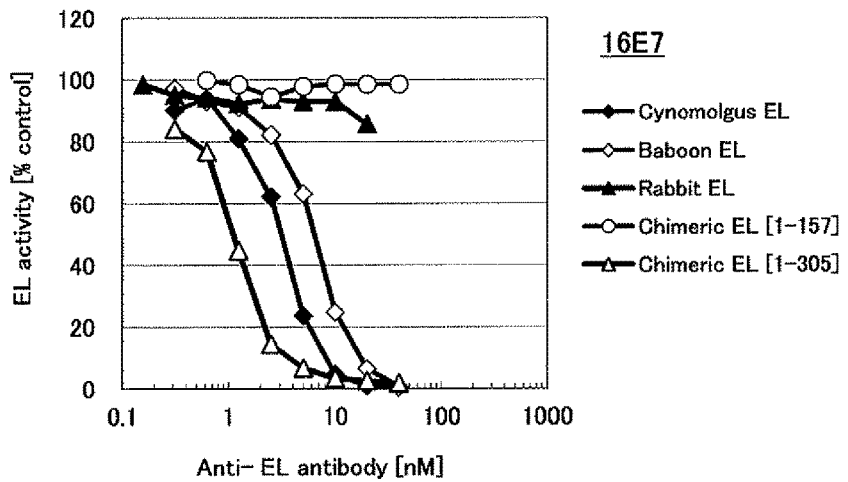
Figure 1J:
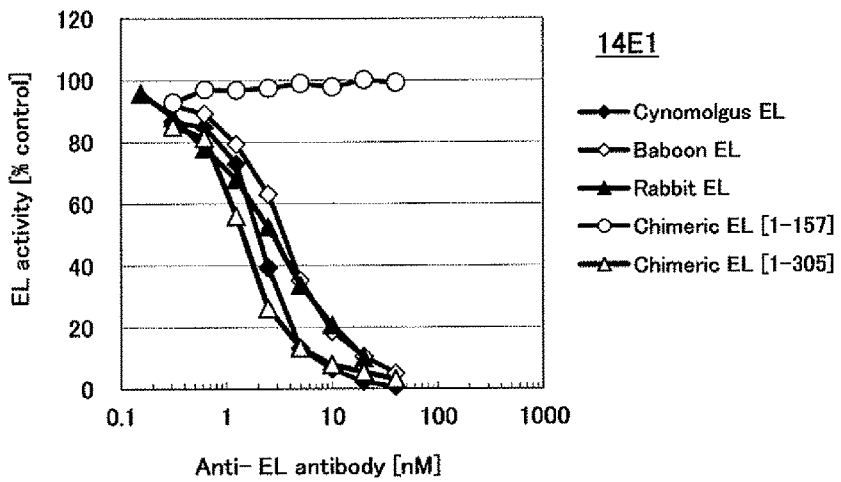
Figure 1K:
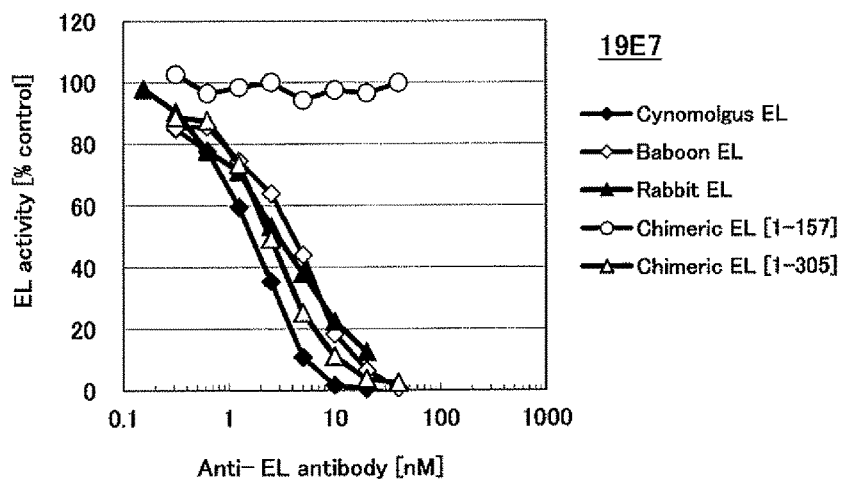

The inhibitory activity of anti-EL antibodies (55A1, 7D4, 14A1, 2D5, 53A11, 13B3, 23H8, 16B3, 16E7, 14E1 and 19E7) against baboon EL, cynomolgus monkey EL, human (1-157) mouse chimeric EL, human (1-53) mouse chimeric EL, human (61-111) mouse chimeric EL, rabbit EL, mouse EL, human (1-305) mouse chimeric EL and human (202-500) mouse chimeric EL were measured as follows. Anti-EL antibody solution, assay buffer (20 mM Tris/HCl (pH 7.5), 0.5% BSA, 4 mM $CaCl_2$), 150 mM NaCl) and 2 mg/mL human HDL (Athens Research & Technology) were mixed in a microtiter plate, followed by adding EL heparin extract. After incubation at 37° C. for 90 min, non-esterified Fatty Acid (NEFA) released from HDL was determined using a commercially available kit (NEFA C test-Wako, Wako). The NEFA amount was used as enzyme activity index. Enzyme activity in the case of adding no anti-EL antibody was determined as control value and specific activity was calculated against the control value at each concentration of the anti-EL antibody (FIG. 1A to K). The concentration of anti-EL antibody where 50% of EL activity was inhibited was calculated from the inhibition curve as IC50 value.

Reference Example 6

Measurement of Inhibitory Activity of Anti-EL Antibody Against HL and LPL

Figure 2A:
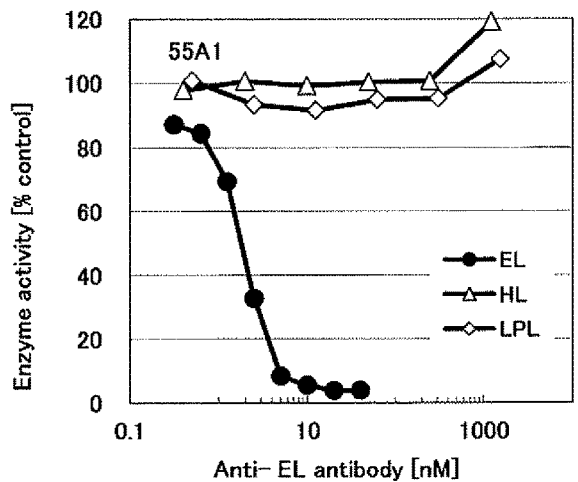
FIG. 2A to 2L show measurement results of inhibition of enzymatic activity of 55A1, 7D4, 14A1, 2D5, 53A11, 13B3, 23H8, 16B3, 16E7, 14E1, 19E7 and 16F6 antibodies against human HL and human LPL.
Figure 2B:
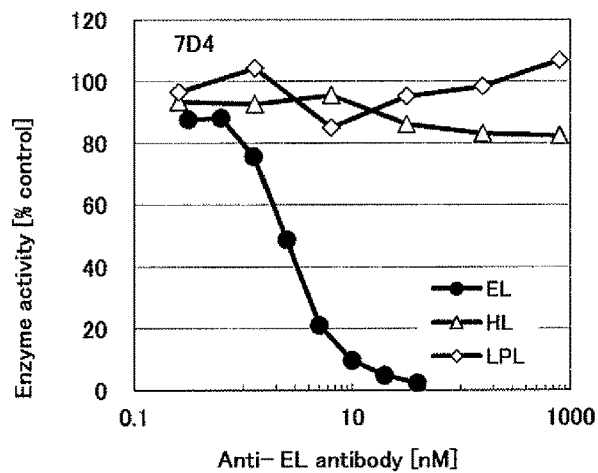
Figure 2C:
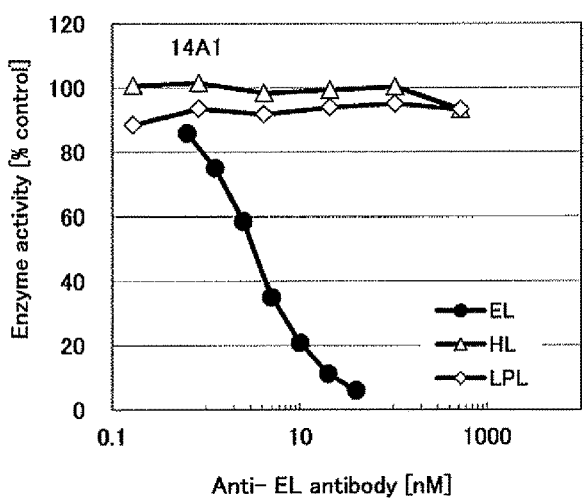
Figure 2D:
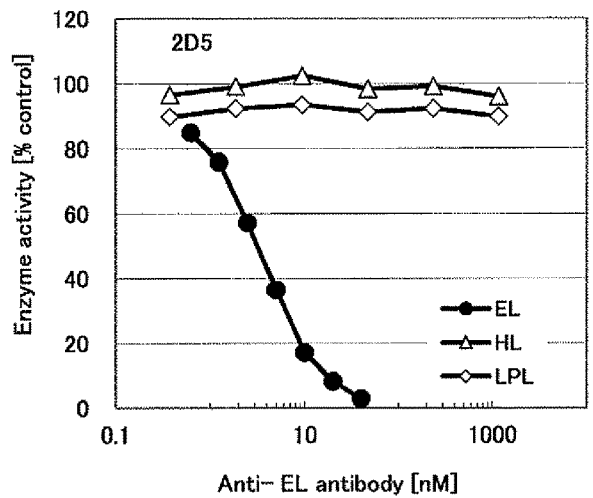
Figure 2E:
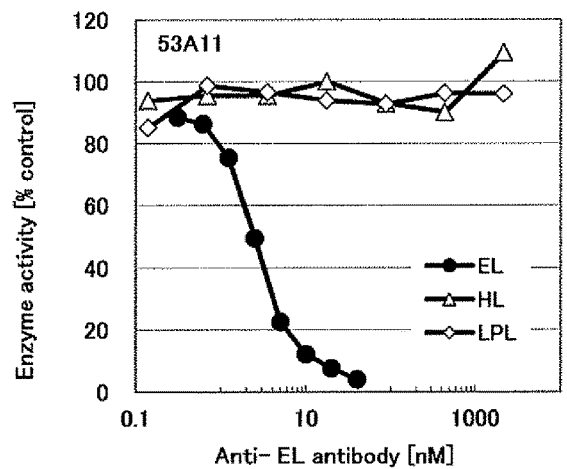
Figure 2F:
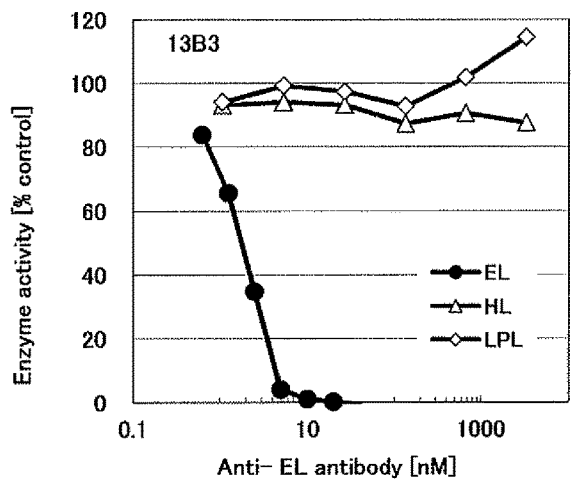
Figure 2G:
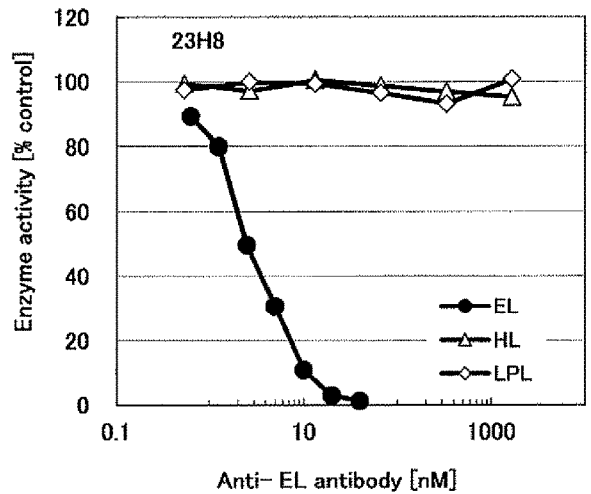
Figure 2H:
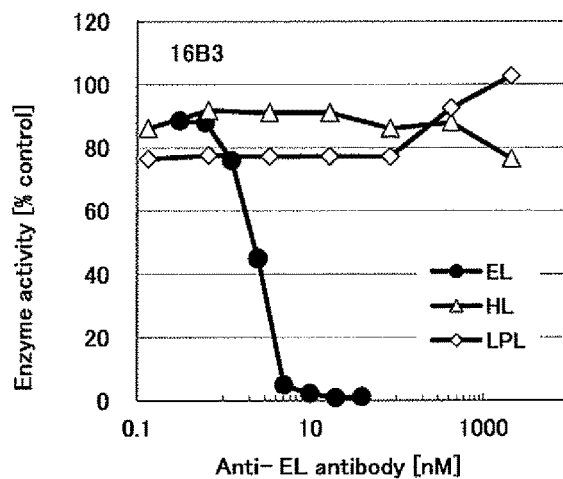
Figure 2I:
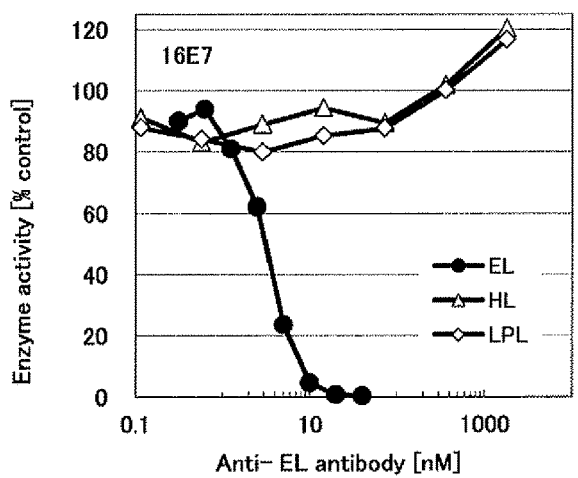
Figure 2J:
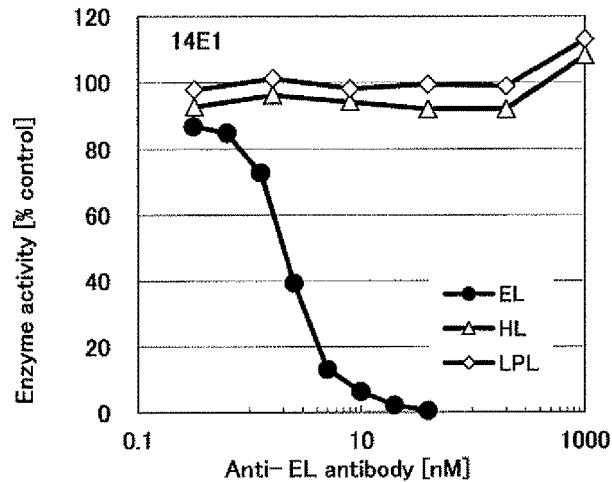
Figure 2K:
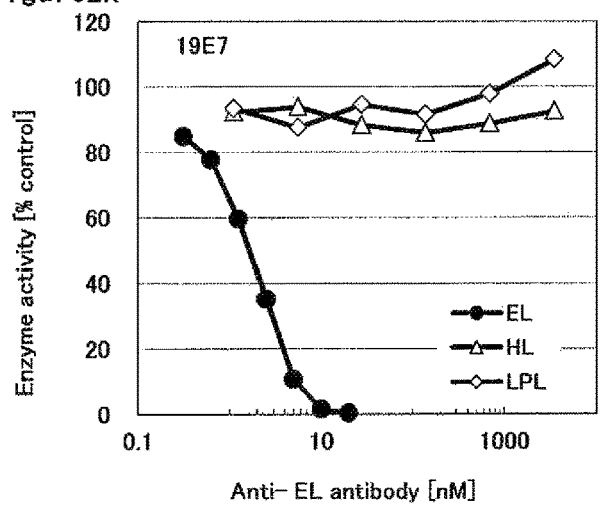
Figure 2L:
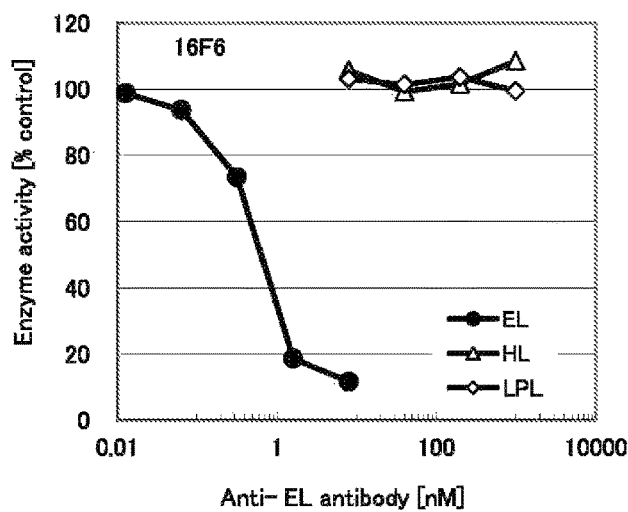

The DNA encoding human HL was cloned into pcDNA3.1 expression vector (Invitrogen). The expression vector was transfected into HEK293F cells and cultured at 37° C. 8% CO2 for 2 days. The cells were centrifuged and the cells ware collected, the cells were suspended with PBS containing 20 U/mL of Heparin (SIGMA). The cell suspension was incubated at 37° C. for 45 min. The supernatant obtained by removing cells with centrifugation was used as human HL enzyme solution. Human LPL enzyme solution was prepared by using the same method. After adding anti-EL antibody to the solution containing 20 mM Tris-HCl Buffer (pH 7.5), 0.5% bovine serum albumin, 4 mM $CaCl_2$, 150 mM NaCl and 0.5 mg/mL human VLDL (INTRACEL), human HL or human LPL enzyme was added (total volume 10 μl). After reaction at 37° C. for 2 hr, free fatty acid (NEFA) made from VLDL by HL or LPL enzyme was determined using NEFA C-test Wako (Wako), the NFFA amount was used as enzyme activity index. Enzyme activity in the case of adding no anti-EL antibody was determined as control value and the specific activity was calculated against the control value at each concentration of the antibody (FIG. 2A to K). For comparison, the result was described side by side inhibition curve of cynomolgus monkey EL. As a result, it was shown that 55A1, 7D4, 14A1, 2D5, 53A11, 13B3, 23H8, 16B3, 16E7, 14E1, 19E7 and 16F6 antibodies didn't inhibit neither HL nor LPL enzyme activity.

Reference Example 7

Measurement of Binding Activity of Anti-EL Antibody to EL

Figure 3A:
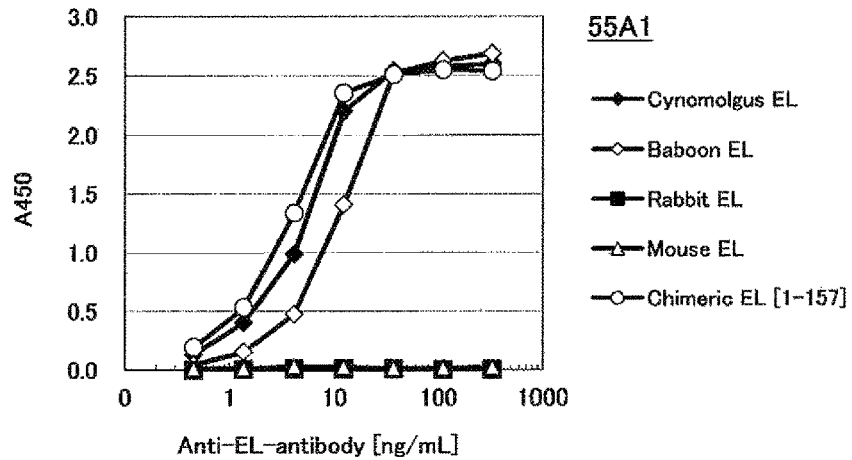
Figure 3B:
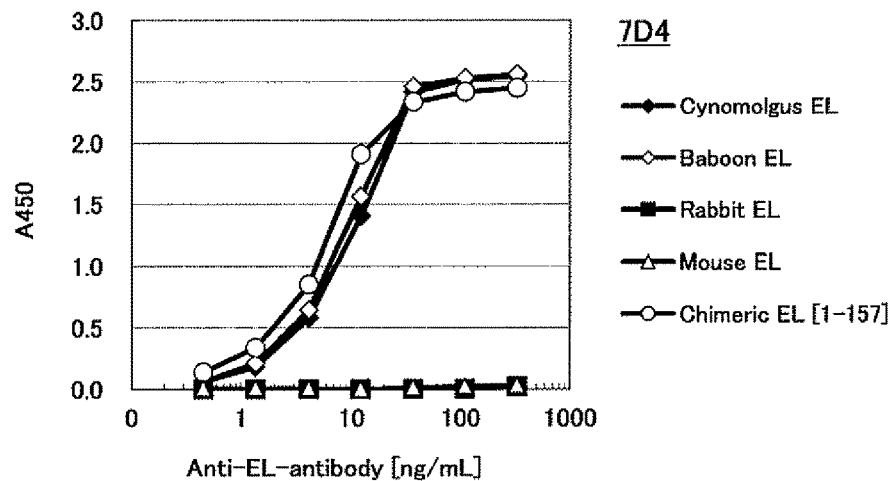
Figure 3C:
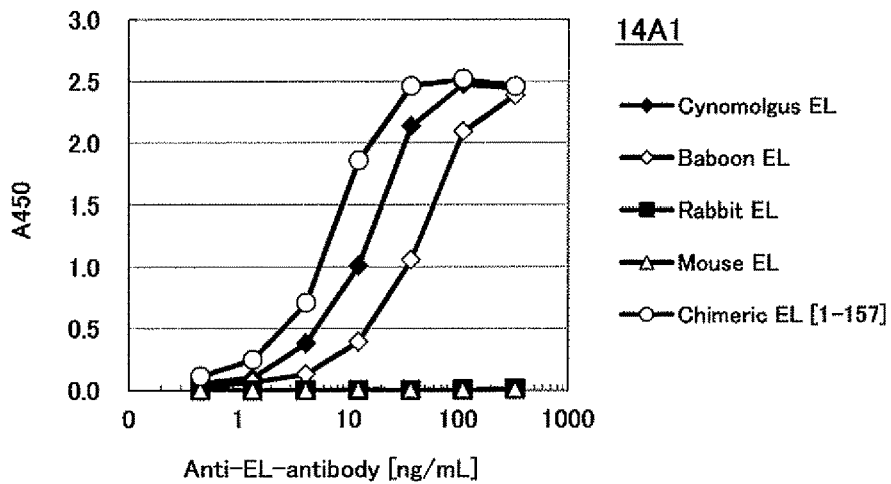
Figure 3D:
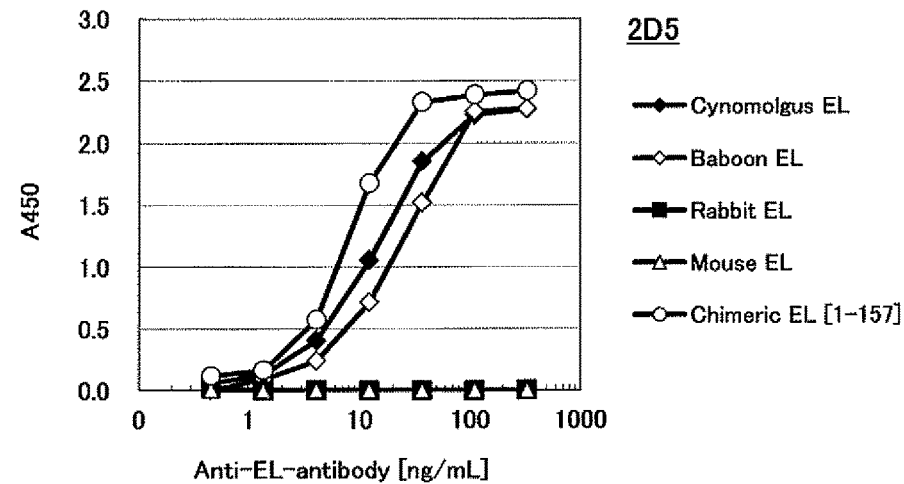
Figure 3E:
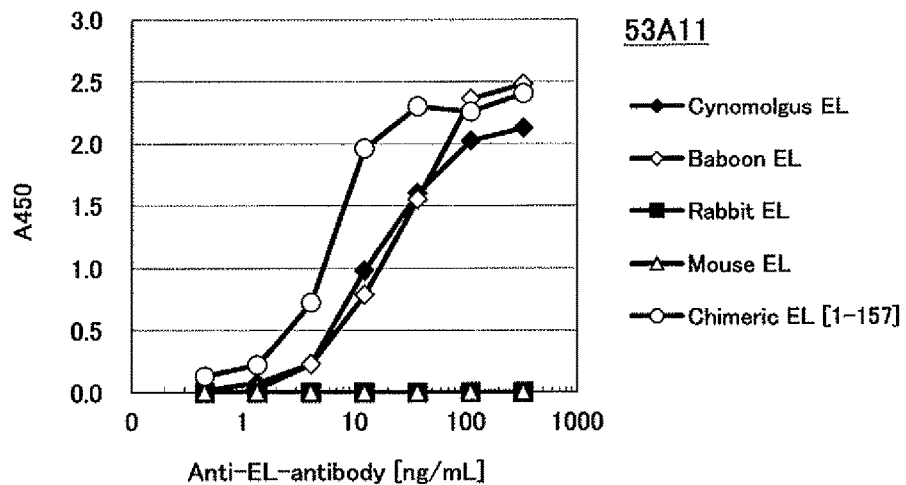
Figure 3F:
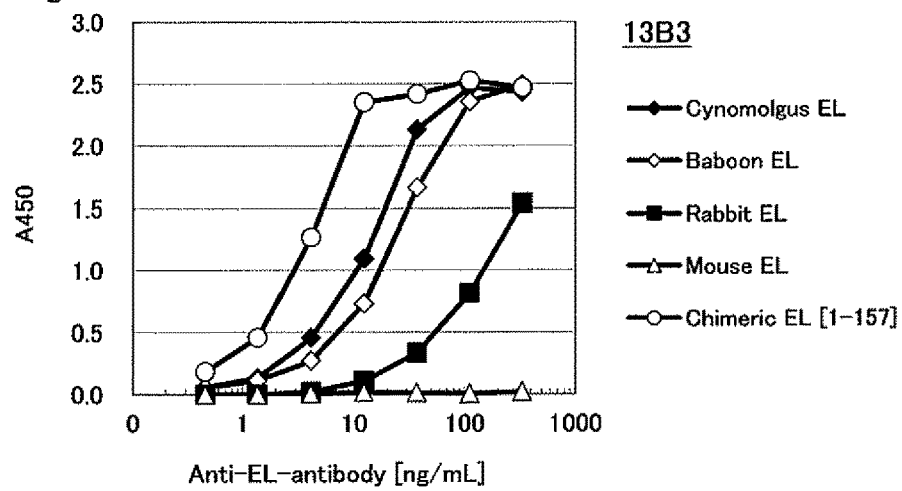
Figure 3G:
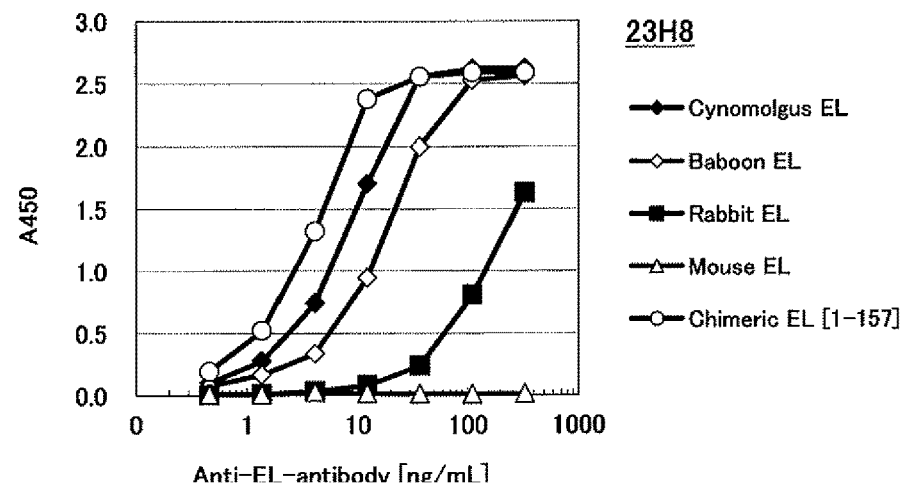
Figure 3H:
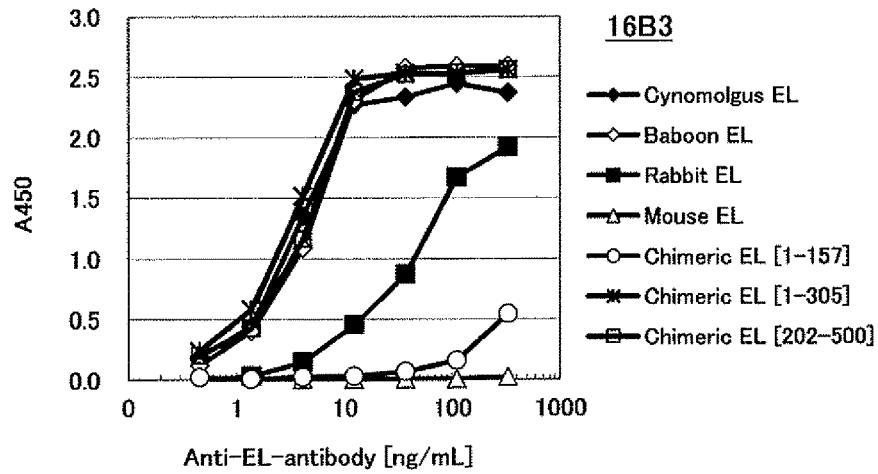
Figure 3I:
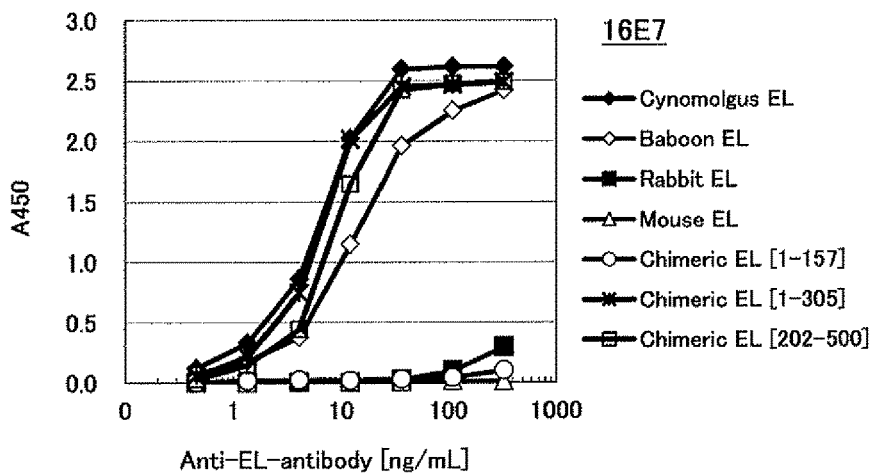
Figure 3J:
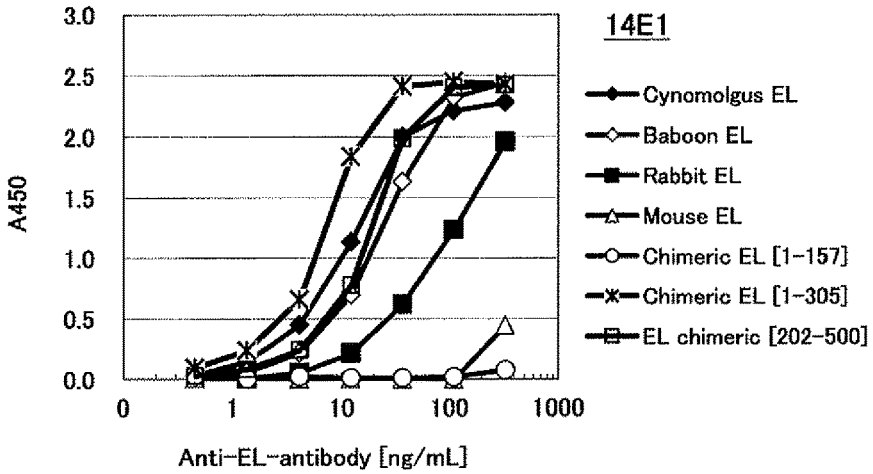

Assay buffer containing 15 μl of anti-EL antibody was added to anti-mouse IgG-Fc antibody-immobilized microtiter plate, and incubated for 2 hr. After washing the wells three times with 90 μL of washing buffer, 15 μl of cynomolgus monkey EL, baboon EL, rabbit EL, mouse EL, human [1-157]-mouse chimeric EL, human [1-305]-mouse chimeric EL or human [202-500]-mouse chimeric EL heparin extract was added and incubated at 4° C. for 16 hr. After washing the wells three times with 90 μL of washing buffer, 15 μl of assay buffer containing biotin-labeled anti-C2-tag antibody and HRP-labeled Streptavidin were added to the wells and incubated at room temperature for 1 hr. After washing the wells three times with 90 μL of washing buffer, 15 μL of TMB+-Substrate-Chromogen (DAKO) was added and incubated at room temperature for 30 min and then 15 μL of 0.05 M H2SO4 was added and absorbance at 450 nm was measured (FIG. 3A to 3K).

As a result, 55A1, 7D4, 14A1, 2D5, 53A11, 13B3 and 23H8 bound cynomolgus monkey EL, baboon EL and human [1-157]-mouse chimeric EL, but did not bind mouse EL. In addition, 13B3 and 23H8 bound rabbit EL, but 55A1, 7D4, 14A1 2D5 and 53A11 did not. On the other hand, 16B3, 16E7, 14E1 and 19E7 bound cynomolgus monkey EL, baboon EL, human [1-305]-mouse chimeric EL and human [202-500]-mouse chimeric EL, but did not bind mouse El and human [1-157]-mouse chimeric EL. In addition, 16B3, 14E1 and 19E7 bound rabbit EL, but 16E7 did not.

Reference Example 8

Binding Affinities of Anti-EL Antibodies

The binding affinities of anti-EL antibodies were measured using Biacore. Anti-C2-tag antibody was immobilized on a sensor chip CMS (GE HealthCare) using amine-coupling and baboon EL, cynomolgus monkey EL or human [1-305]-mouse chimeric EL heparin extract was added and EL was captured on the sensor chip. Then, anti-EL antibodies were added and the binding affinities were calculated by bivalent fitting of BIAevaluation software. The results were summarized in Table 1 to 3.

TABLE 1

| Affinity for Baboon EL | | | |
|---|---|---|---|
| Clone name | ka [1/Ms] | kd [1/s] | $K_D$ [M] |
| 55A1 | $3.5 \times 10^5$ | $4.2 \times 10^{-4}$ | $1.2 \times 10^{-9}$ |
| 7D4 | $7.8 \times 10^4$ | $3.5 \times 10^{-4}$ | $4.5 \times 10^{-9}$ |
| 14A1 | $1.9 \times 10^5$ | $6.2 \times 10^{-4}$ | $3.3 \times 10^{-9}$ |
| 2D5 | $7.7 \times 10^5$ | $1.7 \times 10^{-4}$ | $2.2 \times 10^{-9}$ |

TABLE 1-continued

Affinity for Baboon EL

| Clone name | ka [1/Ms] | kd [1/s] | $K_D$ [M] |
|---|---|---|---|
| 53A11 | $1.7 \times 10^5$ | $2.6 \times 10^{-4}$ | $1.6 \times 10^{-9}$ |
| 13B3 | $6.1 \times 10^4$ | $3.1 \times 10^{-4}$ | $5.1 \times 10^{-9}$ |
| 23H8 | $1.5 \times 10^5$ | $4.4 \times 10^{-4}$ | $2.9 \times 10^{-9}$ |
| 16B3 | $3.1 \times 10^4$ | $9.8 \times 10^{-5}$ | $3.2 \times 10^{-9}$ |
| 16E7 | $5.3 \times 10^4$ | $2.5 \times 10^{-4}$ | $4.7 \times 10^{-9}$ |
| 14E1 | $1.5 \times 10^5$ | $8.5 \times 10^{-4}$ | $5.8 \times 10^{-9}$ |
| 19E7 | $6.7 \times 10^4$ | $8.3 \times 10^{-4}$ | $1.2 \times 10^{-9}$ |

TABLE 2

Affinity for Cynomolgus EL

| Clone name | ka [1/Ms] | kd [1/s] | $K_D$ [M] |
|---|---|---|---|
| 55A1 | $2.5 \times 10^5$ | $4.4 \times 10^{-4}$ | $1.7 \times 10^{-9}$ |
| 7D4 | $1.2 \times 10^5$ | $2.3 \times 10^{-4}$ | $1.9 \times 10^{-9}$ |
| 14A1 | $2.1 \times 10^5$ | $8.1 \times 10^{-4}$ | $3.9 \times 10^{-9}$ |
| 2D5 | $7.4 \times 10^5$ | $2.8 \times 10^{-4}$ | $3.8 \times 10^{-9}$ |
| 53A11 | $9.1 \times 10^5$ | $3.8 \times 10^{-4}$ | $4.2 \times 10^{-9}$ |
| 13B3 | $4.7 \times 10^4$ | $4.1 \times 10^{-4}$ | $8.7 \times 10^{-9}$ |
| 23H8 | $1.2 \times 10^5$ | $7.5 \times 10^{-4}$ | $6.1 \times 10^{-9}$ |
| 16B3 | $4.2 \times 10^5$ | $8.9 \times 10^{-5}$ | $2.1 \times 10^{-9}$ |
| 16E7 | $3.2 \times 10^4$ | $3.2 \times 10^{-4}$ | $3.7 \times 10^{-9}$ |
| 14E1 | $1.2 \times 10^5$ | $6.9 \times 10^{-4}$ | $5.9 \times 10^{-9}$ |
| 19E7 | $5.5 \times 10^4$ | $1.8 \times 10^{-4}$ | $3.3 \times 10^{-9}$ |

TABLE 3

Affinity for Human[1-305]-mouse chimeric EL

| No. | Clone name | ka [1/Ms] | kd [1/s] | $K_D$ [nM] |
|---|---|---|---|---|
| 1 | 55A1 | $1.9 \times 10^5$ | $1.4 \times 10^{-4}$ | $7.3 \times 10^{-10}$ |
| 2 | 7D4 | $1.1 \times 10^5$ | $1.1 \times 10^{-4}$ | $9.7 \times 10^{-10}$ |
| 3 | 14A1 | $2.1 \times 10^5$ | $1.0 \times 10^{-4}$ | $5.0 \times 10^{-10}$ |
| 4 | 2D5 | $8.5 \times 10^4$ | $9.3 \times 10^{-5}$ | $1.1 \times 10^{-9}$ |
| 5 | 53A11 | $1.8 \times 10^5$ | $1.1 \times 10^{-4}$ | $6.3 \times 10^{-10}$ |
| 6 | 13B3 | $1.5 \times 10^5$ | $1.4 \times 10^{-4}$ | $9.1 \times 10^{-10}$ |
| 7 | 23H8 | $1.2 \times 10^5$ | $1.1 \times 10^{-4}$ | $8.7 \times 10^{-10}$ |
| 8 | 16B3 | $5.1 \times 10^4$ | $1.9 \times 10^{-4}$ | $3.7 \times 10^{-9}$ |
| 9 | 16E7 | $9.5 \times 10^5$ | $1.0 \times 10^{-4}$ | $1.1 \times 10^{-9}$ |
| 10 | 14E1 | $4.2 \times 10^4$ | $2.3 \times 10^{-4}$ | $5.4 \times 10^{-9}$ |

From the results of Reference example 5 to 8, the characteristics of anti-EL antibodies were summarized in Table 4.

TABLE 4

| | | Neutralizing activity IC50 [nM] | | | | a region of EL |
|---|---|---|---|---|---|---|
| No. | Clone name | Subclass | baboon EL | human-mouse chimeric EL | cynomolgus monkey EL | rabbit EL | which contributes to antibody binding |
| 1 | 55A1 | IgG2a | 2.0 | 1.1 | 1.5 | N.T. | 1-157 |
| 2 | 7D4 | IgG1 | 2.6 | 3.7 | 2.1 | N.T. | 1-157 |
| 3 | 14A1 | IgG1 | 2.7 | 5.8 | 3.1 | N.T. | 1-157 |
| 4 | 2D5 | IgG2a | 2.9 | 2.7 | 3.0 | N.T. | 1-157 |
| 5 | 53A11 | IgG2a | 2.4 | 2.3 | 1.9 | N.T. | 1-157 |
| 6 | 13B3 | IgG2a | 2.6 | 4.1 | 1.7 | 13 | 1-157 |
| 7 | 23H8 | IgG2a | 3.2 | 1.7 | 2.7 | 67 | 1-157 |
| 8 | 16B3 | IgG2a | 3.0 | 1.3 | 1.9 | 6.3 | 202-305 |
| 9 | 16E7 | IgG1 | 2.1 | 1.1 | 2.5 | >40 | 202-305 |
| 10 | 14E1 | IgG1 | 3.3 | 1.4 | 2.4 | 5.9 | 202-305 |
| 11 | 19E7 | IgG2a | 2.0 | 2.4 | 1.7 | 5.7 | 202-305 |

Reference Example 9

Generation of Anti-EL Antibody Binding to Both Human and Mouse EL

The adenovirus which expresses mouse EL was obtained using the same method as Example 1 and immunized to EL knock-out mice. In the same manner as Example 4 and 5, anti-EL antibody (16F6) was achieved and subclass was IgG1. The neutralizing activity and binding affinity of 16F6 were measured and described in Table 5 and 6.

TABLE 5

| Clone name | EL | neutralizing activity IC50 [nM] |
|---|---|---|
| 16F6 | baboon EL | 2.8 |
| | human (1-305) mouse chimeric EL | 4.0 |
| | mouse EL | 2.5 |
| | rabbit EL | 2.3 |

TABLE 6

| Clone name | EL | Affinity | | |
|---|---|---|---|---|
| | | ka [1/Ms] | kd [1/s] | $K_D$ [M] |
| 16F6 | human [1-305] mouse chimeric EL | $3.3 \times 10^5$ | $4.0 \times 10^{-3}$ | $1.4 \times 10^{-8}$ |
| | mouse EL | $2.2 \times 10^5$ | $1.5 \times 10^{-4}$ | $6.8 \times 10^{-10}$ |
| | baboon EL | $2.4 \times 10^5$ | $1.0 \times 10^{-4}$ | $4.2 \times 10^{-10}$ |

Reference Example 10

Determination of EL Regions Contributing to Antibody Binding

Figure 7B:
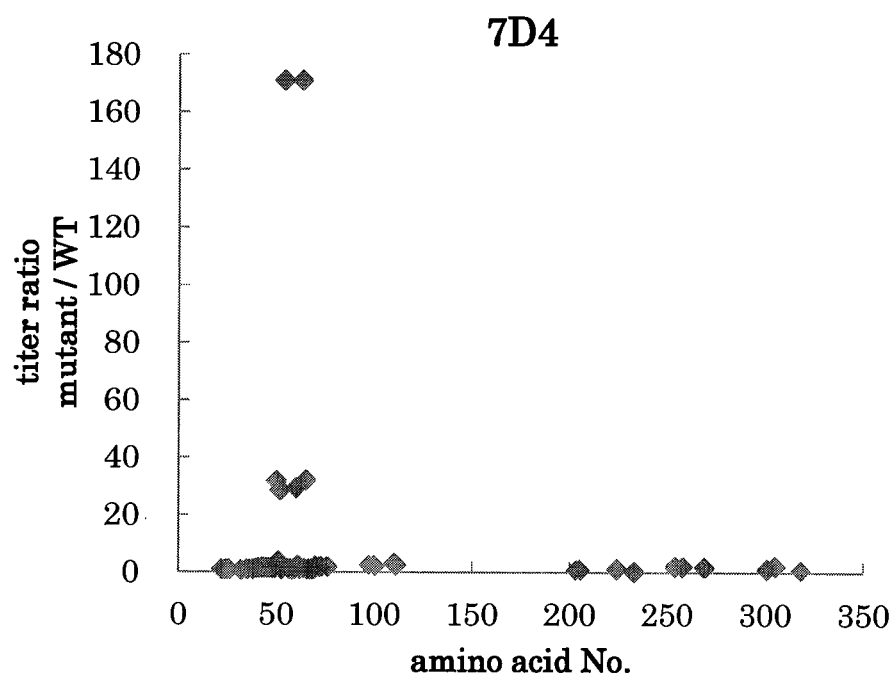
Figure 7C:
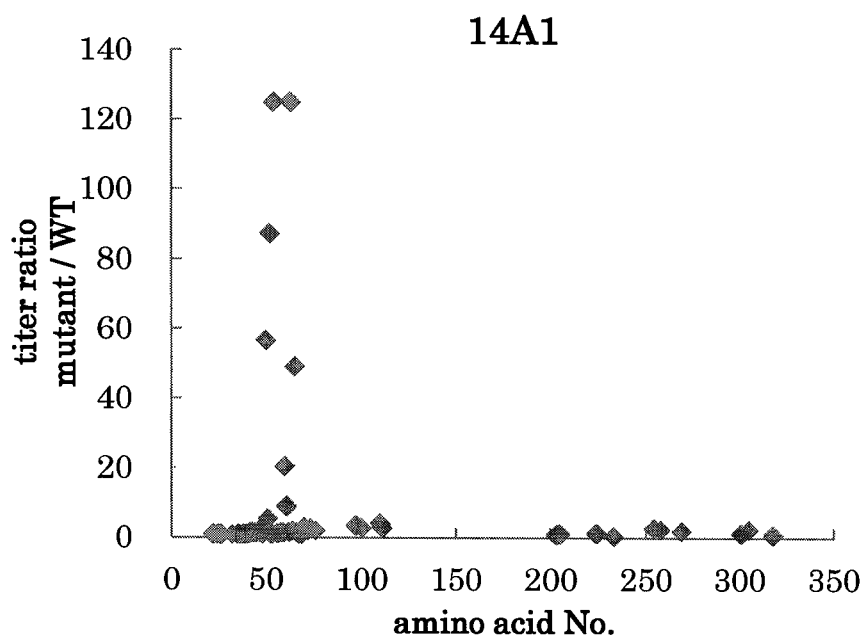
Figure 7D:
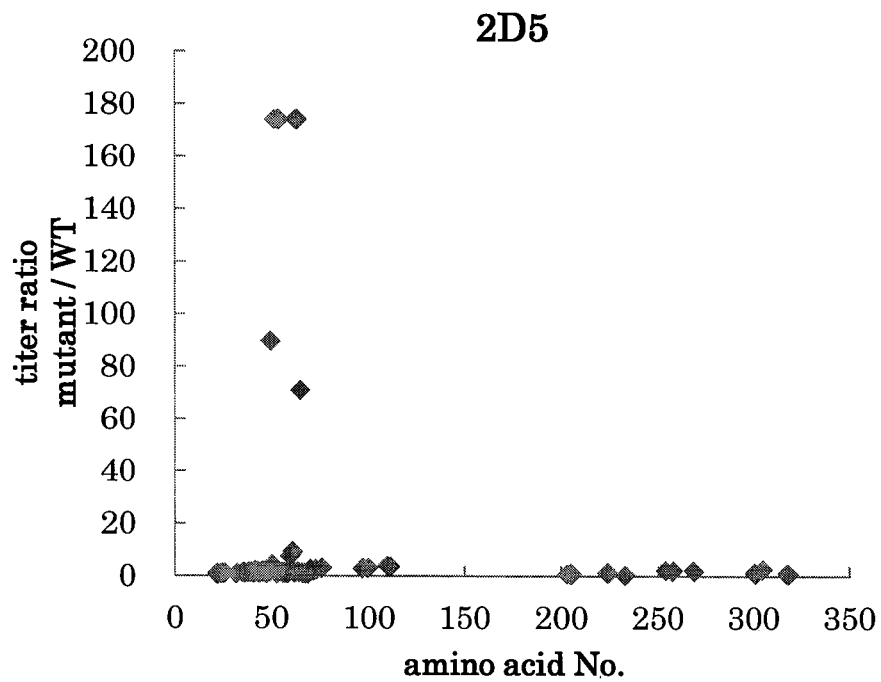
Figure 7E:
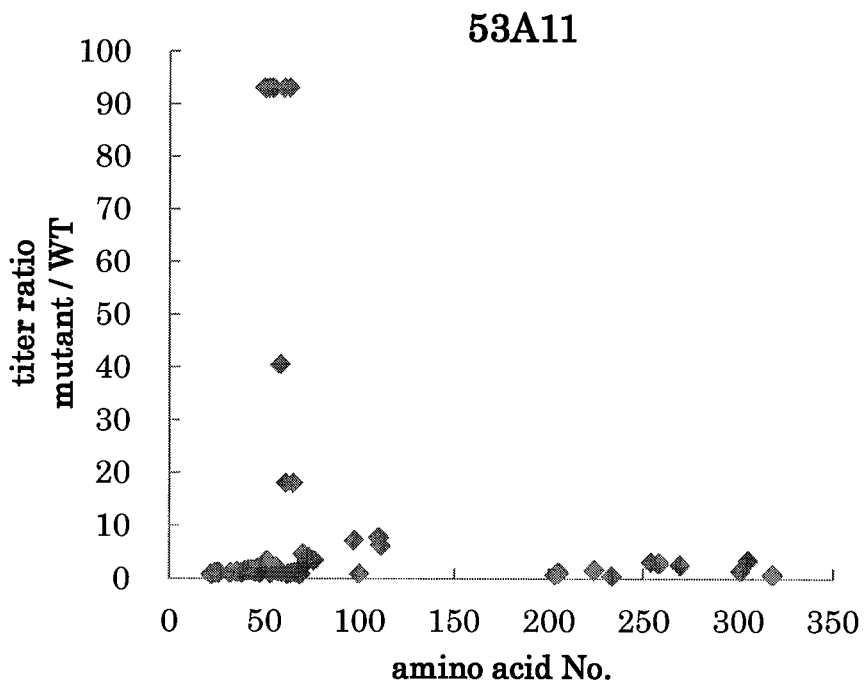
Figure 7F:
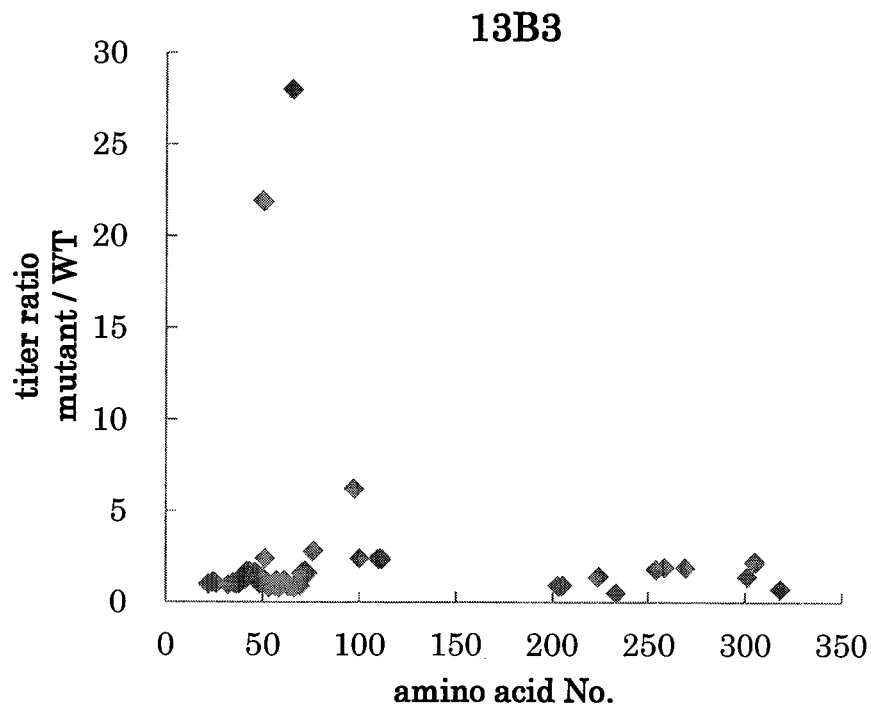
Figure 7G:
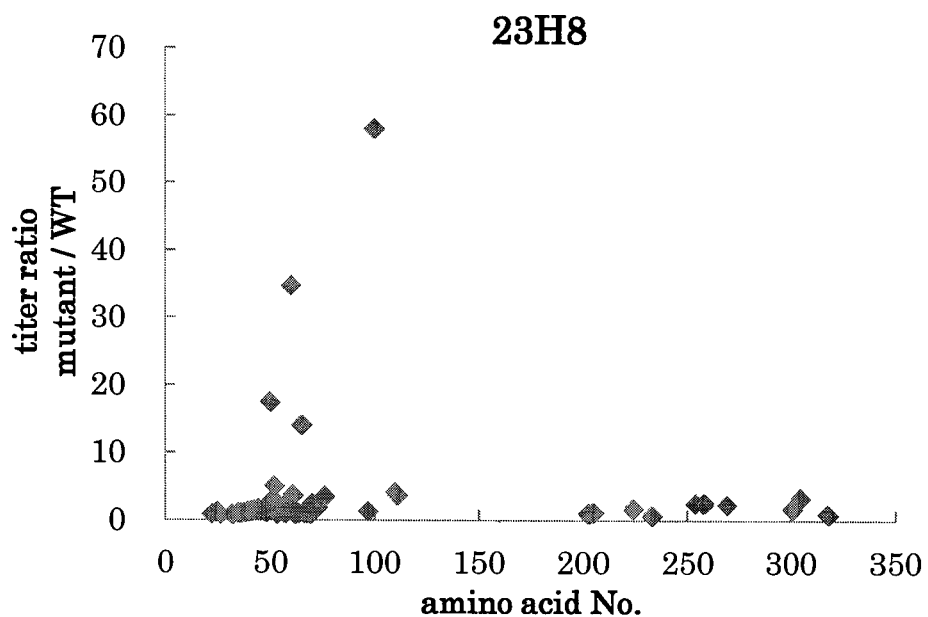
Figure 7H:
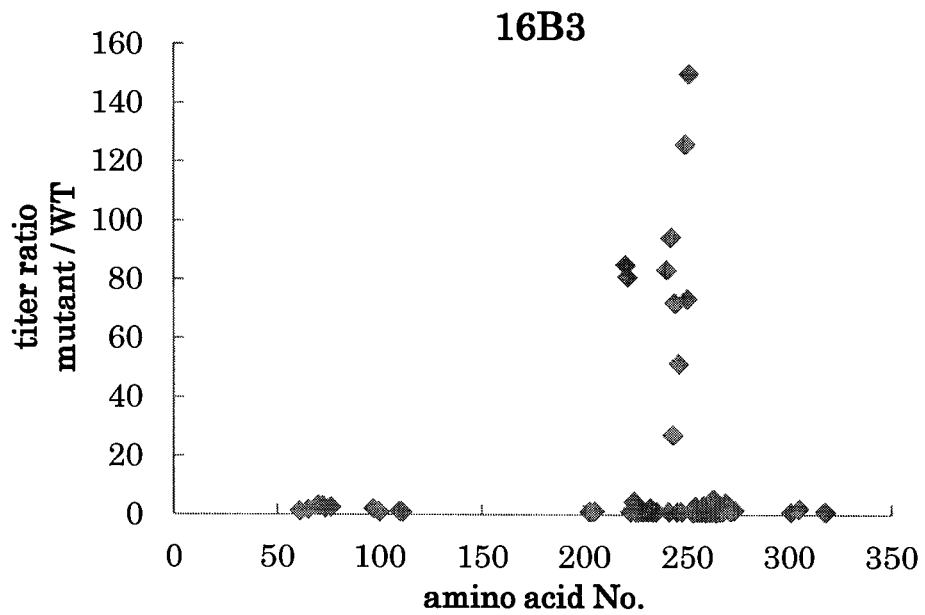
Figure 7I:
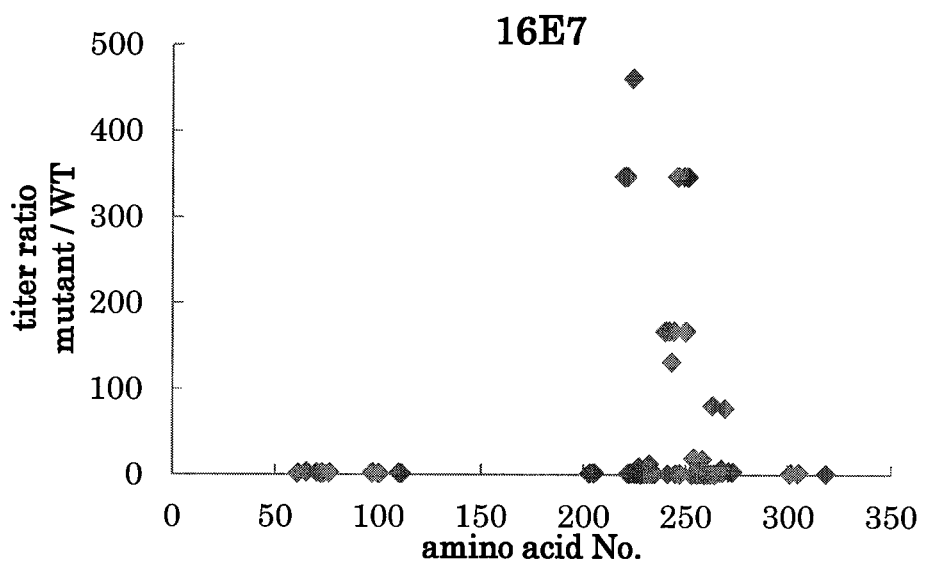
Figure 7J:
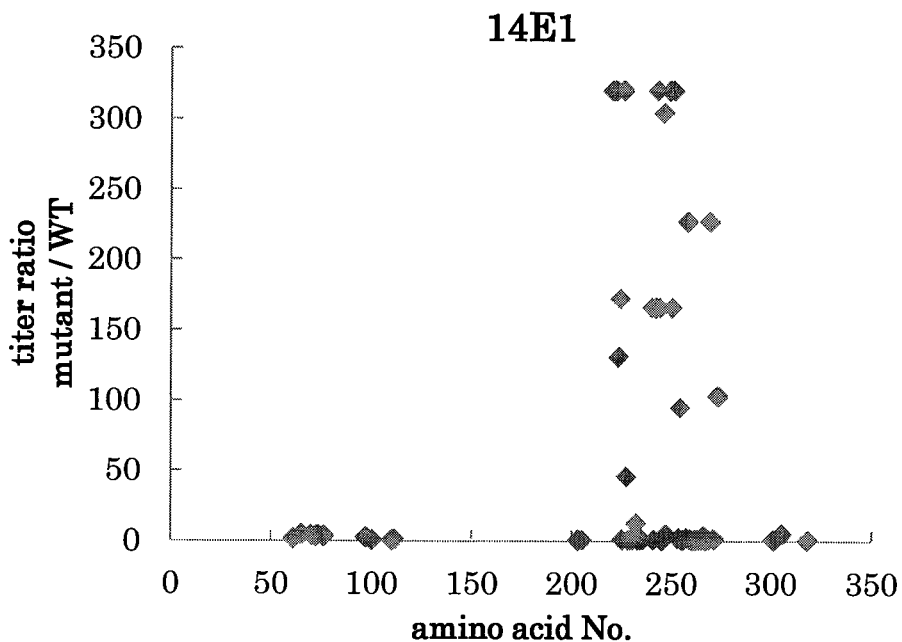
Figure 7K:
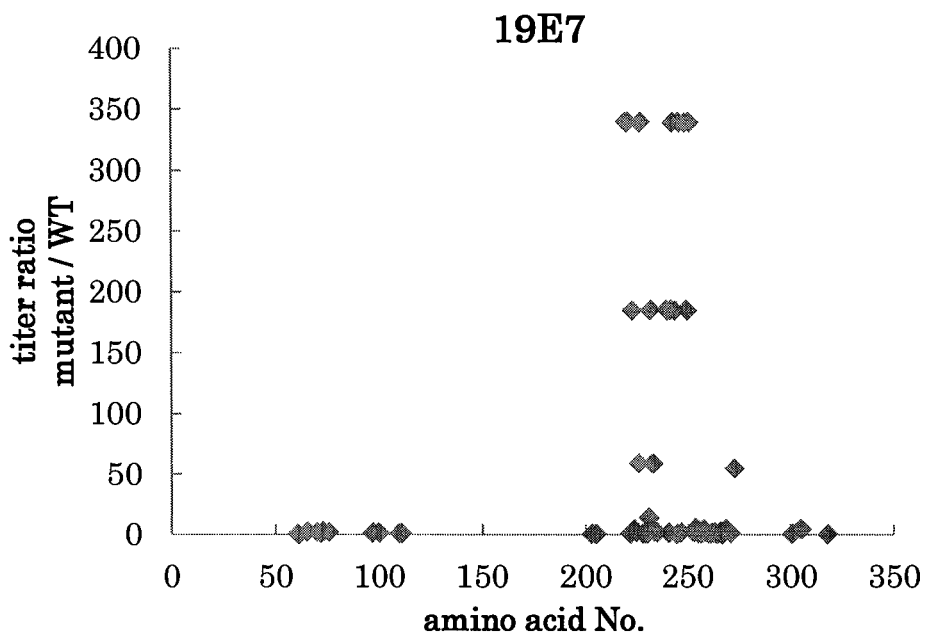
Figures 7L, 8A:
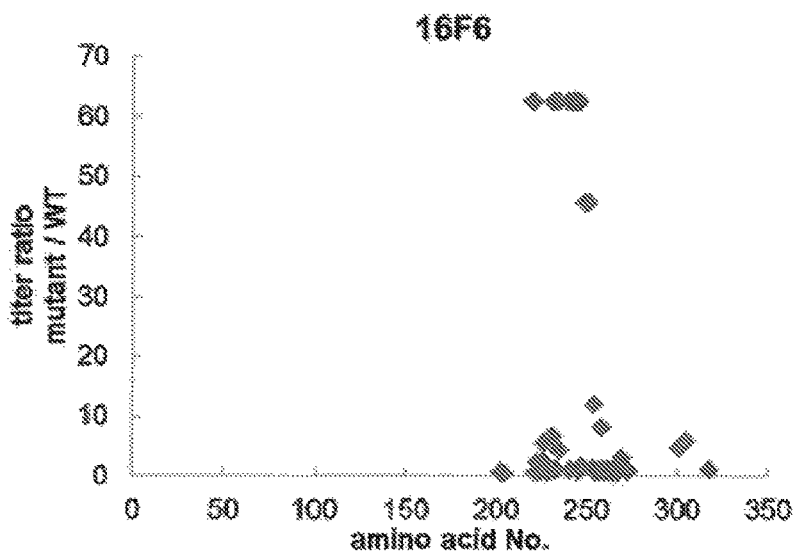

The EL region which contributes to antibody binding was determined by the homology-scanning mutagenesis or alanine scanning mutagenesis. The binding activity of anti-EL antibody to EL mutant was analyzed by ELISA. The amino acid residues of baboon EL were mutated to alanine using QuikChange Site-Directed Mutagenesis Kit (Agilent Technologies), but the amino acid residues which were different from baboon EL and mouse EL were mutated to mouse EL amino acid residues. Mutated EL heparin extracts were prepared and binding activity to anti-EL antibody according to Example 2 and Example 8. The relative effect of each mutation was evaluated from the following formula; ([antibody concentration where A450 value showed 1.0]-mutated EL)/([antibody concentration where A450 value showed 1.0]-wild type EL). The relative binding activity of mutated baboon EL to anti-EL antibodies (55A1, 7D4, 14A1, 2D5, 53A11, 13B3 or 23H8) was showed in FIG. 7A to G The relative binding activity of mutated baboon EL to anti-EL antibodies (16B3, 16E7, 14E1, 19E7 or 16F6) was also showed in FIG. 7H to L.

From the information of FIG. 7A to 7G, it was shown that important amino acids in the binding of the 55A1, 7D4, 14A1, 2D5, 53A11, 13B3 or 23H8 antibody and EL are arginine at position 50, glutamic acid at position 60, histidine at position 61, tyrosine at position 65 and asparagine at position 100 in the amino acid sequence of SEQ ID NO: 1.

From the information of FIG. 7H to 7K, it was shown that important amino acids in the binding of the 16B3, 16E7, 14E1 or 19E7 antibody and EL are histidine at position 220, threonine at position 221, tyrosine at position 222, threonine at position 223, arginine at position 224, phenylalanine at position 226, glycine at position 227, glycine at position 231, isoleucine at position 232, glutamine at position 233, methionine at position 234, aspartic acid at position 240, tyrosine at position 242, proline at position 243, asparagine at position 244, glycine at position 246, glutamine at position 249, proline at position 250, glycine at position 251, leucine at position 254, leucine at position 258, tyrosine at position 263, valine at position 269 and glutamic acid at position 273 in the amino acid sequence of SEQ ID NO: 1.

Reference Example 11

Analysis of the Amino Acid Sequence of Variable Region of Anti-EL Antibodies

The amino acid sequence of variable region of anti-EL antibody was determined using conventional procedure and described in FIG. 4A to L.

The present invention is described below in more detail by the way of examples. However, the present invention is not limited to the following examples. Unless specifying otherwise as a procedure for preparing antibody, we used methods described in Immunochemistry in Practice (Blackwell Scientific Publications). Also unless specifying otherwise as the genetic engineering techniques, we used methods described in Molecular Cloning: A Laboratory Manual, $2^{nd}$ Edition (Cold Spring Harbor Laboratory).

Example 1

Humanization of Mouse Monoclonal Antibody

The seven mouse monoclonal antibodies (16B3, 55A1, 53A11, 23H8, 13B3 and 16F6) which were generated as described above and 12B10 which was described in WO2013/054830 were humanized. More specifically, humanization was performed by inserting the sequence of humanized variable region which is grafted CDRs of each mouse antibody into the pcDNA based plasmid encoding the constant region of human kappa or human gamma1 domain sequences.

In a same manner as described above, eleven humanized antibodies h16B3-S1, h16B3-52, h16B3-S3, h16B3-54, h16B3-S5, h1683-S6, h16B3-S7, h16B3-58, h16B3-F1, h16B3-F2 and h16B3-F3 were generated derived from mouse 16B3. The alignments of variable region of these humanized antibodies were shown in FIG. 8A to D.

In a same manner as described above, thirteen humanized antibodies h55A1-S1, h55A1-S2, h55A1-S3, h55A1-S4, h55A1-S5, h55A1-S6, h55A1-S7, h55A1-F1, h55A1-F2, h55A1-F3, h55A1-F4, h55A1-F5 and h55A1-F6 were generated derived from mouse 55A1. The alignments of variable region of these humanized antibodies were shown in FIG. 9A to D.

In a same manner as described above, four humanized antibodies h53A11-S1, h53A11-S2, h53A11-S3 and h53A11-S4 were generated derived from mouse 53A11. The alignments of variable region of these humanized antibodies were shown in FIG. 10A to B.

In a same manner as described above, three humanized antibodies h23H8-S1, h23H8-S2 and h23H8-S3 were generated derived from mouse 23H8. The alignments of variable region of these humanized antibodies were shown in FIG. 11A to B.

In a same manner as described above, four humanized antibodies h13B3-S1, h13B3-S2, h13B3-S3 and h13B3-S4 were generated derived from mouse 13B3. The alignments of variable region of these humanized antibodies were shown in FIG. 12A to B.

In a same manner as described above, four humanized antibodies h12B10-S1, h12B10-S2, h12B10-S3 and h12B10-S4 were generated derived from mouse 12B10. The alignments of variable region of these humanized antibodies were shown in FIG. 13A to B.

In a same manner as described above, five humanized antibodies h16F6-S1, h16F6-S2, h16F6-S3, h16F6-S4 and h16F6-S5 were generated derived from mouse 16F6. The alignments of variable region of these humanized antibodies were shown in FIGS. 14A to B.

The amino acid sequence of variable region of these forty four humanized antibodies were summarized in Table 7-1 to 7-2, and shown in FIGS. 15 to 21.

TABLE 7

| | Heavy chain | | | Light chain | | |
|---|---|---|---|---|---|---|
| mAb | VH | JH | Mutation | VK | JK | Mutation |
| h16B3-S1 | 3-23*04 | 6*01 | | 4-1*01 | 2*01 | |
| h16B3-S2 | 3-23*04 | 6*01 | K94R | 4-1*01 | 2*01 | |
| h16B3-S3 | 3-23*04 | 6*01 | K94R, R98K, Y100BF | 4-1*01 | 2*01 | |
| h16B3-S4 | 3-23*04 | 6*01 | K94R, R98K, Y100BF | 4-1*01 | 2*01 | K93R |
| h16B3-S5 | 3-23*04 | 6*01 | K94R, R98K, H100R, Y100BF, V102L | 4-1*01 | 2*01 | |
| h16B3-S6 | 3-23*04 | 6*01 | K94R, R98K, H100R, Y100BF, V102L | 4-1*01 | 2*01 | K93R |

TABLE 7-continued

| | Heavy chain | | | Light chain | | |
|---|---|---|---|---|---|---|
| mAb | VH | JH | Mutation | VK | JK | Mutation |
| h16B3-S7 | 3-23*04 | 6*01 | G31A, E50D, K94R, R98K, H100R, Y100BF, V102L | 4-1*01 | 2*01 | |
| h16B3-S8 | 3-23*04 | 6*01 | G31A, E50D, K94R, R98K, H100R, Y100BF, V102L | 4-1*01 | 2*01 | K93R |
| h16B3-F1 | 3-23*04 | 6*01 | K94R | 1-39*01 | 2*01 | |
| h16B3-F2 | 3-23*04 | 6*01 | K94R | 3-15*01 | 2*01 | |
| h16B3-F3 | 3-23*04 | 6*01 | K94R | 3-20*01 | 2*01 | |
| h55A1-S1 | 7-4-1*01 | 6*03 | | 7-3*01 | 4*02 | |
| h55A1-S2 | 7-4-1*01 | 6*03 | M34L, Y100BF | 7-3*01 | 4*02 | |
| h55A1-S3 | 7-4-1*01 | 6*03 | M34L, Y100BF | 7-3*01 | 4*02 | Q90N |
| h55A1-S4 | 7-4-1*01 | 6*03 | G33A, P57G, Y97F, Y100BF | 7-3*01 | 4*02 | |
| h55A1-S5 | 7-4-1*01 | 6*03 | G33A, P57G, Y97F, Y100BF | 7-3*01 | 4*02 | Q90N |
| h55A1-S6 | 7-4-1*01 | 6*03 | G33A, M34L, P57G, D62E, Y97F, Y100BF | 7-3*01 | 4*02 | |
| h55A1-S7 | 7-4-1*01 | 6*03 | G33A, M34L, P57G, D62E, Y97F, Y100BF | 7-3*01 | 4*02 | Q90N |
| h55A1-F1 | 7-4-1*01 | 6*03 | | 1-33*01 | 4*02 | |
| h55A1-F2 | 1-18*01 | 6*03 | | 3-15*01 | 4*02 | |
| h55A1-F3 | 1-18*01 | 6*03 | | 1-39*01 | 4*02 | |
| h55A1-F4 | 1-18*01 | 6*03 | | 3-20*01 | 4*02 | |
| h55A1-F5 | 1-46*01 | 6*03 | | 1-39*01 | 4*02 | |
| h55A1-F6 | 1-46*01 | 6*03 | | 3-15*01 | 4*02 | |
| h53A11-S1 | 1-3*01 | 6*02 | R94K | 3-15*01 | 2*01 | P8L, Y49K |
| h53A11-S2 | 1-3*01 | 6*02 | R94K | 3-15*01 | 2*01 | P8L |
| h53A11-S3 | 1-3*01 | 6*02 | R94K | 3-15*01 | 2*01 | Y49K |
| h53A11-S4 | 1-3*01 | 6*02 | | 3-15*01 | 2*01 | Y49K |
| h23H8-S1 | 1-2*02 | 6*02 | | 1-39*01 | 2*01 | |
| h23H8-S2 | 1-2*02 | 6*02 | | 1-39*01 | 2*01 | Y49S, P80R |
| h23H8-S3 | 1-2*02 | 6*02 | | 1-39*01 | 2*01 | Y49S |
| h13B3-S1 | 1-46*03 | 6*01 | | 3-20*01 | 4*01 | |
| h13B3-S2 | 1-2*01 | 6*01 | | 3-20*01 | 4*01 | |
| h13B3-S3 | 1-46*03 | 6*01 | | 3-11*01 | 4*01 | |
| h13B3-S4 | 1-2*01 | 6*01 | | 3-11*01 | 4*01 | |
| h12B10-S1 | 3-33*01 | 5*01 | S95D, Y96H, D97L, G98A, S99Y, P100Y, P101D, S102V | 1-33*01 | 2*04 | |
| h12B10-S2 | 3-33*01 | 5*01 | S95D, Y96H, D97L, G98A, S99F, P100Y, P101D, S102L | 1-33*01 | 2*04 | |
| h12B10-S3 | 3-33*01 | 5*01 | S95D, Y96H, D97L, G98A, S99F, P100F, P101D, S102L | 1-33*01 | 2*04 | |
| h12B10-S4 | 3-33*01 | 5*01 | T31S, S95D, Y96H, D97L, G98V, S99F, P100F, P101D, S102L | 1-33*01 | 2*04 | |
| h16F6-S1 | 1-46*01 | 6*01 | R94V | 1-39*01 | 4*01 | A43S |
| h16F6-S2 | 1-46*01 | 6*01 | R94V | 1-39*01 | 4*01 | A43S, S67A |
| h16F6-S3 | 1-46*01 | 6*01 | R94V | 1-39*01 | 4*01 | A43S, S63T, S67A |
| h16F6-S4 | 1-46*01 | 6*01 | R94V | 1-39*01 | 4*01 | A43S, S63T, S67A, L73F |
| h16F6-5S | 1-46*01 | 6*01 | R94V | 1-39*01 | 4*01 | T20S, A43S, S63T, S67A, L73F |

Example 2

Measurement of Inhibitory Activity of Anti-EL Humanized Antibody

Humanized antibodies were produced from the plasmid vector as described in Example 1. The inhibitory activity of protein A column purified anti-EL humanized antibodies against human EL, human [1-305]-mouse chimeric EL, human [331-459]-mouse chimeric EL, cynomolgus monkey EL or mouse EL were measured as follows. Anti-EL humanized antibody solution, assay buffer (20 mM Tris/HCl (pH 7.5), 0.5% BSA, 4 mM CaCl$_2$, 150 mM NaCl) and 2 mg/mL human HDL (Athens Research & Technology) were mixed in a microtiter plate, followed by adding EL heparin extract. After incubation at 37° C. for 90 min, non-esterified Fatty Acid (NEFA) released from HDL was determined using a commercially available kit (NEFA C test-Wako, Wako). The NEFA amount was used as enzyme activity index. Enzyme activity in the case of adding no anti-EL humanized antibody was determined as control value and specific activity was calculated against the control value at each concentration of the anti-EL humanized antibody. The concentration of anti-EL humanized antibody where 50% of EL activity was inhibited was calculated from the inhibition curve as IC50 value. The result was summarized in Table 8 to 11.

Mouse 16B3 derived humanized antibodies h16B3-S1, h16B3-S2, h16B3-S3, h16B3-S4, h16B3-S5, h16B3-S6, h16B3-S7, h16B3-S8, h16B3-F1, h16B3-F2 and h16B3-F3 showed about the same or increased neutralization activity. From the result, K or R at position 94 of heavy chain, G or A at position 31 of heavy chain, E or D at position 50 of heavy chain, R or K at position 98 of heavy chain, H or R at position 100 of heavy chain, Y or F at position 100B of heavy chain, V or L at position 102 of heavy chain and K or R at position 93 of light chain are considered to be acceptable. Additionally, human germline sequences IGKV4-1*01, IGKV1-39*01, IGKV3-15*01 or IGKV3-20*01 are considered to be used acceptors for mouse CDRs of light chain.

Mouse 55A1 derived humanized antibodies h55A1-S1, h55A1-S2, h55A1-S3, h55A1-S4, h55A1-S5, h55A1-S6, h55A1-S7, h55A1-F1, h55A1-F2, h55A1-F3, h55A1-F4, h55A1-F5 and h55A1-F6 showed about the same or increased neutralization activity. From the result, G or A at position 33 of heavy chain, M or L at position 34 of heavy chain, P or G at position 57 of heavy chain, D or E at position 62 of heavy chain, Y or F at position 97 of heavy chain, Y or F at position 100B of heavy chain and Q or N at position 90 of light chain are considered to be acceptable. Additionally, human germline sequences IGHV7-4-1*02, IGHV1-18*01 or IGHV1-46*01 are considered to be used acceptors for CDRs of heavy chain, and IGKV7-3*01, IGKV1-33*01, IGKV1-39*01, IGKV3-15*01 or IGKV3-20*01 are considered to be used acceptors for CDRs of light chain.

Mouse 53A11 derived humanized antibodies h53A11-S1, h53A11-S2 and h53A11-S3 showed about the same or increased neutralization activity although h53A11-S4 showed decreased neutralization activity. From the result, combination of R94K mutation of heavy chain and P8L mutation of light chain, or combination of R94K mutation of heavy chain and Y49K mutation of light chain are considered to be desirable.

Mouse 23H8 derived humanized antibodies h23H8-S2 and h23H8-S3 showed about the same or increased neutralization activity although h23H8-S1 showed decreased neutralization activity. From the result, combination of Y49S and P80R mutations of light chain are considered to be desirable.

Mouse 13B3 derived humanized antibodies h13B3-S1, h13B3-S2, h13B3-S3 and h13B3-S4 showed about the same or increased neutralization activity.

Mouse 12B10 derived humanized antibodies h12B10-S1, h12B10-S2, h12B10-S3 and h12B10-S4 showed about the same or increased neutralization activity.

Mouse 16F6 derived humanized antibodies h16F6-S1, h16F6-S2, h16F6-S3, h16F6-S4, h16F6-S5 and h16F6-S5 showed about the same or increased neutralization activity. From the result, combination of R94V mutation of heavy chain and A43S mutation of light chain are considered to be desirable. Additionally, T or S at position 20 of light chain, S or T at position 63 of light chain, S or A at position 67 of light chain, L of F at position 73 of light chain are considered to be acceptable.

TABLE 8

| mAb | Neutralizing activity IC50 [nM] Human EL |
|---|---|
| h16B3-S2 | 4.6 |
| h55A1-S1 | 3.9 |
| h53A11-S1 | 9.7 |
| h23H8-S2 | 4.5 |
| h13B3-S1 | 2.3 |

TABLE 9

| mAb | Neutralizing activity IC50 [nM] Chimeric EL |
|---|---|
| 16B3 (mouse mAb) | 1.3 |
| h16B3-S1 | 2.7 |
| h16B3-S2 | 5.3 |
| h16B3-S3 | 1.9 |
| h16B3-S4 | 1.7 |
| h16B3-S5 | 1.2 |
| h16B3-S6 | 1.0 |
| h16B3-S7 | 1.4 |
| h16B3-S8 | 1.4 |
| h16B3-F1 | 2.3 |
| h16B3-F2 | 2.4 |
| h16B3-F3 | 2.0 |
| 55A1 (mouse mAb) | 1.1 |
| h55A1-S1 | 2.2 |
| h55A1-S2 | 1.1 |
| h55A1-S3 | 1.2 |
| h55A1-S4 | 1.1 |
| h55A1-S5 | 1.3 |
| h55A1-S6 | 1.2 |
| h55A1-S7 | 1.0 |
| h55A1-F1 | 1.9 |
| h55A1-F2 | 2.1 |
| h55A1-F3 | 1.1 |
| h55A1-F4 | 2.4 |
| h55A1-F5 | 1.3 |
| h55A1-F6 | 2.3 |
| 53A11 (mouse mAb) | 2.6 |
| h53A11-S1 | 2.1 |
| h53A11-S2 | 2.7 |
| h53A11-S3 | 1.8 |
| 23H8 (mouse mAb) | 1.7 |
| h23H8-S2 | 1.7 |
| h23H8-S3 | 2.0 |
| 13B3 (mouse mAb) | 4.1 |
| h13B3-S1 | 3.0 |
| h13B3-S2 | 9.0 |
| h13B3-S3 | 2.1 |
| h13B3-S4 | 2.6 |
| 12B10 (mouse mAb) | 15 |
| h12B10-S1 | 6.0 |
| h12B10-S2 | 5.4 |
| h12B10-S3 | 4.9 |
| h12B10-S4 | 6.4 |

TABLE 10

| mAb | Neutralizing activity IC50 [nM] Cynomolgus monkey EL |
|---|---|
| 16B3 (mouse mAb) | 1.8 |
| h16B3-S1 | 3.6 |
| h16B3-S2 | 1.9 |
| 55A1 (mouse mAb) | 1.3 |
| h55A1-S1 | 1.6 |
| 53A11 (mouse mAb) | 2.7 |
| h53A11-S1 | 1.7 |
| h53A11-S2 | 1.8 |
| h53A11-S3 | 1.2 |
| h53A11-S4 | 12 |
| 23H8 (mouse mAb) | 1.4 |
| h23H8-S1 | 26 |

TABLE 10-continued

| mAb | Neutralizing activity IC50 [nM] Cynomolgus monkey EL |
|---|---|
| h23H8-S2 | 1.7 |
| h23H8-S3 | 1.8 |
| 13B3 (mouse mAb) | 3.1 |
| h13B3-S1 | 2.4 |
| h13B3-S2 | 3.6 |
| h13B3-S3 | 4.1 |
| h13B3-S4 | 2.9 |

TABLE 11

| | Neutralizing activity IC50 [nM] | |
|---|---|---|
| mAb | Baboon EL | Mouse |
| h16F6-S1 | 2.6 | 3.1 |
| h16F6-S2 | 3.3 | 3.0 |
| h16F6-S3 | 3.1 | 3.3 |
| h16F6-S4 | 2.6 | 2.0 |
| h16F6-S5 | 2.0 | 2.1 |

Example 3

Measurement of Inhibitory Activity of Anti-EL Humanized Antibody Against HL and LPL The DNA encoding human HL was cloned into pcDNA3.1 expression vector (Invitrogen). The expression vector was transfected into HEK293F cells and cultured at 37° C. 8% CO2 for 2 days. The cells were centrifuged and the cells were collected, the cells were suspended with PBS containing 20 U/mL of Heparin (SIGMA). The cell suspension was incubated at 37° C. for 45 min. The supernatant obtained by removing cells with centrifugation was used as human HL enzyme solution. Human LPL enzyme solution was prepared by using the same method. After adding anti-EL antibody to the solution containing 20 mM Tris-HCl Buffer (pH 7.5), 0.5% bovine serum albumin, 4 mM CaCl2, 150 mM NaCl and 0.5 mg/mL human VLDL (INTRACEL), human HL or human LPL enzyme was added (total volume 10 μl). After reaction at 37° C. for 2 hr, free fatty acid (NEFA) made from VLDL by HL or LPL enzyme was determined using NEFA C-test Wako (Wako), the NFFA amount was used as enzyme activity index. Enzyme activity in the case of adding no anti-EL antibody was determined as control value and the specific activity was calculated against the control value at each concentration of the antibody. The concentration of anti-EL humanized antibody where 50% of EL activity was inhibited was calculated from the inhibition curve as IC50 value. The result was shown in Table 12. As a result, it was shown that humanized antibodies h16B3-S2, h55A1-S1, h53A11-S1, h23H8-S2 and h13B3-S1 inhibited neither HL nor LPL enzyme activity.

TABLE 12

| | Neutralizing activity IC50 [nM] | |
|---|---|---|
| mAb | Human HL | Human LPL |
| h16B3-S2 | >400 | >400 |
| h55A1-S1 | >1800 | >1800 |
| h53A11-S1 | >400 | >400 |
| h23H8-S2 | >400 | >400 |
| h13B3-S1 | >400 | >400 |

Example 4

Binding Affinity of Anti-EL Humanized Antibody

The binding affinities of anti-EL antibodies were measured using Biacore. Anti-C2-tag antibody was immobilized on a sensor chip CM5 (GE HealthCare) using amine-coupling and human [1-305]-mouse chimeric EL, human [331-459]-mouse chimeric EL, cynomolgus monkey EL or mouse EL heparin extract was added and EL was captured on the sensor chip. Then, anti-EL humanized antibodies were added and the binding affinities were calculated by bivalent fitting of BIAevaluation software. The results were summarized in Table 13 to 15

TABLE 13

| | Affinity for human-mouse chimeric EL | | |
|---|---|---|---|
| mAb | ka (1/Ms) | kd (1/s) | KD (M) |
| h16B3-S2 | $2.4 \times 10^4$ | $2.2 \times 10^{-4}$ | $9.3 \times 10^{-9}$ |
| h16B3-S3 | $3.0 \times 10^4$ | $1.3 \times 10^{-4}$ | $4.5 \times 10^{-9}$ |
| h16B3-S4 | $6.1 \times 10^4$ | $1.8 \times 10^{-4}$ | $3.0 \times 10^{-9}$ |
| h16B3-S5 | $5.4 \times 10^4$ | $5.7 \times 10^{-5}$ | $1.0 \times 10^{-9}$ |
| h16B3-S6 | $6.0 \times 10^4$ | $5.8 \times 10^{-5}$ | $1.0 \times 10^{-9}$ |
| h16B3-S7 | $5.0 \times 10^4$ | $5.9 \times 10^{-5}$ | $1.2 \times 10^{-9}$ |
| h16B3-S8 | $5.2 \times 10^4$ | $4.0 \times 10^{-5}$ | $7.8 \times 10^{-10}$ |
| h16B3-F1 | $3.8 \times 10^4$ | $2.0 \times 10^{-4}$ | $5.2 \times 10^{-9}$ |
| h16B3-F2 | $2.9 \times 10^4$ | $1.1 \times 10^{-4}$ | $3.8 \times 10^{-9}$ |
| h16B3-F3 | $1.9 \times 10^4$ | $2.0 \times 10^{-4}$ | $1.0 \times 10^{-8}$ |
| h55A1-S1 | $2.7 \times 10^4$ | $8.6 \times 10^{-4}$ | $3.1 \times 10^{-8}$ |
| h55A1-S2 | $3.5 \times 10^4$ | $3.7 \times 10^{-4}$ | $1.1 \times 10^{-8}$ |
| h55A1-S3 | $1.2 \times 10^5$ | $5.1 \times 10^{-4}$ | $4.2 \times 10^{-9}$ |
| h55A1-S4 | $8.0 \times 10^4$ | $2.4 \times 10^{-4}$ | $3.0 \times 10^{-9}$ |
| h55A1-S5 | $2.7 \times 10^4$ | $3.3 \times 10^{-4}$ | $1.2 \times 10^{-8}$ |
| h55A1-S6 | $4.7 \times 10^4$ | $6.3 \times 10^{-5}$ | $1.4 \times 10^{-9}$ |
| h55A1-S7 | $1.1 \times 10^5$ | $5.5 \times 10^{-4}$ | $5.1 \times 10^{-9}$ |
| h55A1-F1 | $2.0 \times 10^5$ | $1.7 \times 10^{-5}$ | $8.4 \times 10^{-11}$ |
| h55A1-F2 | $1.6 \times 10^5$ | $2.6 \times 10^{-5}$ | $1.7 \times 10^{-10}$ |
| h55A1-F3 | $1.1 \times 10^5$ | $3.3 \times 10^{-5}$ | $2.9 \times 10^{-10}$ |
| h55A1-F4 | $1.4 \times 10^5$ | $3.0 \times 10^{-5}$ | $2.2 \times 10^{-10}$ |
| h55A1-F5 | $1.4 \times 10^5$ | $1.6 \times 10^{-5}$ | $1.1 \times 10^{-10}$ |
| h55A1-F6 | $1.6 \times 10^5$ | $4.8 \times 10^{-6}$ | $3.0 \times 10^{-10}$ |
| h12B10-S1 | $1.9 \times 10^5$ | $3.5 \times 10^{-4}$ | $1.9 \times 10^{-9}$ |
| h12B10-S2 | $2.4 \times 10^5$ | $3.3 \times 10^{-5}$ | $1.4 \times 10^{-10}$ |
| h12B10-S3 | $1.5 \times 10^5$ | $1.7 \times 10^{-5}$ | $1.1 \times 10^{-10}$ |
| h12B10-S4 | $5.5 \times 10^5$ | $3.9 \times 10^{-5}$ | $7.2 \times 10^{-10}$ |

TABLE 14

| | Affinity for Cynomolgus monkey EL | | |
|---|---|---|---|
| mAb | ka (1/Ms) | kd (1/s) | KD (M) |
| h16B3-S1 | $9.4 \times 10^4$ | $1.0 \times 10^{-3}$ | $1.1 \times 10^{-8}$ |
| h16B3-S2 | $5.1 \times 10^4$ | $1.0 \times 10^{-4}$ | $2.0 \times 10^{-9}$ |
| h55A1-S1 | $4.4 \times 10^5$ | $2.6 \times 10^{-4}$ | $5.9 \times 10^{-10}$ |
| h53A11-S1 | $1.3 \times 10^5$ | $3.0 \times 10^{-4}$ | $2.3 \times 10^{-9}$ |
| h53A11-S2 | $1.5 \times 10^5$ | $6.5 \times 10^{-4}$ | $4.3 \times 10^{-9}$ |
| h53A11-S3 | $1.2 \times 10^5$ | $7.0 \times 10^{-4}$ | $5.8 \times 10^{-9}$ |
| h23H8-S1 | $1.0 \times 10^5$ | $3.6 \times 10^{-3}$ | $3.6 \times 10^{-8}$ |
| h23H8-S2 | $2.3 \times 10^5$ | $9.9 \times 10^{-4}$ | $4.3 \times 10^{-9}$ |
| h23H8-S3 | $3.7 \times 10^5$ | $1.5 \times 10^{-4}$ | $4.1 \times 10^{-10}$ |
| h13B3-S1 | $7.6 \times 10^4$ | $4.3 \times 10^{-4}$ | $5.7 \times 10^{-9}$ |
| h13B3-S2 | $4.5 \times 10^4$ | $1.4 \times 10^{-4}$ | $3.1 \times 10^{-9}$ |
| h13B3-S3 | $6.6 \times 10^4$ | $8.5 \times 10^{-4}$ | $1.3 \times 10^{-8}$ |
| h13B3-S4 | $1.1 \times 10^5$ | $3.8 \times 10^{-4}$ | $3.5 \times 10^{-9}$ |

TABLE 15

| | Affinity for Baboon EL | | | Affinity for Mouse EL | | |
|---|---|---|---|---|---|---|
| mAb | ka (1/Ms) | kd (1/s) | KD (M) | ka (1/Ms) | kd (1/s) | KD (M) |
| h16F6-S1 | $1.3 \times 10^{6}$ | $7.4 \times 10^{-4}$ | $5.7 \times 10^{-10}$ | $1.2 \times 10^{6}$ | $1.9 \times 10^{-4}$ | $1.6 \times 10^{-10}$ |

INDUSTRIAL APPLICABILITY

The humanized monoclonal antibody which inhibits the enzymatic activity of vascular endothelial lipase of the present invention is useful as a drug for prevention and/or treatment of dyslipidemia, hyperlipidemia, arteriosclerosis, atherosclerosis, hypercholesterolemia, hypertriglyceridemia, diabetes, obesity and/or syndrome X because it has selectively inhibitory activity against vascular endothelial lipase.

SEQUENCE LISTING

```
<160> NUMBER OF SEQ ID NOS: 130

<210> SEQ ID NO 1
<211> LENGTH: 500
<212> TYPE: PRT
<213> ORGANISM: Homo sapiens

<400> SEQUENCE: 1

Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
 50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
            100                 105                 110

Glu Lys Asp Ala Asn Val Val Val Val Asp Trp Leu Pro Leu Ala His
        115                 120                 125

Gln Leu Tyr Thr Asp Ala Val Asn Asn Thr Arg Val Val Gly His Ser
    130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Ala Asp Ile His Lys Arg Leu
        195                 200                 205

Ser Pro Asp Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
            260                 265                 270
```

-continued

```
Glu His Glu Arg Ala Val His Leu Phe Val Asp Ser Leu Val Asn Gln
            275                 280                 285

Asp Lys Pro Ser Phe Ala Phe Gln Cys Thr Asp Ser Asn Arg Phe Lys
        290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr Tyr Gln Met Lys
            340                 345                 350

Ile His Val Phe Ser Tyr Lys Asn Met Gly Glu Ile Glu Pro Thr Phe
            355                 360                 365

Tyr Val Thr Leu Tyr Gly Thr Asn Ala Asp Ser Gln Thr Leu Pro Leu
        370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
        435                 440                 445

Ile Arg Val Lys Ser Gly Glu Thr Gln Arg Lys Leu Thr Phe Cys Thr
            450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro
            500

<210> SEQ ID NO 2
<211> LENGTH: 5
<212> TYPE: PRT
<213> ORGANISM: Artificial sequence
<220> FEATURE:
<223> OTHER INFORMATION: CDR1 of h16B3-S1 heavy chain

<400> SEQUENCE: 2

Gly Tyr Thr Met Ser
1               5

<210> SEQ ID NO 3
<211> LENGTH: 17
<212> TYPE: PRT
<213> ORGANISM: Artificial sequence
<220> FEATURE:
<223> OTHER INFORMATION: CDR2 of h16B3-S1 heavy chain

<400> SEQUENCE: 3

Glu Ile Ser Phe Ala Arg Asp Arg Ala Phe Tyr Pro Asp Thr Val Lys
1               5                   10                  15

Gly

<210> SEQ ID NO 4
<211> LENGTH: 13
<212> TYPE: PRT
<213> ORGANISM: Artificial sequence
<220> FEATURE:
```

<223> OTHER INFORMATION: CDR3 of h16B3-S1 heavy chain

<400> SEQUENCE: 4

Leu Gly Gly Arg Asn His Asp Tyr Trp Tyr Phe Asp Val
1               5                   10

<210> SEQ ID NO 5
<211> LENGTH: 15
<212> TYPE: PRT
<213> ORGANISM: Artificial sequence
<220> FEATURE:
<223> OTHER INFORMATION: CDR1 of h16B3- S1 light chain

<400> SEQUENCE: 5

Arg Ala Ser Glu Ser Val Glu Tyr Tyr Gly Thr Ser Leu Met Gln
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: CDR2 of h16B3- S1 light chain

<400> SEQUENCE: 6

Ala Ala Ser Asn Val Glu Ser
1               5

<210> SEQ ID NO 7
<211> LENGTH: 9
<212> TYPE: PRT
<213> ORGANISM: Artificial sequence
<220> FEATURE:
<223> OTHER INFORMATION: CDR3 of h16B3- S1 light chain

<400> SEQUENCE: 7

Gln Gln Ser Trp Lys Val Pro Phe Thr
1               5

<210> SEQ ID NO 8
<211> LENGTH: 13
<212> TYPE: PRT
<213> ORGANISM: Artificial sequence
<220> FEATURE:
<223> OTHER INFORMATION: CDR3 of h16B3-S3 heavy chain

<400> SEQUENCE: 8

Leu Gly Gly Lys Asn His Asp Phe Trp Tyr Phe Asp Val
1               5                   10

<210> SEQ ID NO 9
<211> LENGTH: 9
<212> TYPE: PRT
<213> ORGANISM: Artificial Sequence
<220> FEATURE:
<223> OTHER INFORMATION: CDR3 of h16B3-S4 light chain

<400> SEQUENCE: 9

Gln Gln Ser Trp Arg Val Pro Phe Thr
1               5

<210> SEQ ID NO 10
<211> LENGTH: 13
<212> TYPE: PRT
<213> ORGANISM: Artificial sequence
<220> FEATURE:
<223> OTHER INFORMATION: CDR3 of h16B3-S5 heavy chain

```
<400> SEQUENCE: 10

Leu Gly Gly Lys Asn Arg Asp Phe Trp Tyr Phe Asp Leu
1               5                   10

<210> SEQ ID NO 11
<211> LENGTH: 5
<212> TYPE: PRT
<213> ORGANISM: Artificial sequence
<220> FEATURE:
<223> OTHER INFORMATION: CDR1 of h16B3-S7 heavy chain

<400> SEQUENCE: 11

Ala Tyr Thr Met Ser
1               5

<210> SEQ ID NO 12
<211> LENGTH: 17
<212> TYPE: PRT
<213> ORGANISM: Artificial sequence
<220> FEATURE:
<223> OTHER INFORMATION: CDR2 of h16B3-S7 heavy chain

<400> SEQUENCE: 12

Asp Ile Ser Phe Ala Arg Asp Arg Ala Phe Tyr Pro Asp Thr Val Lys
1               5                   10                  15
Gly

<210> SEQ ID NO 13
<211> LENGTH: 5
<212> TYPE: PRT
<213> ORGANISM: Artificial sequence
<220> FEATURE:
<223> OTHER INFORMATION: CDR1 of h55A1-S1 heavy chain

<400> SEQUENCE: 13

Asn Tyr Gly Met Asn
1               5

<210> SEQ ID NO 14
<211> LENGTH: 17
<212> TYPE: PRT
<213> ORGANISM: Artificial sequence
<220> FEATURE:
<223> OTHER INFORMATION: CDR2 of h55A1-S1 heavy chain

<400> SEQUENCE: 14

Trp Ile Asn Thr Tyr Ser Gly Val Pro Thr Tyr Ala Gly Asp Phe Lys
1               5                   10                  15
Gly

<210> SEQ ID NO 15
<211> LENGTH: 11
<212> TYPE: PRT
<213> ORGANISM: Artificial sequence
<220> FEATURE:
<223> OTHER INFORMATION: CDR3 of h55A1-S1 heavy chain

<400> SEQUENCE: 15

Arg Gly Tyr Tyr Gly Arg Arg Tyr Phe Asp Val
1               5                   10

<210> SEQ ID NO 16
<211> LENGTH: 15
<212> TYPE: PRT
```

<213> ORGANISM: Artificial sequence
<220> FEATURE:
<223> OTHER INFORMATION: CDR1 of h55A1-S1 light chain

<400> SEQUENCE: 16

Lys Ala Ser Gln Ser Val Asp Tyr Asp Val Asp Ser Tyr Met His
1               5                   10                  15

<210> SEQ ID NO 17
<211> LENGTH: 7
<212> TYPE: PRT
<213> ORGANISM: Artificial sequence
<220> FEATURE:
<223> OTHER INFORMATION: CDR2 of h55A1-S1 light chain

<400> SEQUENCE: 17

Ala Ala Ser Asn Leu Ala Ser
1               5

<210> SEQ ID NO 18
<211> LENGTH: 9
<212> TYPE: PRT
<213> ORGANISM: Artificial sequence
<220> FEATURE:
<223> OTHER INFORMATION: CDR3 of h55A1-S1 light chain

<400> SEQUENCE: 18

Gln Gln Thr Ile Glu Asp Pro Pro Thr
1               5

<210> SEQ ID NO 19
<211> LENGTH: 5
<212> TYPE: PRT
<213> ORGANISM: Artificial sequence
<220> FEATURE:
<223> OTHER INFORMATION: CDR1 of h55A1-S2 heavy chain

<400> SEQUENCE: 19

Asn Tyr Gly Leu Asn
1               5

<210> SEQ ID NO 20
<211> LENGTH: 11
<212> TYPE: PRT
<213> ORGANISM: Artificial sequence
<220> FEATURE:
<223> OTHER INFORMATION: CDR3 of h55A1-S2 heavy chain

<400> SEQUENCE: 20

Arg Gly Tyr Tyr Gly Arg Arg Phe Phe Asp Val
1               5                   10

<210> SEQ ID NO 21
<211> LENGTH: 9
<212> TYPE: PRT
<213> ORGANISM: Artificial sequence
<220> FEATURE:
<223> OTHER INFORMATION: CDR3 of h55A1-S3 light chain

<400> SEQUENCE: 21

Gln Asn Thr Ile Glu Asp Pro Pro Thr
1               5

<210> SEQ ID NO 22
<211> LENGTH: 5
<212> TYPE: PRT
<213> ORGANISM: Artificial sequence

```
<220> FEATURE:
<223> OTHER INFORMATION: CDR1 of h55A1-S4 heavy chain

<400> SEQUENCE: 22

Asn Tyr Ala Met Asn
1               5

<210> SEQ ID NO 23
<211> LENGTH: 17
<212> TYPE: PRT
<213> ORGANISM: Artificial sequence
<220> FEATURE:
<223> OTHER INFORMATION: CDR2 of h55A1-S4 heavy chain

<400> SEQUENCE: 23

Trp Ile Asn Thr Tyr Ser Gly Val Gly Thr Tyr Ala Gly Asp Phe Lys
1               5                   10                  15

Gly

<210> SEQ ID NO 24
<211> LENGTH: 11
<212> TYPE: PRT
<213> ORGANISM: Artificial sequence
<220> FEATURE:
<223> OTHER INFORMATION: CDR3 of h55A1-S4 and S6 heavy chain

<400> SEQUENCE: 24

Arg Gly Phe Tyr Gly Arg Arg Phe Phe Asp Val
1               5                   10

<210> SEQ ID NO 25
<211> LENGTH: 5
<212> TYPE: PRT
<213> ORGANISM: Artificial sequence
<220> FEATURE:
<223> OTHER INFORMATION: CDR1 of h55A1-S6 heavy chain

<400> SEQUENCE: 25

Asn Tyr Ala Leu Asn
1               5

<210> SEQ ID NO 26
<211> LENGTH: 5
<212> TYPE: PRT
<213> ORGANISM: Artificial sequence
<220> FEATURE:
<223> OTHER INFORMATION: CDR1 of h53A11-S1 heavy chain

<400> SEQUENCE: 26

Asp Tyr Thr Met His
1               5

<210> SEQ ID NO 27
<211> LENGTH: 17
<212> TYPE: PRT
<213> ORGANISM: Artificial sequence
<220> FEATURE:
<223> OTHER INFORMATION: CDR2 of h53A11-S1 heavy chain

<400> SEQUENCE: 27

Gly Ile Asn Pro Tyr Tyr Gly Gly Thr Thr Tyr Asn Glu Lys Phe Lys
1               5                   10                  15

Asp

<210> SEQ ID NO 28
```

```
<211> LENGTH: 10
<212> TYPE: PRT
<213> ORGANISM: Artificial sequence
<220> FEATURE:
<223> OTHER INFORMATION: CDR3 of h53A11-S1 heavy chain

<400> SEQUENCE: 28

Gly Asp Tyr Tyr Gly Gly Ser Tyr Asn Tyr
1               5                   10

<210> SEQ ID NO 29
<211> LENGTH: 11
<212> TYPE: PRT
<213> ORGANISM: Artificial sequence
<220> FEATURE:
<223> OTHER INFORMATION: CDR1 of h53A11-S1 light chain

<400> SEQUENCE: 29

Arg Ala Ser Gln Asp Ile Ser Asn Ser Leu His
1               5                   10

<210> SEQ ID NO 30
<211> LENGTH: 7
<212> TYPE: PRT
<213> ORGANISM: Artificial sequence
<220> FEATURE:
<223> OTHER INFORMATION: CDR2 of h53A11-S1 light chain

<400> SEQUENCE: 30

Tyr Ala Ser Gln Ser Ile Ser
1               5

<210> SEQ ID NO 31
<211> LENGTH: 9
<212> TYPE: PRT
<213> ORGANISM: Artificial sequence
<220> FEATURE:
<223> OTHER INFORMATION: CDR3 of h53A11-S1 light chain

<400> SEQUENCE: 31

Gln Gln Ser Asn Ser Trp Pro Tyr Thr
1               5

<210> SEQ ID NO 32
<211> LENGTH: 5
<212> TYPE: PRT
<213> ORGANISM: Artificial sequence
<220> FEATURE:
<223> OTHER INFORMATION: CDR1 of h23H8-S1 heavy chain

<400> SEQUENCE: 32

Asp Asn Thr Ile His
1               5

<210> SEQ ID NO 33
<211> LENGTH: 17
<212> TYPE: PRT
<213> ORGANISM: Artificial sequence
<220> FEATURE:
<223> OTHER INFORMATION: CDR2 of h23H8-S1 heavy chain

<400> SEQUENCE: 33

His Ile Asn Pro Tyr Tyr Gly Gly Thr Asn Asn Asn Glu Lys Phe Lys
1               5                   10                  15

Asp
```

```
<210> SEQ ID NO 34
<211> LENGTH: 11
<212> TYPE: PRT
<213> ORGANISM: Artificial sequence
<220> FEATURE:
<223> OTHER INFORMATION: CDR3 of h23H8-S1 heavy chain

<400> SEQUENCE: 34

Lys Gly Ile Tyr Tyr Ser Ser Pro Phe Asp Tyr
1               5                   10

<210> SEQ ID NO 35
<211> LENGTH: 11
<212> TYPE: PRT
<213> ORGANISM: Artificial sequence
<220> FEATURE:
<223> OTHER INFORMATION: CDR1 of h23H8-S1 light chain

<400> SEQUENCE: 35

Arg Ala Ser Gln Asp Ile Asn Asn Tyr Leu Asn
1               5                   10

<210> SEQ ID NO 36
<211> LENGTH: 7
<212> TYPE: PRT
<213> ORGANISM: Artificial sequence
<220> FEATURE:
<223> OTHER INFORMATION: CDR2 of h23H8-S1 light chain

<400> SEQUENCE: 36

Tyr Thr Ser Lys Leu His Ser
1               5

<210> SEQ ID NO 37
<211> LENGTH: 9
<212> TYPE: PRT
<213> ORGANISM: Artificial sequence
<220> FEATURE:
<223> OTHER INFORMATION: CDR3 of h23H8-S1 light chain

<400> SEQUENCE: 37

Gln Gln Gly Asn Thr Leu Pro Phe Thr
1               5

<210> SEQ ID NO 38
<211> LENGTH: 5
<212> TYPE: PRT
<213> ORGANISM: Artificial sequence
<220> FEATURE:
<223> OTHER INFORMATION: CDR1 of h13B3-S1 heavy chain

<400> SEQUENCE: 38

Glu Tyr Thr Met His
1               5

<210> SEQ ID NO 39
<211> LENGTH: 17
<212> TYPE: PRT
<213> ORGANISM: Artificial sequence
<220> FEATURE:
<223> OTHER INFORMATION: CDR2 of h13B3-S1 heavy chain

<400> SEQUENCE: 39

Ser Ile Asn Pro Tyr Tyr Gly Gly Thr Ser Tyr Asn Glu Lys Phe Lys
1               5                   10                  15

Asp
```

<210> SEQ ID NO 40
<211> LENGTH: 10
<212> TYPE: PRT
<213> ORGANISM: Artificial sequence
<220> FEATURE:
<223> OTHER INFORMATION: CDR3 of h13B3-S1 heavy chain

<400> SEQUENCE: 40

Tyr Gly Asn Tyr Val Gly Tyr Phe Asp Tyr
1               5                   10

<210> SEQ ID NO 41
<211> LENGTH: 10
<212> TYPE: PRT
<213> ORGANISM: Artificial sequence
<220> FEATURE:
<223> OTHER INFORMATION: CDR1 of h13B3-S1 light chain

<400> SEQUENCE: 41

Arg Ala Ser Ser Ser Val His Tyr Met Tyr
1               5                   10

<210> SEQ ID NO 42
<211> LENGTH: 7
<212> TYPE: PRT
<213> ORGANISM: Artificial sequence
<220> FEATURE:
<223> OTHER INFORMATION: CDR2 of h13B3-S1 light chain

<400> SEQUENCE: 42

Tyr Thr Ser Asn Leu Ala Pro
1               5

<210> SEQ ID NO 43
<211> LENGTH: 9
<212> TYPE: PRT
<213> ORGANISM: Artificial sequence
<220> FEATURE:
<223> OTHER INFORMATION: CDR3 of h13B3-S1 light chain

<400> SEQUENCE: 43

Gln Gln Phe Thr Ser Ser Pro Tyr Thr
1               5

<210> SEQ ID NO 44
<211> LENGTH: 7
<212> TYPE: PRT
<213> ORGANISM: Artificial sequence
<220> FEATURE:
<223> OTHER INFORMATION: CDR1 of h12B10-S1 heavy chain

<400> SEQUENCE: 44

Thr Ser Gly Met Gly Val Gly
1               5

<210> SEQ ID NO 45
<211> LENGTH: 16
<212> TYPE: PRT
<213> ORGANISM: Artificial sequence
<220> FEATURE:
<223> OTHER INFORMATION: CDR2 of h12B10-S1 heavy chain

<400> SEQUENCE: 45

His Ile Trp Trp Asn Asp Glu Lys Tyr Tyr Asn Pro Ser Leu Lys Ser
1               5                   10                  15

```
<210> SEQ ID NO 46
<211> LENGTH: 9
<212> TYPE: PRT
<213> ORGANISM: Artificial sequence
<220> FEATURE:
<223> OTHER INFORMATION: CDR3 of h12B10-S1 heavy chain

<400> SEQUENCE: 46

Asp His Leu Ala Tyr Tyr Phe Asp Val
1               5

<210> SEQ ID NO 47
<211> LENGTH: 11
<212> TYPE: PRT
<213> ORGANISM: Artificial sequence
<220> FEATURE:
<223> OTHER INFORMATION: CDR1 of h12B10-S1 light chain

<400> SEQUENCE: 47

Lys Ala Ser Gln Asp Ile Asn Lys Tyr Ile Ala
1               5                   10

<210> SEQ ID NO 48
<211> LENGTH: 7
<212> TYPE: PRT
<213> ORGANISM: Artificial sequence
<220> FEATURE:
<223> OTHER INFORMATION: CDR2 of h12B10-S1 light chain

<400> SEQUENCE: 48

Tyr Pro Phe Thr Leu Gln Pro
1               5

<210> SEQ ID NO 49
<211> LENGTH: 9
<212> TYPE: PRT
<213> ORGANISM: Artificial sequence
<220> FEATURE:
<223> OTHER INFORMATION: CDR3 of h12B10-S1 light chain

<400> SEQUENCE: 49

Leu Gln Tyr Asp Asn Leu Leu Trp Thr
1               5

<210> SEQ ID NO 50
<211> LENGTH: 9
<212> TYPE: PRT
<213> ORGANISM: Artificial sequence
<220> FEATURE:
<223> OTHER INFORMATION: CDR3 of h12B10-S2 heavy chain

<400> SEQUENCE: 50

Asp His Leu Ala Phe Tyr Phe Asp Leu
1               5

<210> SEQ ID NO 51
<211> LENGTH: 9
<212> TYPE: PRT
<213> ORGANISM: Artificial sequence
<220> FEATURE:
<223> OTHER INFORMATION: CDR3 of h12B10-S3 heavy chain

<400> SEQUENCE: 51

Asp His Leu Ala Phe Phe Phe Asp Leu
1               5

<210> SEQ ID NO 52
```

```
<211> LENGTH: 7
<212> TYPE: PRT
<213> ORGANISM: Artificial sequence
<220> FEATURE:
<223> OTHER INFORMATION: CDR1 of h12B10-S4 heavy chain

<400> SEQUENCE: 52

Ser Ser Gly Met Gly Val Gly
1               5

<210> SEQ ID NO 53
<211> LENGTH: 9
<212> TYPE: PRT
<213> ORGANISM: Artificial sequence
<220> FEATURE:
<223> OTHER INFORMATION: CDR3 of h12B10-S4 heavy chain

<400> SEQUENCE: 53

Asp His Leu Val Phe Phe Phe Asp Leu
1               5

<210> SEQ ID NO 54
<211> LENGTH: 5
<212> TYPE: PRT
<213> ORGANISM: Artificial sequence
<220> FEATURE:
<223> OTHER INFORMATION: CDR1 of h16F6-S1 heavy chain

<400> SEQUENCE: 54

Thr Tyr Trp Ile Ala
1               5

<210> SEQ ID NO 55
<211> LENGTH: 17
<212> TYPE: PRT
<213> ORGANISM: Artificial sequence
<220> FEATURE:
<223> OTHER INFORMATION: CDR2 of h16F6-S1 heavy chain

<400> SEQUENCE: 55

Glu Ile Leu Pro Gly Ser Ala Lys Thr Lys Tyr Asn Lys Lys Phe Lys
1               5                   10                  15

Gly

<210> SEQ ID NO 56
<211> LENGTH: 7
<212> TYPE: PRT
<213> ORGANISM: Artificial sequence
<220> FEATURE:
<223> OTHER INFORMATION: CDR3 of h16F6-S1 heavy chain

<400> SEQUENCE: 56

Tyr Asp Tyr Gly Ala Asp Tyr
1               5

<210> SEQ ID NO 57
<211> LENGTH: 11
<212> TYPE: PRT
<213> ORGANISM: Artificial sequence
<220> FEATURE:
<223> OTHER INFORMATION: CDR1 of h16F6-S1 light chain

<400> SEQUENCE: 57

Lys Ala Ser Gln Asp Val Tyr Thr Ala Val Ala
1               5                   10
```

```
<210> SEQ ID NO 58
<211> LENGTH: 7
<212> TYPE: PRT
<213> ORGANISM: Artificial sequence
<220> FEATURE:
<223> OTHER INFORMATION: CDR2 of h16F6-S1 light chain

<400> SEQUENCE: 58

Ser Ala Ser Tyr Arg Phe Thr
1               5

<210> SEQ ID NO 59
<211> LENGTH: 9
<212> TYPE: PRT
<213> ORGANISM: Artificial sequence
<220> FEATURE:
<223> OTHER INFORMATION: CDR3 of h16F6-S1 light chain

<400> SEQUENCE: 59

Gln Gln His Tyr Ser Ile Pro Arg Thr
1               5

<210> SEQ ID NO 60
<211> LENGTH: 122
<212> TYPE: PRT
<213> ORGANISM: Artificial sequence
<220> FEATURE:
<223> OTHER INFORMATION: Heavy chain of h16B3-S1

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Thr Met Ser Trp Val Arg Gln Ala Pro Gly Lys Gly Leu Glu Trp Val
            35                  40                  45

Ser Glu Ile Ser Phe Ala Arg Asp Arg Ala Phe Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Gly Arg Asn His Asp Tyr Trp Tyr Phe Asp Val Trp
            100                 105                 110

Gly Gln Gly Thr Thr Val Thr Val Ser Ser
        115                 120

<210> SEQ ID NO 61
<211> LENGTH: 111
<212> TYPE: PRT
<213> ORGANISM: Artificial sequence
<220> FEATURE:
<223> OTHER INFORMATION: Light chain of h16B3-S1,S2 and S3

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Ala Ala Ser Asn Val Glu Ser Gly Val Pro Asp
```

```
                    50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Trp
                 85                  90                  95

Lys Val Pro Phe Thr Phe Gly Gln Gly Thr Lys Leu Glu Ile Lys
                100                 105                 110
```

<210> SEQ ID NO 62
<211> LENGTH: 122
<212> TYPE: PRT
<213> ORGANISM: Artificial sequence
<220> FEATURE:
<223> OTHER INFORMATION: Heavy chain of h16B3-S2

<400> SEQUENCE: 62

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
                 20                  25                  30

Thr Met Ser Trp Val Arg Gln Ala Pro Gly Lys Gly Leu Glu Trp Val
             35                  40                  45

Ser Glu Ile Ser Phe Ala Arg Asp Arg Ala Phe Tyr Pro Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Arg Asn His Asp Tyr Trp Tyr Phe Asp Val Trp
                100                 105                 110

Gly Gln Gly Thr Thr Val Thr Val Ser Ser
            115                 120
```

<210> SEQ ID NO 63
<211> LENGTH: 122
<212> TYPE: PRT
<213> ORGANISM: Artificial sequence
<220> FEATURE:
<223> OTHER INFORMATION: Heavy chain of h16B3-S3

<400> SEQUENCE: 63

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
                 20                  25                  30

Thr Met Ser Trp Val Arg Gln Ala Pro Gly Lys Gly Leu Glu Trp Val
             35                  40                  45

Ser Glu Ile Ser Phe Ala Arg Asp Arg Ala Phe Tyr Pro Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Lys Asn His Asp Phe Trp Tyr Phe Asp Val Trp
                100                 105                 110

Gly Gln Gly Thr Thr Val Thr Val Ser Ser
            115                 120
```

<210> SEQ ID NO 64
<211> LENGTH: 111
<212> TYPE: PRT
<213> ORGANISM: Artificial sequence
<220> FEATURE:
<223> OTHER INFORMATION: Light chain of h16B3-S4

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Trp
                85                  90                  95

Arg Val Pro Phe Thr Phe Gly Gly Gly Thr Lys Leu Glu Ile Lys
            100                 105                 110

<210> SEQ ID NO 65
<211> LENGTH: 122
<212> TYPE: PRT
<213> ORGANISM: Artificial sequence
<220> FEATURE:
<223> OTHER INFORMATION: Heavy chain of h16B3-S5

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Thr Met Ser Trp Val Arg Gln Ala Pro Gly Lys Gly Leu Glu Trp Val
        35                  40                  45

Ser Glu Ile Ser Phe Ala Arg Asp Arg Ala Phe Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Lys Asn Arg Asp Phe Trp Tyr Phe Asp Leu Trp
            100                 105                 110

Gly Gln Gly Thr Thr Val Thr Val Ser Ser
        115                 120

<210> SEQ ID NO 66
<211> LENGTH: 122
<212> TYPE: PRT
<213> ORGANISM: Artificial sequence
<220> FEATURE:
<223> OTHER INFORMATION: Heavy chain of h16B3-S7

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr

```
                  20                  25                  30
Thr Met Ser Trp Val Arg Gln Ala Pro Gly Lys Gly Leu Glu Trp Val
                 35                  40                  45

Ser Asp Ile Ser Phe Ala Arg Asp Arg Ala Phe Tyr Pro Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Lys Asn Arg Asp Phe Trp Tyr Phe Asp Leu Trp
                100                 105                 110

Gly Gln Gly Thr Thr Val Thr Val Ser Ser
                115                 120

<210> SEQ ID NO 67
<211> LENGTH: 111
<212> TYPE: PRT
<213> ORGANISM: Artificial sequence
<220> FEATURE:
<223> OTHER INFORMATION: Light chain of h16B3-F1

<400> SEQUENCE: 67

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Glu Tyr Tyr
                 20                  25                  30

Gly Thr Ser Leu Met Gln Trp Tyr Gln Gln Lys Pro Gly Lys Ala Pro
                 35                  40                  45

Lys Leu Leu Ile Tyr Ala Ala Ser Asn Val Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Trp
                 85                  90                  95

Lys Val Pro Phe Thr Phe Gly Gln Gly Thr Lys Leu Glu Ile Lys
                100                 105                 110

<210> SEQ ID NO 68
<211> LENGTH: 111
<212> TYPE: PRT
<213> ORGANISM: Artificial sequence
<220> FEATURE:
<223> OTHER INFORMATION: Light chain of h16B3-F2

<400> SEQUENCE: 68

Glu Ile Val Met Thr Gln Ser Pro Ala Thr Leu Ser Val Ser Pro Gly
 1               5                  10                  15

Glu Arg Ala Thr Leu Ser Cys Arg Ala Ser Glu Ser Val Glu Tyr Tyr
                 20                  25                  30

Gly Thr Ser Leu Met Gln Trp Tyr Gln Gln Lys Pro Gly Gln Ala Pro
                 35                  40                  45

Arg Leu Leu Ile Tyr Ala Ala Ser Asn Val Glu Ser Gly Ile Pro Ala
 50                  55                  60

Arg Phe Ser Gly Ser Gly Ser Gly Thr Glu Phe Thr Leu Thr Ile Ser
 65                  70                  75                  80

Ser Leu Gln Ser Glu Asp Phe Ala Val Tyr Tyr Cys Gln Gln Ser Trp
                 85                  90                  95
```

```
Lys Val Pro Phe Thr Phe Gly Gln Gly Thr Lys Leu Glu Ile Lys
            100                 105                 110
```

<210> SEQ ID NO 69
<211> LENGTH: 111
<212> TYPE: PRT
<213> ORGANISM: Artificial sequence
<220> FEATURE:
<223> OTHER INFORMATION: Light chain of h16B3-F3

<400> SEQUENCE: 69

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Trp
                85                  90                  95

Lys Val Pro Phe Thr Phe Gly Gln Gly Thr Lys Leu Glu Ile Lys
            100                 105                 110
```

<210> SEQ ID NO 70
<211> LENGTH: 120
<212> TYPE: PRT
<213> ORGANISM: Artificial sequence
<220> FEATURE:
<223> OTHER INFORMATION: Heavy chain of h55A1-S1

<400> SEQUENCE: 70

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Val Pro Thr Tyr Ala Gly Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Tyr Tyr Gly Arg Tyr Phe Asp Val Trp Gly Lys
            100                 105                 110

Gly Thr Thr Val Thr Val Ser Ser
        115                 120
```

<210> SEQ ID NO 71
<211> LENGTH: 111
<212> TYPE: PRT
<213> ORGANISM: Artificial sequence
<220> FEATURE:
<223> OTHER INFORMATION: Light chain of h55A1-S1

<400> SEQUENCE: 71

```
Asp Ile Val Leu Thr Gln Ser Pro Ala Ser Leu Ala Val Ser Pro Gly
```

Gln Arg Ala Thr Ile Thr Cys Lys Ala Ser Gln Ser Val Asp Tyr Asp
                20                  25                  30

Val Asp Ser Tyr Met His Trp Tyr Gln Gln Lys Pro Gly Gln Pro Pro
            35                  40                  45

Lys Leu Leu Ile Tyr Ala Ala Ser Asn Leu Ala Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Thr Ile
                85                  90                  95

Glu Asp Pro Pro Thr Phe Gly Gly Gly Thr Lys Val Glu Ile Lys
                100                 105                 110

<210> SEQ ID NO 72
<211> LENGTH: 120
<212> TYPE: PRT
<213> ORGANISM: Artificial sequence
<220> FEATURE:
<223> OTHER INFORMATION: Heavy chain of h55A1-S2

<400> SEQUENCE: 72

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Asn Trp Val Arg Gln Ala Pro Gly Gln Gly Leu Glu Trp Met
            35                  40                  45

Gly Trp Ile Asn Thr Tyr Ser Gly Val Pro Thr Tyr Ala Gly Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Tyr Tyr Gly Arg Arg Phe Phe Asp Val Trp Gly Lys
                100                 105                 110

Gly Thr Thr Val Thr Val Ser Ser
            115                 120

<210> SEQ ID NO 73
<211> LENGTH: 111
<212> TYPE: PRT
<213> ORGANISM: Artificial sequence
<220> FEATURE:
<223> OTHER INFORMATION: Light chain of h55A1-S3

<400> SEQUENCE: 73

Asp Ile Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Asp Tyr Asp
                20                  25                  30

Val Asp Ser Tyr Met His Trp Tyr Gln Gln Lys Pro Gly Gln Pro Pro
            35                  40                  45

Lys Leu Leu Ile Tyr Ala Ala Ser Asn Leu Ala Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Asn Thr Ile
            85                  90                  95

Glu Asp Pro Pro Thr Phe Gly Gly Gly Thr Lys Val Glu Ile Lys
            100                 105                 110

<210> SEQ ID NO 74
<211> LENGTH: 120
<212> TYPE: PRT
<213> ORGANISM: Artificial sequence
<220> FEATURE:
<223> OTHER INFORMATION: Heavy chain of h55A1-S4

<400> SEQUENCE: 74

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met Asn Trp Val Arg Gln Ala Pro Gly Gln Gly Leu Glu Trp Met
        35                  40                  45

Gly Trp Ile Asn Thr Tyr Ser Gly Val Gly Thr Tyr Ala Gly Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Phe Tyr Gly Arg Arg Phe Phe Asp Val Trp Gly Lys
            100                 105                 110

Gly Thr Thr Val Thr Val Ser Ser
            115                 120

<210> SEQ ID NO 75
<211> LENGTH: 120
<212> TYPE: PRT
<213> ORGANISM: Artificial sequence
<220> FEATURE:
<223> OTHER INFORMATION: Heavy chain of h55A1-S6

<400> SEQUENCE: 75

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Leu Asn Trp Val Arg Gln Ala Pro Gly Gln Gly Leu Glu Trp Met
        35                  40                  45

Gly Trp Ile Asn Thr Tyr Ser Gly Val Gly Thr Tyr Ala Gly Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Phe Tyr Gly Arg Arg Phe Phe Asp Val Trp Gly Lys
            100                 105                 110

Gly Thr Thr Val Thr Val Ser Ser
            115                 120

<210> SEQ ID NO 76
<211> LENGTH: 111
<212> TYPE: PRT
<213> ORGANISM: Artificial sequence
<220> FEATURE:
<223> OTHER INFORMATION: Light chain of h55A1-F1

<400> SEQUENCE: 76

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Val Asp Ser Tyr Met His Trp Tyr Gln Gln Lys Pro Gly Lys Ala Pro
        35                  40                  45

Lys Leu Leu Ile Tyr Ala Ala Ser Asn Leu Ala Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Thr Ile
                85                  90                  95

Glu Asp Pro Pro Thr Phe Gly Gly Gly Thr Lys Val Glu Ile Lys
            100                 105                 110

<210> SEQ ID NO 77
<211> LENGTH: 120
<212> TYPE: PRT
<213> ORGANISM: Artificial sequence
<220> FEATURE:
<223> OTHER INFORMATION: Heavy chain of h55A1-F2

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Val Pro Thr Tyr Ala Gly Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gly Tyr Tyr Gly Arg Arg Tyr Phe Asp Val Trp Gly Lys
            100                 105                 110

Gly Thr Thr Val Thr Val Ser Ser
        115                 120

<210> SEQ ID NO 78
<211> LENGTH: 111
<212> TYPE: PRT
<213> ORGANISM: Artificial sequence
<220> FEATURE:
<223> OTHER INFORMATION: Light chain of h55A1-F2

<400> SEQUENCE: 78

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Tyr Asp
            20                  25                  30

Val Asp Ser Tyr Met His Trp Tyr Gln Gln Lys Pro Gly Gln Ala Pro
        35                  40                  45

```
Arg Leu Leu Ile Tyr Ala Ala Ser Asn Leu Ala Ser Gly Ile Pro Ala
 50                  55                  60

Arg Phe Ser Gly Ser Gly Ser Gly Thr Glu Phe Thr Leu Thr Ile Ser
 65                  70                  75                  80

Ser Leu Gln Ser Glu Asp Phe Ala Val Tyr Tyr Cys Gln Gln Thr Ile
                 85                  90                  95

Glu Asp Pro Pro Thr Phe Gly Gly Gly Thr Lys Val Glu Ile Lys
                100                 105                 110
```

<210> SEQ ID NO 79
<211> LENGTH: 111
<212> TYPE: PRT
<213> ORGANISM: Artificial sequence
<220> FEATURE:
<223> OTHER INFORMATION: Light chain of h55A1-F3

<400> SEQUENCE: 79

```
Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                 20                  25                  30

Val Asp Ser Tyr Met His Trp Tyr Gln Gln Lys Pro Gly Lys Ala Pro
             35                  40                  45

Lys Leu Leu Ile Tyr Ala Ala Ser Asn Leu Ala Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Thr Ile
                 85                  90                  95

Glu Asp Pro Pro Thr Phe Gly Gly Gly Thr Lys Val Glu Ile Lys
                100                 105                 110
```

<210> SEQ ID NO 80
<211> LENGTH: 111
<212> TYPE: PRT
<213> ORGANISM: Artificial sequence
<220> FEATURE:
<223> OTHER INFORMATION: Light chain of h55A1-F4

<400> SEQUENCE: 80

```
Glu Ile Val Leu Thr Gln Ser Pro Gly Thr Leu Ser Leu Ser Pro Gly
 1               5                  10                  15

Glu Arg Ala Thr Leu Ser Cys Lys Ala Ser Gln Ser Val Asp Tyr Asp
                 20                  25                  30

Val Asp Ser Tyr Met His Trp Tyr Gln Gln Lys Pro Gly Gln Ala Pro
             35                  40                  45

Arg Leu Leu Ile Tyr Ala Ala Ser Asn Leu Ala Ser Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Thr Ile
                 85                  90                  95

Glu Asp Pro Pro Thr Phe Gly Gly Gly Thr Lys Val Glu Ile Lys
                100                 105                 110
```

<210> SEQ ID NO 81
<211> LENGTH: 120
<212> TYPE: PRT
<213> ORGANISM: Artificial sequence
<220> FEATURE:
<223> OTHER INFORMATION: Heavy chain of h55A1-F5

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Val Pro Thr Tyr Ala Gly Asp Phe
    50                  55                  60

Lys Gly Arg Phe Thr Phe Thr Leu Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Tyr Tyr Gly Arg Arg Tyr Phe Asp Val Trp Gly Lys
            100                 105                 110

Gly Thr Thr Val Thr Val Ser Ser
        115                 120

<210> SEQ ID NO 82
<211> LENGTH: 119
<212> TYPE: PRT
<213> ORGANISM: Artificial sequence
<220> FEATURE:
<223> OTHER INFORMATION: Heavy chain of h53A11-S1

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Met His Trp Val Arg Gln Ala Pro Gly Gln Arg Leu Glu Trp Met
        35                  40                  45

Gly Gly Ile Asn Pro Tyr Tyr Gly Gly Thr Thr Tyr Asn Glu Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asp Tyr Tyr Gly Ser Tyr Asn Tyr Trp Gly Gln Gly
            100                 105                 110

Thr Thr Val Thr Val Ser Ser
        115

<210> SEQ ID NO 83
<211> LENGTH: 107
<212> TYPE: PRT
<213> ORGANISM: Artificial sequence
<220> FEATURE:
<223> OTHER INFORMATION: Light chain of h53A11-S1

<400> SEQUENCE: 83

Glu Ile Val Met Thr Gln Ser Leu Ala Thr Leu Ser Val Ser Pro Gly
1               5                   10                  15

Glu Arg Ala Thr Leu Ser Cys Arg Ala Ser Gln Asp Ile Ser Asn Ser
            20                  25                  30

```
Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Asn Ser Trp Pro Tyr
                 85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial sequence
<220> FEATURE:
<223> OTHER INFORMATION: Light chain of h53A11-S2

<400> SEQUENCE: 84

Glu Ile Val Met Thr Gln Ser Leu Ala Thr Leu Ser Val Ser Pro Gly
 1               5                  10                  15

Glu Arg Ala Thr Leu Ser Cys Arg Ala Ser Gln Asp Ile Ser Asn Ser
             20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Asn Ser Trp Pro Tyr
                 85                  90                  95

Thr Phe Gly Gln Gly Thr Lys Leu Glu Ile Lys
            100                 105

<210> SEQ ID NO 85
<211> LENGTH: 107
<212> TYPE: PRT
<213> ORGANISM: Artificial sequence
<220> FEATURE:
<223> OTHER INFORMATION: Light chain of h53A11-S3

<400> SEQUENCE: 85

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Asp Ile Ser Asn Ser
             20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Asn Ser Trp Pro Tyr
                 85                  90                  95

Thr Phe Gly Gln Gly Thr Lys Leu Glu Ile Lys
            100                 105

<210> SEQ ID NO 86
```

```
<211> LENGTH: 119
<212> TYPE: PRT
<213> ORGANISM: Artificial sequence
<220> FEATURE:
<223> OTHER INFORMATION: Heavy chain of h53A11-S4

<400> SEQUENCE: 86
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Met His Trp Val Arg Gln Ala Pro Gly Gln Arg Leu Glu Trp Met
        35                  40                  45

Gly Gly Ile Asn Pro Tyr Tyr Gly Gly Thr Thr Tyr Asn Glu Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Gly Gly Ser Tyr Asn Tyr Trp Gly Gln Gly
            100                 105                 110

Thr Thr Val Thr Val Ser Ser
        115

```
<210> SEQ ID NO 87
<211> LENGTH: 120
<212> TYPE: PRT
<213> ORGANISM: Artificial sequence
<220> FEATURE:
<223> OTHER INFORMATION: Heavy chain of h23H8-S1

<400> SEQUENCE: 87
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asn
            20                  25                  30

Thr Ile His Trp Val Arg Gln Ala Pro Gly Gln Gly Leu Glu Trp Met
        35                  40                  45

Gly His Ile Asn Pro Tyr Tyr Gly Gly Thr Asn Asn Asn Glu Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Lys Gly Ile Tyr Tyr Ser Ser Pro Phe Asp Tyr Trp Gly Gln
            100                 105                 110

Gly Thr Thr Val Thr Val Ser Ser
        115                 120

```
<210> SEQ ID NO 88
<211> LENGTH: 107
<212> TYPE: PRT
<213> ORGANISM: Artificial sequence
<220> FEATURE:
<223> OTHER INFORMATION: Light chain of h23H8-S1

<400> SEQUENCE: 88
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Phe
                85                  90                  95

Thr Phe Gly Gln Gly Thr Lys Leu Glu Ile Lys
            100                 105

<210> SEQ ID NO 89
<211> LENGTH: 107
<212> TYPE: PRT
<213> ORGANISM: Artificial sequence
<220> FEATURE:
<223> OTHER INFORMATION: Light chain of h23H8-S2

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Ser Tyr Thr Ser Lys Leu His Ser Gly Val Pro Ser Arg Phe Ser Gly
 50                  55                  60

Ser Gly Ser Gly Thr Asp Phe Thr Leu Thr Ile Ser Ser Leu Gln Arg
 65                  70                  75                  80

Glu Asp Phe Ala Thr Tyr Tyr Cys Gln Gln Gly Asn Thr Leu Pro Phe
                85                  90                  95

Thr Phe Gly Gln Gly Thr Lys Leu Glu Ile Lys
            100                 105

<210> SEQ ID NO 90
<211> LENGTH: 107
<212> TYPE: PRT
<213> ORGANISM: Artificial sequence
<220> FEATURE:
<223> OTHER INFORMATION: Light chain of h23H8-S3

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Ser Tyr Thr Ser Lys Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Phe
                85                  90                  95

Thr Phe Gly Gln Gly Thr Lys Leu Glu Ile Lys
            100                 105

<210> SEQ ID NO 91
<211> LENGTH: 119
<212> TYPE: PRT
<213> ORGANISM: Artificial sequence
<220> FEATURE:
<223> OTHER INFORMATION: Heavy chain of h13B3-S1

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Ile Asn Pro Tyr Tyr Gly Gly Thr Ser Tyr Asn Glu Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Asn Tyr Val Gly Tyr Phe Asp Tyr Trp Gly Gln Gly
            100                 105                 110

Thr Thr Val Thr Val Ser Ser
        115

<210> SEQ ID NO 92
<211> LENGTH: 106
<212> TYPE: PRT
<213> ORGANISM: Artificial sequence
<220> FEATURE:
<223> OTHER INFORMATION: Light chain of h13B3-S1

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val His Tyr Met
            20                  25                  30

Tyr Trp Tyr Gln Gln Lys Pro Gly Gln Ala Pro Arg Leu Leu Ile Tyr
        35                  40                  45

Tyr Thr Ser Asn Leu Ala Pro Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Phe Thr Ser Ser Pro Tyr Thr
                85                  90                  95

Phe Gly Gly Gly Thr Lys Val Glu Ile Lys
            100                 105

<210> SEQ ID NO 93
<211> LENGTH: 119
<212> TYPE: PRT
<213> ORGANISM: Artificial sequence
<220> FEATURE:
<223> OTHER INFORMATION: Heavy chain of h13B3-S2

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Ile Asn Pro Tyr Tyr Gly Gly Thr Ser Tyr Asn Glu Lys Phe
    50                  55                  60

Lys Asp Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Tyr Gly Asn Tyr Val Gly Tyr Phe Asp Tyr Trp Gly Gln Gly
            100                 105                 110

Thr Thr Val Thr Val Ser Ser
        115

<210> SEQ ID NO 94
<211> LENGTH: 106
<212> TYPE: PRT
<213> ORGANISM: Artificial sequence
<220> FEATURE:
<223> OTHER INFORMATION: Light chain of h13B3-S3

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val His Tyr Met
            20                  25                  30

Tyr Trp Tyr Gln Gln Lys Pro Gly Gln Ala Pro Arg Leu Leu Ile Tyr
        35                  40                  45

Tyr Thr Ser Asn Leu Ala Pro Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Phe Thr Ser Ser Pro Tyr Thr
                85                  90                  95

Phe Gly Gly Gly Thr Lys Val Glu Ile Lys
            100                 105

<210> SEQ ID NO 95
<211> LENGTH: 119
<212> TYPE: PRT
<213> ORGANISM: Artificial sequence
<220> FEATURE:
<223> OTHER INFORMATION: Heavy chain of h12B10-S1

<400> SEQUENCE: 95

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Leu Ala His Ile Trp Trp Asn Asp Glu Lys Tyr Tyr Asn Pro Ser
    50                  55                  60

Leu Lys Ser Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
                85                  90                  95

```
Cys Ala Arg Asp His Leu Ala Tyr Tyr Phe Asp Val Trp Gly Gln Gly
            100                 105                 110

Thr Leu Val Thr Val Ser Ser
            115
```

<210> SEQ ID NO 96
<211> LENGTH: 107
<212> TYPE: PRT
<213> ORGANISM: Artificial sequence
<220> FEATURE:
<223> OTHER INFORMATION: Light chain of h12B10-S1

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Met
        35                  40                  45

Ala Tyr Pro Phe Thr Leu Gln Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Asn Leu Leu Trp
                85                  90                  95

Thr Phe Gly Gln Gly Thr Lys Val Glu Ile Lys
            100                 105
```

<210> SEQ ID NO 97
<211> LENGTH: 119
<212> TYPE: PRT
<213> ORGANISM: Artificial sequence
<220> FEATURE:
<223> OTHER INFORMATION: Heavy chain of h12B10-S2

<400> SEQUENCE: 97

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Leu Ala His Ile Trp Trp Asn Asp Glu Lys Tyr Tyr Asn Pro Ser
    50                  55                  60

Leu Lys Ser Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
                85                  90                  95

Cys Ala Arg Asp His Leu Ala Tyr Phe Asp Leu Trp Gly Gln Gly
            100                 105                 110

Thr Leu Val Thr Val Ser Ser
            115
```

<210> SEQ ID NO 98
<211> LENGTH: 119
<212> TYPE: PRT
<213> ORGANISM: Artificial sequence
<220> FEATURE:
<223> OTHER INFORMATION: Heavy chain of h12B10-S3

```
<400> SEQUENCE: 98

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Leu Ala His Ile Trp Trp Asn Asp Glu Lys Tyr Tyr Asn Pro Ser
    50                  55                  60

Leu Lys Ser Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
                85                  90                  95

Cys Ala Arg Asp His Leu Ala Phe Phe Asp Leu Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Artificial sequence
<220> FEATURE:
<223> OTHER INFORMATION: Heavy chain of h12B10-S4

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Ser
            20                  25                  30

Gly Met Gly Val Gly Trp Val Arg Gln Ala Pro Gly Lys Gly Leu Glu
        35                  40                  45

Trp Leu Ala His Ile Trp Trp Asn Asp Glu Lys Tyr Tyr Asn Pro Ser
    50                  55                  60

Leu Lys Ser Arg Phe Thr Ile Ser Arg Asp Asp Ser Lys Asn Thr Leu
65                  70                  75                  80

Tyr Leu Gln Met Asn Ser Leu Lys Thr Glu Asp Thr Ala Val Tyr Tyr
                85                  90                  95

Cys Ala Arg Asp His Leu Val Phe Phe Asp Leu Trp Gly Gln Gly
            100                 105                 110

Thr Leu Val Thr Val Ser Ser
        115

<210> SEQ ID NO 100
<211> LENGTH: 116
<212> TYPE: PRT
<213> ORGANISM: Artificial sequence
<220> FEATURE:
<223> OTHER INFORMATION: Heavy chain of h16F6-S1

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile Ala Trp Val Arg Gln Ala Pro Gly Gln Gly Leu Glu Trp Met
        35                  40                  45
```

```
Gly Glu Ile Leu Pro Gly Ser Ala Lys Thr Lys Tyr Asn Lys Lys Phe
            50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Val Tyr Asp Tyr Gly Ala Asp Tyr Trp Gly Gln Gly Thr Thr Val
               100                 105                 110

Thr Val Ser Ser
            115

<210> SEQ ID NO 101
<211> LENGTH: 107
<212> TYPE: PRT
<213> ORGANISM: Artificial sequence
<220> FEATURE:
<223> OTHER INFORMATION: Light chain of h16F6-S1

<400> SEQUENCE: 101

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Tyr Thr Ala
                20                  25                  30

Val Ala Trp Tyr Gln Gln Lys Pro Gly Lys Ser Pro Lys Leu Leu Ile
             35                  40                  45

Tyr Ser Ala Ser Tyr Arg Phe Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Ile Pro Arg
                 85                  90                  95

Thr Phe Gly Gly Gly Thr Lys Val Glu Ile Lys
            100                 105

<210> SEQ ID NO 102
<211> LENGTH: 107
<212> TYPE: PRT
<213> ORGANISM: Artificial sequence
<220> FEATURE:
<223> OTHER INFORMATION: Light chain of h16F6-S2

<400> SEQUENCE: 102

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Tyr Thr Ala
                20                  25                  30

Val Ala Trp Tyr Gln Gln Lys Pro Gly Lys Ser Pro Lys Leu Leu Ile
             35                  40                  45

Tyr Ser Ala Ser Tyr Arg Phe Thr Gly Val Pro Ser Arg Phe Ser Gly
         50                  55                  60

Ser Gly Ala Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Ile Pro Arg
                 85                  90                  95

Thr Phe Gly Gly Gly Thr Lys Val Glu Ile Lys
            100                 105
```

```
<210> SEQ ID NO 103
<211> LENGTH: 107
<212> TYPE: PRT
<213> ORGANISM: Artificial sequence
<220> FEATURE:
<223> OTHER INFORMATION: Light chain of h16F6-S3

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Tyr Thr Ala
            20                  25                  30

Val Ala Trp Tyr Gln Gln Lys Pro Gly Lys Ser Pro Lys Leu Leu Ile
        35                  40                  45

Tyr Ser Ala Ser Tyr Arg Phe Thr Gly Val Pro Ser Arg Phe Thr Gly
    50                  55                  60

Ser Gly Ala Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Ile Pro Arg
                85                  90                  95

Thr Phe Gly Gly Gly Thr Lys Val Glu Ile Lys
            100                 105

<210> SEQ ID NO 104
<211> LENGTH: 107
<212> TYPE: PRT
<213> ORGANISM: Artificial sequence
<220> FEATURE:
<223> OTHER INFORMATION: Light chain of h16F6-S4

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Tyr Thr Ala
            20                  25                  30

Val Ala Trp Tyr Gln Gln Lys Pro Gly Lys Ser Pro Lys Leu Leu Ile
        35                  40                  45

Tyr Ser Ala Ser Tyr Arg Phe Thr Gly Val Pro Ser Arg Phe Thr Gly
    50                  55                  60

Ser Gly Ala Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Ile Pro Arg
                85                  90                  95

Thr Phe Gly Gly Gly Thr Lys Val Glu Ile Lys
            100                 105

<210> SEQ ID NO 105
<211> LENGTH: 107
<212> TYPE: PRT
<213> ORGANISM: Artificial sequence
<220> FEATURE:
<223> OTHER INFORMATION: Light chain of h16F6-S5

<400> SEQUENCE: 105

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asp Val Tyr Thr Ala
            20                  25                  30

Val Ala Trp Tyr Gln Gln Lys Pro Gly Lys Ser Pro Lys Leu Leu Ile
        35                  40                  45
```

```
Tyr Ser Ala Ser Tyr Arg Phe Thr Gly Val Pro Ser Arg Phe Thr Gly
        50                  55                  60

Ser Gly Ala Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Ile Pro Arg
                85                  90                  95

Thr Phe Gly Gly Gly Thr Lys Val Glu Ile Lys
                100                 105

<210> SEQ ID NO 106
<211> LENGTH: 17
<212> TYPE: PRT
<213> ORGANISM: Artificial sequence
<220> FEATURE:
<223> OTHER INFORMATION: CDR2 of h55A1-6 heavy chain

<400> SEQUENCE: 106

Trp Ile Asn Thr Tyr Ser Gly Val Gly Thr Tyr Ala Gly Glu Phe Lys
1               5                   10                  15

Gly

<210> SEQ ID NO 107
<211> LENGTH: 120
<212> TYPE: PRT
<213> ORGANISM: Artificial Sequence
<220> FEATURE:
<223> OTHER INFORMATION: Heavy chain of 55A1

<400> SEQUENCE: 107

Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Ser Gly Val Pro Tyr Ala Gly Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Gly Tyr Tyr Gly Arg Arg Tyr Phe Asp Val Trp Gly Thr
                100                 105                 110

Gly Thr Thr Val Thr Val Ser Ser
        115                 120

<210> SEQ ID NO 108
<211> LENGTH: 111
<212> TYPE: PRT
<213> ORGANISM: Artificial Sequence
<220> FEATURE:
<223> OTHER INFORMATION: Light chain of 55A1

<400> SEQUENCE: 108

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Val Asp Ser Tyr Met His Trp Tyr Gln Gln Lys Pro Gly Gln Pro Pro
```

35                  40                  45
Lys Leu Leu Ile Tyr Ala Ala Ser Asn Leu Ala Ser Gly Ile Pro Ala
         50                  55                  60

Arg Phe Ser Gly Gly Gly Ser Gly Thr Asp Phe Thr Leu Asn Ile His
 65                  70                  75                  80

Pro Val Glu Glu Glu Asp Val Ala Thr Tyr Tyr Cys Gln Gln Thr Ile
                     85                  90                  95

Glu Asp Pro Pro Thr Phe Gly Gly Thr Lys Leu Glu Ile Lys
             100                 105                 110

<210> SEQ ID NO 109
<211> LENGTH: 120
<212> TYPE: PRT
<213> ORGANISM: Artificial Sequence
<220> FEATURE:
<223> OTHER INFORMATION: Heavy chain of 7D4

<400> SEQUENCE: 109

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30

Gly Met Asn Trp Val Lys Gln Ala Pro Gly Lys Asp Leu Lys Trp Met
         35                  40                  45

Gly Trp Ile Asn Thr Tyr Ser Gly Val Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
             85                  90                  95

Ala Arg Phe Ser Tyr Tyr Gly Arg His Tyr Phe Asp Tyr Trp Gly Gln
            100                 105                 110

Gly Thr Thr Leu Thr Val Ser Ser
        115                 120

<210> SEQ ID NO 110
<211> LENGTH: 112
<212> TYPE: PRT
<213> ORGANISM: Artificial Sequence
<220> FEATURE:
<223> OTHER INFORMATION: Light chain of  7D4

<400> SEQUENCE: 110

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Met Asn Trp Tyr Gln Gln Lys Pro Gly Gln Pro Pro
         35                  40                  45

Gln Leu Leu Ile Tyr Ala Ala Ser Asn Leu Gly Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys His Gln Ser Thr
                 85                  90                  95

Asp Asp Pro Pro Trp Thr Phe Gly Gly Gly Thr Lys Leu Glu Ile Lys
            100                 105                 110

<210> SEQ ID NO 111
<211> LENGTH: 120
<212> TYPE: PRT
<213> ORGANISM: Artificial Sequence
<220> FEATURE:
<223> OTHER INFORMATION: Heavy chain of 14A1

<400> SEQUENCE: 111

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Phe Lys Asn Glu Asp Thr Ala Thr Tyr Phe Cys
                85                  90                  95

Ala Arg Phe Ser Tyr Tyr Gly Arg His Tyr Phe Asp Tyr Trp Gly Gln
            100                 105                 110

Gly Thr Ala Leu Thr Ala Ser Ser
        115                 120

<210> SEQ ID NO 112
<211> LENGTH: 112
<212> TYPE: PRT
<213> ORGANISM: Artificial Sequence
<220> FEATURE:
<223> OTHER INFORMATION: Light chain of 14A1

<400> SEQUENCE: 112

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Lys Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Thr
                85                  90                  95

Asp Asp Pro Pro Trp Thr Phe Gly Gly Gly Thr Lys Leu Glu Ile Lys
            100                 105                 110

<210> SEQ ID NO 113
<211> LENGTH: 120
<212> TYPE: PRT
<213> ORGANISM: Artificial Sequence
<220> FEATURE:
<223> OTHER INFORMATION: Heavy chain of 2D5

<400> SEQUENCE: 113

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr

Gly Met Asn Trp Val Lys Gln Ala Pro Gly Lys Gly Leu Lys Trp Met
            20                  25                  30
        35                  40                  45

Gly Trp Ile Asn Thr Tyr Ser Gly Val Pro Thr Tyr Thr Asp Asp Phe
        50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Phe Ser Tyr Tyr Gly Arg His Tyr Phe Asp Tyr Trp Gly Gln
                100                 105                 110

Gly Thr Thr Leu Thr Val Ser Ser
                115                 120

<210> SEQ ID NO 114
<211> LENGTH: 112
<212> TYPE: PRT
<213> ORGANISM: Artificial Sequence
<220> FEATURE:
<223> OTHER INFORMATION: Light chain of 2D5

<400> SEQUENCE: 114

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met His Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Asp Asp Pro Pro Trp Thr Phe Gly Gly Gly Thr Lys Leu Glu Ile Lys
                100                 105                 110

<210> SEQ ID NO 115
<211> LENGTH: 119
<212> TYPE: PRT
<213> ORGANISM: Artificial Sequence
<220> FEATURE:
<223> OTHER INFORMATION: Heavy chain of 53A11

<400> SEQUENCE: 115

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
                20                  25                  30

Thr Met His Trp Val Lys Gln Ser His Gly Lys Ser Leu Glu Trp Ile
            35                  40                  45

Gly Gly Ile Asn Pro Tyr Tyr Gly Gly Thr Thr Tyr Asn Glu Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

```
Ala Lys Gly Asp Tyr Tyr Gly Gly Ser Tyr Asn Tyr Trp Gly Gln Gly
            100                 105                 110

Thr Thr Leu Thr Val Ser Ser
            115

<210> SEQ ID NO 116
<211> LENGTH: 107
<212> TYPE: PRT
<213> ORGANISM: Artificial Sequence
<220> FEATURE:
<223> OTHER INFORMATION: Light chain of  53A11

<400> SEQUENCE: 116

Asp Ile Val Leu Thr Gln Ser Leu Ala Thr Leu Ser Val Thr Pro Gly
1               5                   10                  15

Asp Ser Val Ser Leu Ser Cys Arg Ala Ser Gln Asp Ile Ser Asn Ser
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 117
<211> LENGTH: 119
<212> TYPE: PRT
<213> ORGANISM: Artificial Sequence
<220> FEATURE:
<223> OTHER INFORMATION: Heavy chain of  13B3

<400> SEQUENCE: 117

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Ser Ile Asn Pro Tyr Tyr Gly Gly Thr Ser Tyr Asn Glu Lys Phe
    50                  55                  60

Lys Asp Lys Ala Thr Leu Thr Val Asp Lys Ser Ser Asn Thr Ala Tyr
65                  70                  75                  80

Met Glu Phe Arg Ser Leu Thr Ser Glu Asp Cys Ala Val Tyr Tyr Cys
                85                  90                  95

Ala Arg Tyr Gly Asn Tyr Val Gly Tyr Phe Asp Tyr Trp Gly Gln Gly
            100                 105                 110

Thr Thr Leu Thr Val Ser Ser
            115

<210> SEQ ID NO 118
<211> LENGTH: 106
<212> TYPE: PRT
<213> ORGANISM: Artificial Sequence
<220> FEATURE:
<223> OTHER INFORMATION: Light chain of  13B3
```

-continued

```
<400> SEQUENCE: 118

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Val His Tyr Met
            20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Asp Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 119
<211> LENGTH: 120
<212> TYPE: PRT
<213> ORGANISM: Artificial Sequence
<220> FEATURE:
<223> OTHER INFORMATION: Heavy chain of 23H8

<400> SEQUENCE: 119

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Asn
            20                  25                  30

Thr Ile His Trp Val Lys Gln Ser His Gly Lys Ser Leu Glu Trp Ile
        35                  40                  45

Gly His Ile Asn Pro Tyr Tyr Gly Gly Thr Asn Asn Asn Glu Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Ile Tyr Tyr Cys
                85                  90                  95

Ala Arg Lys Gly Ile Tyr Tyr Ser Ser Pro Phe Asp Tyr Trp Gly Gln
            100                 105                 110

Gly Thr Thr Leu Thr Val Ser Ser
        115                 120

<210> SEQ ID NO 120
<211> LENGTH: 107
<212> TYPE: PRT
<213> ORGANISM: Artificial Sequence
<220> FEATURE:
<223> OTHER INFORMATION: Light chain of 23H8

<400> SEQUENCE: 120

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Ser Tyr Thr Ser Lys Leu His Ser Gly Val Pro Ser Arg Phe Ser Gly
    50                  55                  60
```

```
Ser Gly Ser Gly Thr Asp Tyr Ser Leu Thr Ile Ser Asn Leu Glu Arg
 65                  70                  75                  80

Glu Asp Phe Ala Thr Tyr Phe Cys Gln Gln Gly Asn Thr Leu Pro Phe
                 85                  90                  95

Thr Phe Gly Ser Gly Thr Asn Leu Glu Ile Lys
                100                 105

<210> SEQ ID NO 121
<211> LENGTH: 122
<212> TYPE: PRT
<213> ORGANISM: Artificial Sequence
<220> FEATURE:
<223> OTHER INFORMATION: Heavy chain of  16B3

<400> SEQUENCE: 121

Asp Val Lys Leu Val Glu Ser Gly Gly Leu Val Gln Pro Gly Gly
1               5                   10                  15

Ser Leu Lys Leu Ser Cys Thr Ala Ser Gly Phe Thr Phe Ser Gly Tyr
                20                  25                  30

Thr Met Ser Trp Val Arg Gln Thr Pro Glu Lys Arg Leu Glu Leu Val
                35                  40                  45

Ala Glu Ile Ser Phe Ala Arg Asp Arg Ala Phe Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Leu Gly Gly Arg Asn His Asp Tyr Trp Tyr Phe Asp Val Trp
                100                 105                 110

Gly Thr Gly Thr Thr Val Thr Val Ser Ser
        115                 120

<210> SEQ ID NO 122
<211> LENGTH: 111
<212> TYPE: PRT
<213> ORGANISM: Artificial Sequence
<220> FEATURE:
<223> OTHER INFORMATION: Light chain of  16B3

<400> SEQUENCE: 122

Asp Ile Val Leu Thr Gln Ser Pro Thr Ser Leu Ala Val Ser Pro Gly
1               5                   10                  15

Gln Arg Ala Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Arg Pro
        35                  40                  45

Gln Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Val Tyr Phe Cys Gln Gln Ser Trp
                85                  90                  95

Lys Val Pro Phe Thr Phe Gly Ser Gly Thr Lys Leu Glu Ile Lys
                100                 105                 110

<210> SEQ ID NO 123
<211> LENGTH: 122
<212> TYPE: PRT
<213> ORGANISM: Artificial Sequence
```

```
<220> FEATURE:
<223> OTHER INFORMATION: Heavy chain of 16E7

<400> SEQUENCE: 123

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Phe Thr Arg Ser Arg Ala Phe Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Gly Gly Asn Asn Tyr Asp Tyr Trp Tyr Phe Asp Val Trp
            100                 105                 110

Gly Thr Gly Thr Thr Val Thr Val Ser Ser
        115                 120

<210> SEQ ID NO 124
<211> LENGTH: 111
<212> TYPE: PRT
<213> ORGANISM: Artificial Sequence
<220> FEATURE:
<223> OTHER INFORMATION: Light chain of 16E7

<400> SEQUENCE: 124

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Arg Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Trp
                85                  90                  95

Lys Val Pro Phe Thr Phe Gly Ser Gly Thr Lys Leu Glu Ile Lys
            100                 105                 110

<210> SEQ ID NO 125
<211> LENGTH: 119
<212> TYPE: PRT
<213> ORGANISM: Artificial Sequence
<220> FEATURE:
<223> OTHER INFORMATION: Heavy chain of 14E1

<400> SEQUENCE: 125

Gln Val Gln Leu Gln Gln Ser Gly Ala Glu Leu Val Lys Pro Gly Ala
1               5                   10                  15

Ser Val Arg Leu Ser Cys Lys Ala Ser Gly Tyr Thr Phe Thr Lys Tyr
            20                  25                  30

Thr Ile His Trp Val Lys Gln Arg Ser Gly Gln Gly Leu Glu Trp Ile
        35                  40                  45
```

Gly Trp Phe Tyr Pro Gly Ser Asp Ser Ile Lys Tyr Asn Glu Lys Phe
            50                  55                  60

Lys Asp Lys Ala Thr Leu Thr Ala Asp Lys Ser Ser Arg Thr Val Tyr
65                  70                  75                  80

Met Glu Leu Ser Arg Leu Thr Ser Glu Asp Ser Ala Val Tyr Phe Cys
                85                  90                  95

Ala Arg His Glu Glu Tyr Thr Asn Ser Leu Ala Tyr Trp Gly Gln Gly
            100                 105                 110

Thr Leu Val Thr Val Ser Ala
            115

<210> SEQ ID NO 126
<211> LENGTH: 107
<212> TYPE: PRT
<213> ORGANISM: Artificial Sequence
<220> FEATURE:
<223> OTHER INFORMATION: Light chain of 14E1

<400> SEQUENCE: 126

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Trp
                85                  90                  95

Thr Phe Gly Gly Gly Thr Asn Leu Glu Ile Lys
            100                 105

<210> SEQ ID NO 127
<211> LENGTH: 118
<212> TYPE: PRT
<213> ORGANISM: Artificial Sequence
<220> FEATURE:
<223> OTHER INFORMATION: Heavy chain of 19E7

<400> SEQUENCE: 127

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile His Pro Tyr Ser Gly Asn Asn Asn Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Arg Leu Thr Ser Glu Asp Ser Ala Val Tyr Tyr Cys
                85                  90                  95

Ala Arg Tyr Asp Ser Asn Tyr Val Phe Ala Tyr Trp Gly Gln Gly Thr
            100                 105                 110

Leu Val Thr Val Ser Ala
            115

<210> SEQ ID NO 128
<211> LENGTH: 105
<212> TYPE: PRT
<213> ORGANISM: Artificial Sequence
<220> FEATURE:
<223> OTHER INFORMATION: Light chain of 19E7

<400> SEQUENCE: 128

Gln Ile Val Leu Thr Gln Ser Pro Ala Ile Met Ser Ala Ser Pro Gly
1               5                   10                  15

Glu Gly Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Asp Ser Tyr Leu Thr Phe
                85                  90                  95

Gly Ser Gly Thr Lys Leu Glu Val Lys
            100                 105

<210> SEQ ID NO 129
<211> LENGTH: 116
<212> TYPE: PRT
<213> ORGANISM: Artificial Sequence
<220> FEATURE:
<223> OTHER INFORMATION: Heavy chain of 16F6

<400> SEQUENCE: 129

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Ala Trp Val Lys Gln Arg Pro Gly His Gly Leu Glu Trp Ile
        35                  40                  45

Gly Glu Ile Leu Pro Gly Ser Ala Lys Thr Lys Tyr Asn Lys Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Val Tyr Asp Tyr Gly Ala Asp Tyr Trp Gly Gln Gly Thr Ser Val
            100                 105                 110

Thr Val Ser Ser
        115

<210> SEQ ID NO 130
<211> LENGTH: 107
<212> TYPE: PRT
<213> ORGANISM: Artificial Sequence
<220> FEATURE:
<223> OTHER INFORMATION: Light chain of 16F6

<400> SEQUENCE: 130

Asp Ile Val Met Thr Gln Ser His Lys Phe Met Ser Thr Ser Val Gly
1               5                   10                  15

-continued

```
Asp Arg Val Ser Ile Thr Cys Lys Ala Ser Gln Asp Val Tyr Thr Ala
            20              25              30

Val Ala Trp Tyr Gln Gln Lys Pro Gly Gln Ser Pro Lys Leu Leu Ile
        35              40              45

Tyr Ser Ala Ser Tyr Arg Phe Thr Gly Val Pro Asp Arg Phe Thr Gly
    50              55              60

Ser Gly Ala Gly Thr Glu Phe Thr Phe Thr Ile Asn Ser Val Gln Ala
65              70              75              80

Glu Asp Leu Ala Val Tyr Tyr Cys Gln Gln His Tyr Ser Ile Pro Arg
            85              90              95

Thr Phe Gly Gly Gly Thr Lys Leu Glu Ile Lys
            100             105
```

The invention claimed is:

1. A humanized monoclonal antibody or an antibody fragment thereof,
  selected from the group of
  1) a humanized monoclonal antibody or an antibody fragment thereof,
    having
      a heavy chain variable region
        including three CDRs having the amino acid sequence of SEQ ID NO: 2, the amino acid sequence of SEQ ID NO: 3 and the amino acid sequence of SEQ ID NO: 8, and
      a light chain variable region
        including three CDRs having the amino acid sequence of SEQ ID NO: 5, the amino acid sequence of SEQ ID NO: 6 and the amino acid sequence of SEQ ID NO: 7;
  2) a humanized monoclonal antibody or an antibody fragment thereof,
    having
      a heavy chain variable region
        including three CDRs having the amino acid sequence of SEQ ID NO: 2, the amino acid sequence of SEQ ID NO: 3 and the amino acid sequence of SEQ ID NO: 8, and
      a light chain variable region
        including three CDRs having the amino acid sequence of SEQ ID NO: 5, the amino acid sequence of SEQ ID NO: 6 and the amino acid sequence of SEQ ID NO: 9;
  3) a humanized monoclonal antibody or an antibody fragment thereof,
    having
      a heavy chain variable region
        including three CDRs having the amino acid sequence of SEQ ID NO: 2, the amino acid sequence of SEQ ID NO: 3 and the amino acid sequence of SEQ ID NO: 10, and
      a light chain variable region
        including three CDRs having the amino acid sequence of SEQ ID NO: 5, the amino acid sequence of SEQ ID NO: 6 and the amino acid sequence of SEQ ID NO: 7;
  4) a humanized monoclonal antibody or an antibody fragment thereof,
    having
      a heavy chain variable region
        including three CDRs having the amino acid sequence of SEQ ID NO: 2, the amino acid sequence of SEQ ID NO: 3 and the amino acid sequence of SEQ ID NO: 10, and
      a light chain variable region
        including three CDRs having the amino acid sequence of SEQ ID NO: 5, the amino acid sequence of SEQ ID NO: 6 and the amino acid sequence of SEQ ID NO: 9;
  5) a humanized monoclonal antibody or an antibody fragment thereof,
    having
      a heavy chain variable region
        including three CDRs having the amino acid sequence of SEQ ID NO: 11, the amino acid sequence of SEQ ID NO: 12 and the amino acid sequence of SEQ ID NO: 10, and
      a light chain variable region
        including three CDRs having the amino acid sequence of SEQ ID NO: 5, the amino acid sequence of SEQ ID NO: 6 and the amino acid sequence of SEQ ID NO: 7;
  6) a humanized monoclonal antibody or an antibody fragment thereof,
    having
      a heavy chain variable region
        including three CDRs having the amino acid sequence of SEQ ID NO: 11, the amino acid sequence of SEQ ID NO: 12 and the amino acid sequence of SEQ ID NO: 10, and
      a light chain variable region
        including three CDRs having the amino acid sequence of SEQ ID NO: 5, the amino acid sequence of SEQ ID NO: 6 and the amino acid sequence of SEQ ID NO: 9;
  7) a humanized monoclonal antibody or an antibody fragment thereof,
    having
      a heavy chain variable region
        including three CDRs having the amino acid sequence of SEQ ID NO: 19, the amino acid sequence of SEQ ID NO: 14 and the amino acid sequence of SEQ ID NO: 20, and
      a light chain variable region
        including three CDRs having the amino acid sequence of SEQ ID NO: 16, the amino acid sequence of SEQ ID NO: 17 and the amino acid sequence of SEQ ID NO: 18;

8) a humanized monoclonal antibody or an antibody fragment thereof,
having
a heavy chain variable region
including three CDRs having the amino acid sequence of SEQ ID NO: 19, the amino acid sequence of SEQ ID NO: 14 and the amino acid sequence of SEQ ID NO: 20, and
a light chain variable region
including three CDRs having the amino acid sequence of SEQ ID NO: 16, the amino acid sequence of SEQ ID NO: 17 and the amino acid sequence of SEQ ID NO: 21;
9) a humanized monoclonal antibody or an antibody fragment thereof,
having
a heavy chain variable region
including three CDRs having the amino acid sequence of SEQ ID NO: 22, the amino acid sequence of SEQ ID NO: 23 and the amino acid sequence of SEQ ID NO: 24, and
a light chain variable region
including three CDRs having the amino acid sequence of SEQ ID NO: 16, the amino acid sequence of SEQ ID NO: 17 and the amino acid sequence of SEQ ID NO: 18;
10) a humanized monoclonal antibody or an antibody fragment thereof,
having
a heavy chain variable region
including three CDRs having the amino acid sequence of SEQ ID NO: 22, the amino acid sequence of SEQ ID NO: 23 and the amino acid sequence of SEQ ID NO: 24, and
a light chain variable region
including three CDRs having the amino acid sequence of SEQ ID NO: 16, the amino acid sequence of SEQ ID NO: 17 and the amino acid sequence of SEQ ID NO: 21;
11) a humanized monoclonal antibody or an antibody fragment thereof,
having
a heavy chain variable region
including three CDRs having the amino acid sequence of SEQ ID NO: 25, the amino acid sequence of SEQ ID NO: 106 and the amino acid sequence of SEQ ID NO: 24, and
a light chain variable region
including three CDRs having the amino acid sequence of SEQ ID NO: 16, the amino acid sequence of SEQ ID NO: 17 and the amino acid sequence of SEQ ID NO: 18;
12) a humanized monoclonal antibody or an antibody fragment thereof,
having
a heavy chain variable region
including three CDRs having the amino acid sequence of SEQ ID NO: 25, the amino acid sequence of SEQ ID NO: 106 and the amino acid sequence of SEQ ID NO: 24, and
a light chain variable region
including three CDRs having the amino acid sequence of SEQ ID NO: 16, the amino acid sequence of SEQ ID NO: 17 and the amino acid sequence of SEQ ID NO: 21;
13) a humanized monoclonal antibody or an antibody fragment thereof,
having
a heavy chain variable region
including three CDRs having the amino acid sequence of SEQ ID NO: 44, the amino acid sequence of SEQ ID NO: 45 and the amino acid sequence of SEQ ID NO: 46, and
a light chain variable region
including three CDRs having the amino acid sequence of SEQ ID NO: 47, the amino acid sequence of SEQ ID NO: 48 and the amino acid sequence of SEQ ID NO: 49;
14) a humanized monoclonal antibody or an antibody fragment thereof,
having
a heavy chain variable region
including three CDRs having the amino acid sequence of SEQ ID NO: 44, the amino acid sequence of SEQ ID NO: 45 and the amino acid sequence of SEQ ID NO: 50, and
a light chain variable region
including three CDRs having the amino acid sequence of SEQ ID NO: 47, the amino acid sequence of SEQ ID NO: 48 and the amino acid sequence of SEQ ID NO: 49;
15) a humanized monoclonal antibody or an antibody fragment thereof,
having
a heavy chain variable region
including three CDRs having the amino acid sequence of SEQ ID NO: 44, the amino acid sequence of SEQ ID NO: 45 and the amino acid sequence of SEQ ID NO: 51, and
a light chain variable region
including three CDRs having the amino acid sequence of SEQ ID NO: 47, the amino acid sequence of SEQ ID NO: 48 and the amino acid sequence of SEQ ID NO: 49;
16) a humanized monoclonal antibody or an antibody fragment thereof,
having
a heavy chain variable region
including three CDRs having the amino acid sequence of SEQ ID NO: 52, the amino acid sequence of SEQ ID NO: 45 and the amino acid sequence of SEQ ID NO: 53, and
a light chain variable region
including three CDRs having the amino acid sequence of SEQ ID NO: 47, the amino acid sequence of SEQ ID NO: 48 and the amino acid sequence of SEQ ID NO: 49.

2. The humanized monoclonal antibody or an antibody fragment thereof according to claim 1, wherein said antibody fragment is Fab, F(ab')$_2$, Fab', scFv, dsFv or Diabody.

3. A humanized monoclonal antibody or an antibody fragment thereof,
selected from the group of
1) a humanized monoclonal antibody or an antibody fragment thereof,
having
a heavy chain variable region having the amino acid sequence of SEQ ID NO: 60, and
a light chain variable region having the amino acid sequence of SEQ ID NO: 61;

2) a humanized monoclonal antibody or an antibody fragment thereof,
having
   a heavy chain variable region having the amino acid sequence of SEQ ID NO: 62, and
   a light chain variable region having the amino acid sequence of SEQ ID NO: 61;
3) a humanized monoclonal antibody or an antibody fragment thereof,
having
   a heavy chain variable region having the amino acid sequence of SEQ ID NO: 63, and
   a light chain variable region having the amino acid sequence of SEQ ID NO: 61;
4) a humanized monoclonal antibody or an antibody fragment thereof,
having
   a heavy chain variable region having the amino acid sequence of SEQ ID NO: 63, and
   a light chain variable region having the amino acid sequence of SEQ ID NO: 64;
5) a humanized monoclonal antibody or an antibody fragment thereof,
having
   a heavy chain variable region having the amino acid sequence of SEQ ID NO: 65, and
   a light chain variable region having the amino acid sequence of SEQ ID NO: 61;
6) a humanized monoclonal antibody or an antibody fragment thereof,
having
   a heavy chain variable region having the amino acid sequence of SEQ ID NO: 65, and
   a light chain variable region having the amino acid sequence of SEQ ID NO: 64;
7) a humanized monoclonal antibody or an antibody fragment thereof,
having
   a heavy chain variable region having the amino acid sequence of SEQ ID NO: 66, and
   a light chain variable region having the amino acid sequence of SEQ ID NO: 61;
8) a humanized monoclonal antibody or an antibody fragment thereof,
having
   a heavy chain variable region having the amino acid sequence of SEQ ID NO: 66, and
   a light chain variable region having the amino acid sequence of SEQ ID NO: 64;
9) a humanized monoclonal antibody or an antibody fragment thereof,
having
   a heavy chain variable region having the amino acid sequence of SEQ ID NO: 62, and
   a light chain variable region having the amino acid sequence of SEQ ID NO: 67;
10) a humanized monoclonal antibody or an antibody fragment thereof,
having
   a heavy chain variable region having the amino acid sequence of SEQ ID NO: 62, and
   a light chain variable region having the amino acid sequence of SEQ ID NO: 68;
11) a humanized monoclonal antibody or an antibody fragment thereof,
having
   a heavy chain variable region having the amino acid sequence of SEQ ID NO: 62, and
   a light chain variable region having the amino acid sequence of SEQ ID NO: 69;
12) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 71;
13) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 71;
14) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 73;
15) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 71;
16) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 73;
17) a humanized monoclonal antibody or an antibody fragment thereof,
having
   a heavy chain variable region having the amino acid sequence of SEQ ID NO: 75, and
   a light chain variable region having the amino acid sequence of SEQ ID NO: 71;
18) a humanized monoclonal antibody or an antibody fragment thereof,
having
   a heavy chain variable region having the amino acid sequence of SEQ ID NO: 75, and
   a light chain variable region having the amino acid sequence of SEQ ID NO: 73;
19) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 76;

20) a humanized monoclonal antibody or an antibody fragment thereof,
having
   a heavy chain variable region having the amino acid sequence of SEQ ID NO: 77, and
   a light chain variable region having the amino acid sequence of SEQ ID NO: 78;
21) a humanized monoclonal antibody or an antibody fragment thereof,
having
   a heavy chain variable region having the amino acid sequence of SEQ ID NO: 77, and
   a light chain variable region having the amino acid sequence of SEQ ID NO: 79;
22) a humanized monoclonal antibody or an antibody fragment thereof,
having
   a heavy chain variable region having the amino acid sequence of SEQ ID NO: 77, and
   a light chain variable region having the amino acid sequence of SEQ ID NO: 80;
23) a humanized monoclonal antibody or an antibody fragment thereof,
having
   a heavy chain variable region having the amino acid sequence of SEQ ID NO: 81, and
   a light chain variable region having the amino acid sequence of SEQ ID NO: 79;
24) a humanized monoclonal antibody or an antibody fragment thereof,
having
   a heavy chain variable region having the amino acid sequence of SEQ ID NO: 81, and
   a light chain variable region having the amino acid sequence of SEQ ID NO: 78;
25) a humanized monoclonal antibody or an antibody fragment thereof,
having
   a heavy chain variable region having the amino acid sequence of SEQ ID NO: 82, and
   a light chain variable region having the amino acid sequence of SEQ ID NO: 83;
26) a humanized monoclonal antibody or an antibody fragment thereof,
having
   a heavy chain variable region having the amino acid sequence of SEQ ID NO: 82, and
   a light chain variable region having the amino acid sequence of SEQ ID NO: 84;
27) a humanized monoclonal antibody or an antibody fragment thereof,
having
   a heavy chain variable region having the amino acid sequence of SEQ ID NO: 82, and
   a light chain variable region having the amino acid sequence of SEQ ID NO: 85;
28) a humanized monoclonal antibody or an antibody fragment thereof,
having
   a heavy chain variable region having the amino acid sequence of SEQ ID NO: 86, and
   a light chain variable region having the amino acid sequence of SEQ ID NO: 85;
29) a humanized monoclonal antibody or an antibody fragment thereof,
having
   a heavy chain variable region having the amino acid sequence of SEQ ID NO: 87, and
   a light chain variable region having the amino acid sequence of SEQ ID NO: 88;
30) a humanized monoclonal antibody or an antibody fragment thereof,
having
   a heavy chain variable region having the amino acid sequence of SEQ ID NO: 87, and
   a light chain variable region having the amino acid sequence of SEQ ID NO: 89;
31) a humanized monoclonal antibody or an antibody fragment thereof,
having
   a heavy chain variable region having the amino acid sequence of SEQ ID NO: 87, and
   a light chain variable region having the amino acid sequence of SEQ ID NO: 90;
32) a humanized monoclonal antibody or an antibody fragment thereof,
having
   a heavy chain variable region having the amino acid sequence of SEQ ID NO: 91, and
   a light chain variable region having the amino acid sequence of SEQ ID NO: 92;
33) a humanized monoclonal antibody or an antibody fragment thereof,
having
   a heavy chain variable region having the amino acid sequence of SEQ ID NO: 93, and
   a light chain variable region having the amino acid sequence of SEQ ID NO: 92;
34) a humanized monoclonal antibody or an antibody fragment thereof,
having
   a heavy chain variable region having the amino acid sequence of SEQ ID NO: 91, and
   a light chain variable region having the amino acid sequence of SEQ ID NO: 94;
35) a humanized monoclonal antibody or an antibody fragment thereof,
having
   a heavy chain variable region having the amino acid sequence of SEQ ID NO: 93, and
   a light chain variable region having the amino acid sequence of SEQ ID NO: 94;
36) a humanized monoclonal antibody or an antibody fragment thereof,
having
   a heavy chain variable region having the amino acid sequence of SEQ ID NO: 95, and
   a light chain variable region having the amino acid sequence of SEQ ID NO: 96;
37) a humanized monoclonal antibody or an antibody fragment thereof,
having
   a heavy chain variable region having the amino acid sequence of SEQ ID NO: 97, and
   a light chain variable region having the amino acid sequence of SEQ ID NO: 96;

38) a humanized monoclonal antibody or an antibody fragment thereof,
having
a heavy chain variable region having the amino acid sequence of SEQ ID NO: 98, and
a light chain variable region having the amino acid sequence of SEQ ID NO: 96;
39) a humanized monoclonal antibody or an antibody fragment thereof,
having
a heavy chain variable region having the amino acid sequence of SEQ ID NO: 99, and
a light chain variable region having the amino acid sequence of SEQ ID NO: 96;
40) a humanized monoclonal antibody or an antibody fragment thereof,
having
a heavy chain variable region having the amino acid sequence of SEQ ID NO: 100, and
a light chain variable region having the amino acid sequence of SEQ ID NO: 101;
41) a humanized monoclonal antibody or an antibody fragment thereof,
having
a heavy chain variable region having the amino acid sequence of SEQ ID NO: 100, and
a light chain variable region having the amino acid sequence of SEQ ID NO: 102;
42) a humanized monoclonal antibody or an antibody fragment thereof,
having
a heavy chain variable region having the amino acid sequence of SEQ ID NO: 100, and
a light chain variable region having the amino acid sequence of SEQ ID NO: 103;
43) a humanized monoclonal antibody or an antibody fragment thereof,
having
a heavy chain variable region having the amino acid sequence of SEQ ID NO: 100, and
a light chain variable region having the amino acid sequence of SEQ ID NO: 104; and
44) a humanized monoclonal antibody or an antibody fragment thereof,
having
a heavy chain variable region having the amino acid sequence of SEQ ID NO: 100, and
a light chain variable region having the amino acid sequence of SEQ ID NO: 105.

4. The humanized monoclonal antibody or an antibody fragment thereof according to claim 3, wherein said antibody fragment is Fab, F(ab')$_2$, Fab', scFv, dsFv or Diabody.

5. A humanized monoclonal antibody or an antibody fragment thereof,
selected from the group of
1) a humanized monoclonal antibody or an antibody fragment thereof,
having
a heavy chain variable region having the amino acid sequence of SEQ ID NO: 60, and
a light chain variable region having the amino acid sequence of SEQ ID NO: 64;
2) a humanized monoclonal antibody or an antibody fragment thereof,
having
a heavy chain variable region having the amino acid sequence of SEQ ID NO: 60, and
a light chain variable region having the amino acid sequence of SEQ ID NO: 67;
3) a humanized monoclonal antibody or an antibody fragment thereof,
having
a heavy chain variable region having the amino acid sequence of SEQ ID NO: 60, and
a light chain variable region having the amino acid sequence of SEQ ID NO: 68;
4) a humanized monoclonal antibody or an antibody fragment thereof,
having
a heavy chain variable region having the amino acid sequence of SEQ ID NO: 60, and
a light chain variable region having the amino acid sequence of SEQ ID NO: 69;
5) a humanized monoclonal antibody or an antibody fragment thereof,
having
a heavy chain variable region having the amino acid sequence of SEQ ID NO: 62, and
a light chain variable region having the amino acid sequence of SEQ ID NO: 64;
6) a humanized monoclonal antibody or an antibody fragment thereof,
having
a heavy chain variable region having the amino acid sequence of SEQ ID NO: 63, and
a light chain variable region having the amino acid sequence of SEQ ID NO: 67;
7) a humanized monoclonal antibody or an antibody fragment thereof,
having
a heavy chain variable region having the amino acid sequence of SEQ ID NO: 63, and
a light chain variable region having the amino acid sequence of SEQ ID NO: 68;
8) a humanized monoclonal antibody or an antibody fragment thereof,
having
a heavy chain variable region having the amino acid sequence of SEQ ID NO: 63, and
a light chain variable region having the amino acid sequence of SEQ ID NO: 69;
9) a humanized monoclonal antibody or an antibody fragment thereof,
having
a heavy chain variable region having the amino acid sequence of SEQ ID NO: 65, and
a light chain variable region having the amino acid sequence of SEQ ID NO: 67;
10) a humanized monoclonal antibody or an antibody fragment thereof,
having
a heavy chain variable region having the amino acid sequence of SEQ ID NO: 65, and
a light chain variable region having the amino acid sequence of SEQ ID NO: 68;
11) a humanized monoclonal antibody or an antibody fragment thereof,
having
a heavy chain variable region having the amino acid sequence of SEQ ID NO: 65, and
a light chain variable region having the amino acid sequence of SEQ ID NO: 69;

12) a humanized monoclonal antibody or an antibody fragment thereof,
having
   a heavy chain variable region having the amino acid sequence of SEQ ID NO: 66, and
   a light chain variable region having the amino acid sequence of SEQ ID NO: 67;
13) a humanized monoclonal antibody or an antibody fragment thereof,
having
   a heavy chain variable region having the amino acid sequence of SEQ ID NO: 66, and
   a light chain variable region having the amino acid sequence of SEQ ID NO: 68;
14) a humanized monoclonal antibody or an antibody fragment thereof,
having
   a heavy chain variable region having the amino acid sequence of SEQ ID NO: 66, and
   a light chain variable region having the amino acid sequence of SEQ ID NO: 69;
15) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 73;
16) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 78;
17) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 79;
18) a humanized monoclonal antibody or an antibody fragment thereof,
having
   a heavy chain variable region having the amino acid sequence of SEQ ID NO: 70, and
   a light chain variable region having the amino acid sequence of SEQ ID NO: 80;
19) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 76;
20) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 78;
21) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 79;
22) a humanized monoclonal antibody or an antibody fragment thereof,
having
   a heavy chain variable region having the amino acid sequence of SEQ ID NO: 72, and
   a light chain variable region having the amino acid sequence of SEQ ID NO: 80;
23) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 76;
24) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 78;
25) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 79;
26) a humanized monoclonal antibody or an antibody fragment thereof,
having
   a heavy chain variable region having the amino acid sequence of SEQ ID NO: 74, and
   a light chain variable region having the amino acid sequence of SEQ ID NO: 80;
27) a humanized monoclonal antibody or an antibody fragment thereof,
having
   a heavy chain variable region having the amino acid sequence of SEQ ID NO: 75, and
   a light chain variable region having the amino acid sequence of SEQ ID NO: 76;
28) a humanized monoclonal antibody or an antibody fragment thereof,
having
   a heavy chain variable region having the amino acid sequence of SEQ ID NO: 75, and
   a light chain variable region having the amino acid sequence of SEQ ID NO: 78;
29) a humanized monoclonal antibody or an antibody fragment thereof,
having
   a heavy chain variable region having the amino acid sequence of SEQ ID NO: 75, and
   a light chain variable region having the amino acid sequence of SEQ ID NO: 79;

30) a humanized monoclonal antibody or an antibody fragment thereof,
having
a heavy chain variable region having the amino acid sequence of SEQ ID NO: 75, and
a light chain variable region having the amino acid sequence of SEQ ID NO: 80;
31) a humanized monoclonal antibody or an antibody fragment thereof,
having
a heavy chain variable region having the amino acid sequence of SEQ ID NO: 77, and
a light chain variable region having the amino acid sequence of SEQ ID NO: 71;
32) a humanized monoclonal antibody or an antibody fragment thereof,
having
a heavy chain variable region having the amino acid sequence of SEQ ID NO: 77, and
a light chain variable region having the amino acid sequence of SEQ ID NO: 73;
33) a humanized monoclonal antibody or an antibody fragment thereof,
having
a heavy chain variable region having the amino acid sequence of SEQ ID NO: 77, and
a light chain variable region having the amino acid sequence of SEQ ID NO: 76;
34) a humanized monoclonal antibody or an antibody fragment thereof,
having
a heavy chain variable region having the amino acid sequence of SEQ ID NO: 81, and
a light chain variable region having the amino acid sequence of SEQ ID NO: 71;
35) a humanized monoclonal antibody or an antibody fragment thereof,
having
a heavy chain variable region having the amino acid sequence of SEQ ID NO: 81, and
a light chain variable region having the amino acid sequence of SEQ ID NO: 73;
36) a humanized monoclonal antibody or an antibody fragment thereof,
having
a heavy chain variable region having the amino acid sequence of SEQ ID NO: 81, and
a light chain variable region having the amino acid sequence of SEQ ID NO: 76;
37) a humanized monoclonal antibody or an antibody fragment thereof,
having
a heavy chain variable region having the amino acid sequence of SEQ ID NO: 81, and
a light chain variable region having the amino acid sequence of SEQ ID NO: 80;
38) a humanized monoclonal antibody or an antibody fragment thereof,
having
a heavy chain variable region having the amino acid sequence of SEQ ID NO: 86, and
a light chain variable region having the amino acid sequence of SEQ ID NO: 83; and
39) a humanized monoclonal antibody or an antibody fragment thereof,
having
a heavy chain variable region having the amino acid sequence of SEQ ID NO: 86, and
a light chain variable region having the amino acid sequence of SEQ ID NO: 84.

6. The humanized monoclonal antibody or an antibody fragment thereof according to claim 5, wherein said antibody fragment is Fab, F(ab')$_2$, Fab', scFv, dsFv or Diabody.

7. A pharmaceutical composition for treating or preventing a disease related to vascular endothelial lipase, comprising the humanized monoclonal antibody or the antibody fragment thereof of claim 1.

8. The pharmaceutical composition of claim 7, wherein the disease related to vascular endothelial lipase is dyslipidemia.

9. A pharmaceutical composition for treating or preventing a disease related to vascular endothelial lipase, comprising the humanized monoclonal antibody or the antibody fragment thereof of claim 3.

10. The pharmaceutical composition of claim 9, wherein the disease related to vascular endothelial lipase is dyslipidemia.

11. A pharmaceutical composition for treating or preventing a disease related to vascular endothelial lipase, comprising the humanized monoclonal antibody or the antibody fragment thereof of claim 5.

12. The pharmaceutical composition of claim 11, wherein the disease related to vascular endothelial lipase is dyslipidemia.

13. A humanized monoclonal antibody or an antibody fragment thereof,
having
a heavy chain variable region
including three CDRs having the amino acid sequence of SEQ ID NO: 25, the amino acid sequence of SEQ ID NO: 106 and the amino acid sequence of SEQ ID NO: 24, and
a light chain variable region
including three CDRs having the amino acid sequence of SEQ ID NO: 16, the amino acid sequence of SEQ ID NO: 17 and the amino acid sequence of SEQ ID NO: 18.

14. A pharmaceutical composition for treating or preventing a disease related to vascular endothelial lipase, comprising the humanized monoclonal antibody or the antibody fragment thereof of claim 13.

15. The pharmaceutical composition of claim 14, wherein the disease related to vascular endothelial lipase is dyslipidemia.

16. A humanized monoclonal antibody or an antibody fragment thereof,
having
a heavy chain variable region having the amino acid sequence of SEQ ID NO: 75, and
a light chain variable region having the amino acid sequence of SEQ ID NO: 76.

17. A pharmaceutical composition for treating or preventing a disease related to vascular endothelial lipase, comprising the humanized monoclonal antibody or the antibody fragment thereof of claim 16.

18. The pharmaceutical composition of claim 17, wherein the disease related to vascular endothelial lipase is dyslipidemia.

* * * * *